(12) United States Patent
Stoecker et al.

(10) Patent No.: US 11,371,991 B2
(45) Date of Patent: Jun. 28, 2022

(54) DIAGNOSIS OF A NEUROAUTOIMMUNE DISEASE

(71) Applicant: EUROIMMUN MEDIZINISCHE LABORDIAGNOSTIKA AG, Luebeck (DE)

(72) Inventors: Winfried Stoecker, Groß Grönau (DE); Lars Komorowski, Ratzeburg (DE); Ramona Miske, Lübeck (DE); Yvonne Denno, Lübeck (DE); Madeleine Scharf, Selmsdorf (DE); Christian Probst, Ratzeburg (DE); Iswariya Venkataraman, Lübeck (DE); Stephanie Kade, Wismar (DE)

(73) Assignee: EUROIMMUN MEDIZINISCHE LABORDIAGNOSTIKA AG, Luebeck (DE)

( * ) Notice: Subject to any disclaimer, the term of this patent is extended or adjusted under 35 U.S.C. 154(b) by 197 days.

(21) Appl. No.: 16/904,023

(22) Filed: Jun. 17, 2020

(65) Prior Publication Data

US 2020/0309775 A1 Oct. 1, 2020

Related U.S. Application Data

(62) Division of application No. 16/009,647, filed on Jun. 15, 2018, now Pat. No. 10,725,035.

(30) Foreign Application Priority Data

Jun. 16, 2017 (EP) ..................................... 17001026
Jun. 16, 2017 (EP) ..................................... 17001205

(51) Int. Cl.
| | | |
|---|---|---|
| *G01N 33/564* | (2006.01) | |
| *G01N 33/50* | (2006.01) | |
| *C07K 1/14* | (2006.01) | |
| *C07K 16/18* | (2006.01) | |

(52) U.S. Cl.
CPC ............. *G01N 33/564* (2013.01); *C07K 1/14* (2013.01); *C07K 16/18* (2013.01); *G01N 33/502* (2013.01); *G01N 2800/24* (2013.01); *G01N 2800/28* (2013.01)

(58) Field of Classification Search
CPC ............... G01N 33/564; G01N 33/502; G01N 2800/28; C07K 1/14
See application file for complete search history.

(56) References Cited

U.S. PATENT DOCUMENTS

| | | | |
|---|---|---|---|
| 4,647,543 A | 3/1987 | Stöcker | |
| 5,693,476 A | 12/1997 | Scheller | |
| 10,466,239 B2 | 11/2019 | Stoecker et al. | |
| 2013/0273579 A1 | 10/2013 | Sawasaki et al. | |
| 2015/0247847 A1 | 9/2015 | Dalmau | |
| 2016/0349275 A1 | 12/2016 | Dalmau et al. | |

FOREIGN PATENT DOCUMENTS

| | | |
|---|---|---|
| EP | 2 423 226 A2 | 2/2012 |
| EP | 2 863 231 A1 | 4/2015 |
| EP | 2 952 898 A1 | 12/2015 |
| EP | 3 018 478 A1 | 5/2016 |
| EP | 3 026 434 A1 | 6/2016 |
| EP | 3 086 120 A1 | 10/2016 |
| EP | 3 101 424 A1 | 12/2016 |
| EP | 2 483 417 B1 | 3/2017 |
| WO | 97/21729 A1 | 6/1997 |
| WO | 2013/041540 A1 | 3/2013 |

OTHER PUBLICATIONS

Black et al., "Advances in the design and delivery of peptide subunit vaccines with a focus on Toll-like receptor agonists," *Expert Rev. Vaccines* 9(2):157-173, 2010.
Bonilla et al., "Immunofluorescence microscopy is superior to fluorescent beads for detection of antinuclear antibody reactivity in systemic lupus erythematosus patients," *Clin. Immunol.* 124(1):18-21, 2007.
Communication pursuant to Article 94(3) EPC for corresponding European Application No. 18 178 018.0-1118, (7 pages), dated Jul. 11, 2019.
English et al., "The Neuroproteomics of Schizophrenia," *Biol Psychiatry* 69:163-172 (2011).
Hirai et al., "Selective Screening of Secretory Vesicle-Associated Proteins for Autoantigens in Type 1 Diabetes: VAMP2 and NPY are New Minor Autoantigens," *Clin. Immunol.* 127(3):366-374, 2008.
Hong et al., "Tethering the assembly of SNARE complexes," *Trends in Cell Biology* 24(1):35-43, 2014.
Jackson et al., "Preparation and properties of totally synthetic immunogens," *Vaccine* 18:355-361, 2000.
Miske et al., "Autoantibodies against glutamate receptor δ2 after allogenic stem cell transplantation," *Neurol. Neuroimmunol. Neuroinflamm.* 3(4), 2016, 6 pages.

(Continued)

*Primary Examiner* — Olga N Chernyshev
(74) *Attorney, Agent, or Firm* — Seed IP Law Group LLP

(57) ABSTRACT

The present invention relates to a method for diagnosing a disease comprising the step detecting in a sample comprising antibodies from a patient an autoantibody binding to a polypeptide selected from the group comprising NSF, STX1B, DNM1 and VAMP2, a polypeptide comprising a polypeptide selected from the group comprising NSF, STX1B, DNM1 and VAMP2, or a variant thereof, a use of said polypeptide for the diagnosis of a disease, an autoantibody binding to a polypeptide selected from the group comprising NSF, STX1B, DNM1 and VAMP2, a use of the autoantibody for the diagnosis of a disease, a method for isolating an autoantibody binding to a polypeptide selected from the group comprising NSF, STX1B, DNM1 and VAMP2, a pharmaceutical composition or medical device comprising said polypeptide according to the present invention, a kit for the diagnosis of a disease comprising said polypeptide or said medical device and a use of said polypeptide or autoantibody for the manufacture of a kit or medical device.

11 Claims, 12 Drawing Sheets
(12 of 12 Drawing Sheet(s) Filed in Color)
Specification includes a Sequence Listing.

(56) References Cited

OTHER PUBLICATIONS

Miske et al., "Neurochondrin is a neuronal target antigen in autoimmune cerebellar degeneration," *Neurol. Neuroimmunol. Neuroinflamm.* 4(1), 2017, 9 pages.
Nicot et al., "Regulation of gene expression in experimental autoimmune encephalomyelitis indicates early neuronal dysfunction," *Brain* 126:398-412, 2003.
Raoult et al., "Line Blot and Western Blot Immunoassays for Diagnosis of Mediterranean Spotted Fever," *Journal of Clinical Microbiology* 27(9):2073-2079, 1989.
Scharf et al., "Neuronal $Na^+/K^+$ ATPase is an autoantibody target in paraneoplastic neurologic syndrome," *Neurology* 84(16):1673-1679, 2015, (8 pages).
Südhof et al., "Synaptic Vesicle Exocytosis," *Cold Spring Harbor Perspectives in Biology* 3(12):a005637, 2011, (15 pages).
Voigt et al., "Automated Indirect Immunofluorescence Evaluation of Antinuclear Autoantibodies on HEp-2 Cells," *Clinical and Developmental Immunology* 2012:651058, 2012, 7 pages.
Venkataraman, "Identification of novel autoantigens in Stiff-Person Syndrome and associated hyperexcitability disorders," *Dissertation for the Fulfilment of Requirements for the Doctoral Degree of the University of Lübeck*, 129 pages, (2017).
Zhu et al., "Protein Repair in the Brain, Proteomic Analysis of Endogenous Substrates for Protein $_L$-Isoaspartyl Methyltransferase in Mouse Brain," *The Journal of Biological Chemistry* 281(44):33802-33813 (2006).
Summons to attend oral proceedings, for European Application No. 18178018, dated Jan. 12, 2021, 7 pages.
Result of consultation for European Application No. 18178018, dated Dec. 22, 2020, 4 pages.
Result of consultation for European Application No. 18178018, dated Dec. 11, 2020, 4 pages.
Blöcker et al., "A new recombinant cell-based IFA for the determination of autoantibodies to GAD in stiff-person syndrome," *J Neuro Im*: 21, Abstract No. 95, 2014, 1 page.
Communication of Oral Proceedings for European Application No. 18178018.0, dated Oct. 23, 2020, 3 pages.
Extended European Search Report for European Application No. 17001205.8, dated Nov. 20, 2017, 12 pages.
Extended European Search Report for European Application No. 18178018.0, dated Oct. 9, 2018, 12 pages.
German Office Action for German Application No. 10 2018 004 759.9, dated Apr. 22, 2020, 18 pages (with English Machine Translation).
Mimics et al., "Molecular Characterization of Schizophrenia Viewed by Microarray Analysis of Gene Expression in Prefrontal Cortex," *Neuron* 28:53-61, 2000.
Probst et al., "Autoantibodies against glycine-associated synaptic proteins in stiff-person syndrome," *J Neuro Im*: 21-22, Abstract 96, 2014, 2 pages.
Stöcker et al., "Autoantikörpedrdiagnostik in der Nuerologie mittels nativer und rekombinanter Antigensubstrate," *Nervenarzt* 84:471-476, 2013 (with English Abstract) (8 pages).
Summons to Oral Proceedings for European Application No. 18178018. 0, dated Jul. 9, 2020, 8 pages.
Venkataraman et al., "Antigenic targets of autoantibodies in dementia," *EuroImmun*:2014, Conference Paper, 2 pages.
Venkataraman et al., "Autoantibodies in Alzheimer's Disease," *The Journal of Alzheimer's Association* 10(4):P359, Poster Presentation P1-160, 2014 (1 page).
Venkataraman et al., "Screening for additional autoantigens in individuals with autoantibodies against glutamic acid decarboxylase," *EuroImmun*:2015, Conference Paper, 1 page.

FIG. 2A
FIG. 2B
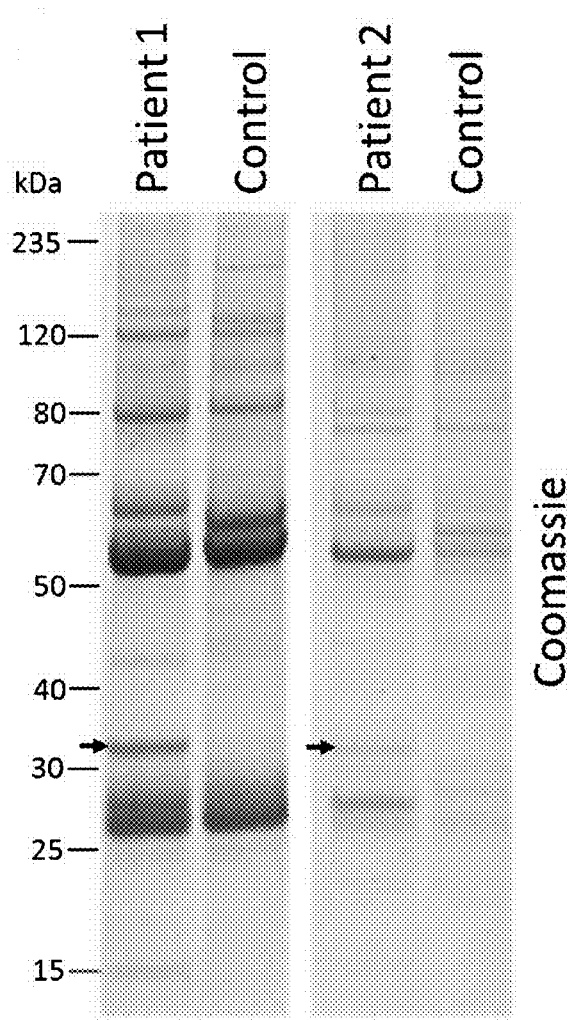
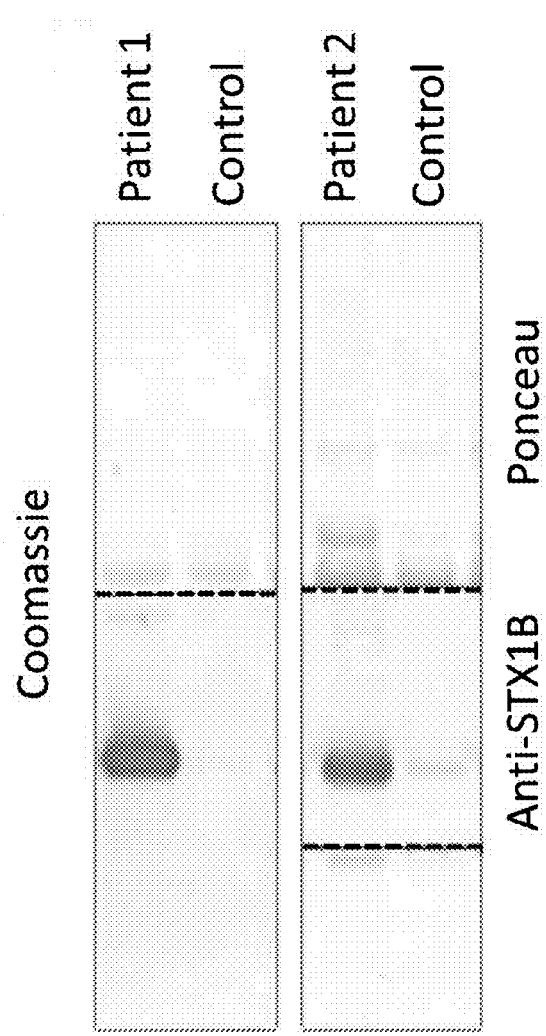

FIG. 3C

Patient 1
+ control extract

Patient 1
+ STX1B extract

FIG. 6A
FIG. 6B
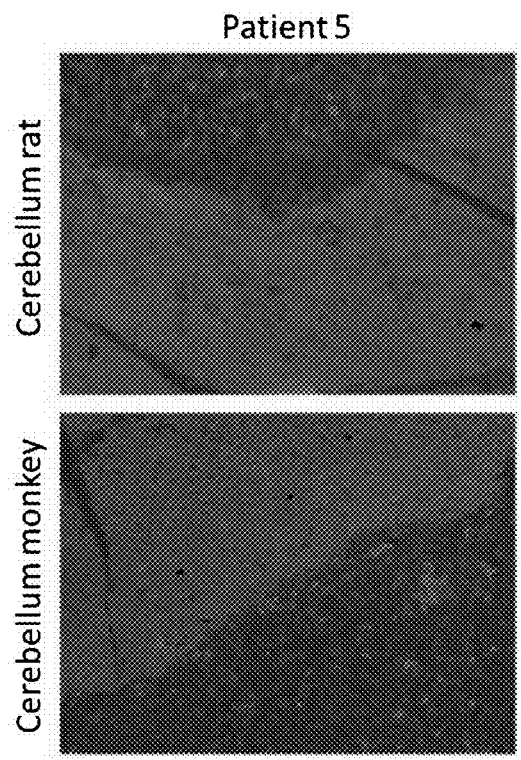
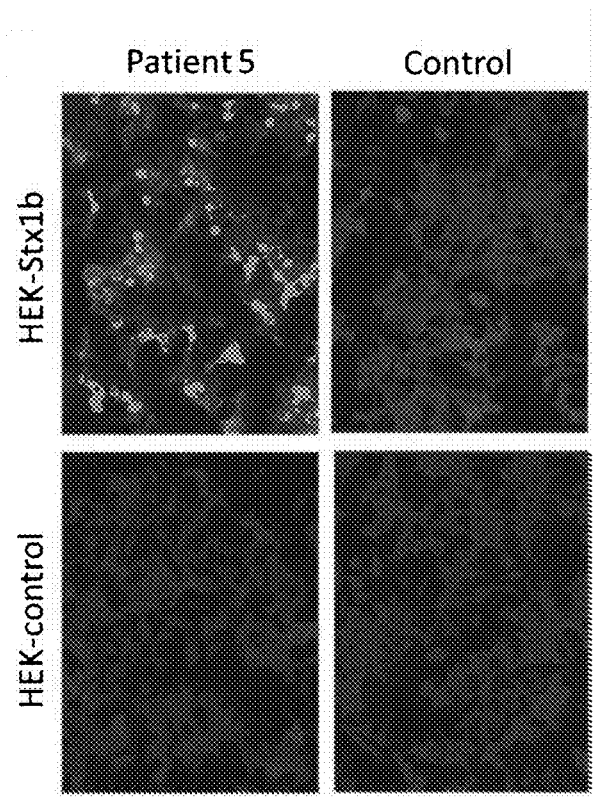

DIAGNOSIS OF A NEUROAUTOIMMUNE DISEASE

RELATED APPLICATION DATA

This application is a divisional application of U.S. application Ser. No. 16/009,647, filed on Jun. 15, 2018, which claims priority to European Application Nos. 17001026.8 and 17001205.8, both filed Jun. 16, 2017. U.S. application Ser. No. 16/009,647 is herein incorporated by reference in its entity.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310159_412D1_SEQUENCE_LISTING.txt. The text file is 71 KB, was created on Jun. 11, 2020, and is being submitted electronically via EFS-Web.

The present invention relates to a method for diagnosing a disease comprising the step detecting in a sample comprising antibodies from a patient an autoantibody binding to a polypeptide selected from the group comprising NSF, STX1B, DNM1 and VAMP2, a polypeptide comprising a polypeptide selected from the group comprising NSF, STX1B, DNM1 and VAMP2, or a variant thereof, a use of said polypeptide for the diagnosis of a disease, an autoantibody binding to a polypeptide selected from the group comprising NSF, STX1B, DNM1 and VAMP2, a use of the autoantibody for the diagnosis of a disease, a method for isolating an autoantibody binding to a polypeptide selected from the group comprising NSF, STX1B, DNM1 and VAMP2, a pharmaceutical composition or medical device comprising said polypeptide according to the present invention, a kit for the diagnosis of a disease comprising said polypeptide or said medical device and a use of said polypeptide or autoantibody for the manufacture of a kit or medical device.

Developing diagnostic systems for neurological diseases is a continuing challenge in biomedical science, not in the least because many symptoms encountered may be accounted for by a huge variety of causes including genetically-inherited diseases, drug abuse, malnutrition, infection, injury, psychiatric illness, immunological defects and cancer.

Since a neurological disease is rarely associated with a unique characteristic pattern of clinical symptoms, it is often difficult to provide a reliable diagnosis solely based on the observation and examination of the patients affected or their medical history.

The importance of an early diagnosis cannot be overemphasized. Many neurological disorders, most prominently Alzheimer's and Parkinson's diseases as well as Multiple Sclerosis, cannot be cured, but drugs are available that may be used to slow down their progression. In addition, certain rare types of cancer are associated with neurological symptoms. The earlier the diagnosis, the better the chances to exploit the spectrum of available therapies to the full benefit of the patient.

This holds all the more true in the case of neurological diseases associated with autoantibodies. In some cases, the link between a specific detectable autoantibody and a condition is sufficiently strong to allow for an immediate diagnosis.

But even if it is not, the detection of autoantibodies may point the physician in charge to therapeutic means that may be used to ameliorate the patient's condition. There is a variety of widely used immunosuppressants that may be used regardless of the nature of the autoantibody's target. Alternatively, apheresis may be used to remove autoantibodies from the patient's blood. In many cases, patients went on to lead a normal life following early diagnosis and treatment of a neurological autoimmune disease.

Diagnostic assays based on the detection of autoantibodies may also corroborate the diagnosis of diseases other than those associated with autoantibodies. If it turns out that a blood sample is devoid of specific autoantibodies, this is likely to help the physician in charge exclude a range of possibilities and thus narrow down the spectrum of plausible conditions.

Examples of neurological conditions coinciding with the emergence of autoantibodies include Neuromyelitis optica, a disease characterized by loss of visual perception and spinal cord function, and anti-NMDA receptor encephalitis, which is associated with autonomic dysfunction, hypoventilation, cerebellar ataxia, hemiparesis, loss of consciousness, or catatonia. Whilst the involvement of autoantibodies and the nature of these conditions as such was previously poorly understood, many of this disease can now be diagnosed and treated efficiently owing to the availability of assays based on the detection of autoantibodies.

Therefore, it is paramount that new approaches be developed to distinguish neurological conditions associated with autoantibodies from those that are not.

WO1997/021729 and U.S. Pat. No. 5,693,476 disclose the use of NSF, syntaxins and VAMP proteins as part of artificially formed complexes to identify substances that modulate synaptic transmission but do not disclose the existence, let alone diagnostical usefulness of an autoantibody binding to a polypeptide selected from the group comprising NSF, STX1B, DNM1 and VAMP2.

Nicot et al. report decreased transcript and protein levels of STX1B in murine experimental autoimmune encephalitis (Nicot A, Ratnakar P V, Ron Y, Chen C C, Elkabes S. Regulation of gene expression in experimental autoimmune encephalomyelitis indicates early neuronal dysfunction. Brain. 2003 February; 126(Pt 2):398-412), but do not disclose the existence, let alone diagnostical usefulness of autoantibody binding to a polypeptide selected from the group comprising NSF, STX1B, DNM1 and VAMP2.

Hirai et al. report autoantibodies against VAMP2 in 21% of patients with type 1 diabetes (Hirai H, Miura J, Hu Y, Larsson H, Larsson K, Lernmark A, Ivarsson S A, Wu T, Kingman A, Tzioufas A G, Notkins A L. Selective screening of secretory vesicle-associated proteins for autoantigens in type 1 diabetes: VAMP2 and NPY are new minor autoantigens. Clin Immunol. 2008 June; 127(3):366-74) by an in vitro-transcription/translation immunoprecipitation protocol directed at secretory vesicle-associated proteins. In the same report, the authors disclose that they did not detect any antibodies against STX1A, a protein with 97.6% homology to STX1B. They do not disclose the existence, let alone diagnostical usefulness of an autoantibody binding to a polypeptide selected from the group comprising NSF, DNM1 and STX1B. Furthermore, the autoantibody binding to VAMP2 was not considered a marker for diagnosing neurological disorders.

The problem underlying the present invention is to provide novel reagents, devices and methods that may be used to support the diagnosis and treatment of an autoimmune disease, preferably an autoimmune disease of the nervous system or associated with a neurological disease or neurological symptoms, more preferably selected from the group comprising stiff-person syndrome and encephalitis, preferably encephalitis.

Another problem underlying the present invention is to provide novel reagents, devices and methods that may be used to distinguish autoimmune diseases, in particular neurological autoimmune diseases, more preferably selected from the group comprising stiff-person syndrome and encephalitis, preferably encephalitis, from diseases other than autoimmune diseases, not in the least to determine the most promising treatment regimen, more specifically whether or not an immunosuppressive treatment is adequate.

The problem underlying the present invention is solved by the subject-matter of the attached independent and dependent claims.

In a first aspect, the problem is solved by a method for diagnosing a disease comprising the step detecting in a sample comprising antibodies from a patient an autoantibody binding to a polypeptide selected from the group comprising NSF, STX1B, DNM1 and VAMP2.

In a second aspect, the problem is solved by a polypeptide comprising a polypeptide selected from the group comprising NSF, STX1B, DNM1 and VAMP2 or a variant thereof, which is preferably immobilized, more preferably on a solid carrier.

In a third aspect, the problem is solved by a use of a polypeptide according to the present invention for the diagnosis of a disease, preferably comprising the step detecting in a sample an autoantibody binding to a polypeptide selected from the group comprising NSF, STX1B, DNM1 and VAMP2.

In a 4$^{th}$ aspect, the problem is solved by the polypeptide according to the present invention for use in a treatment of a disease.

In a 5$^{th}$ aspect, the problem is solved by an autoantibody, preferably an isolated autoantibody binding to a polypeptide selected from the group comprising NSF, STX1B, DNM1 and VAMP2, wherein the antibody is preferably in complex with the polypeptide according to the present invention.

In a 6$^{th}$ aspect, the problem is solved by a use of the autoantibody according to the present invention for the diagnosis of a disease.

In a 7$^{th}$ aspect, the problem is solved by a method for isolating an autoantibody binding to a polypeptide selected from the group comprising NSF, STX1B, DNM1 and VAMP2, comprising the steps
 a) contacting a sample comprising the autoantibody with a polypeptide according to the present invention under conditions compatible with formation of a complex, wherein said autoantibody binds to said polypeptide,
 b) isolating the complex formed in step a),
 c) dissociating the complex isolated in step b) and
 d) separating the autoantibody from the polypeptide.

In an 8$^{th}$ aspect, the problem is solved by a pharmaceutical composition or medical device, preferably diagnostic device, comprising the polypeptide according to the present invention.

In a 9$^{th}$ aspect the problem is solved by a kit for the diagnosis of a disease, which kit comprises the polypeptide according to the present invention or the medical device according to the present invention, wherein preferably the kit comprises in addition a means for detecting a complex comprising the polypeptide according to the present invention and/or an antibody binding to a polypeptide selected from the group comprising NSF, STX1B, DNM1 and VAMP2.

In another aspect, the method according to the present invention is a method for calibrating a diagnostic test system or for ascertaining the reliability and/or sufficient capacity of such a test system or a therapeutic system for removing autoantibodies from the blood of a patient. In the case of a diagnostic test system, autoantibodies are not detected in a sample from a patient to be diagnosed, but are detected in an artificial solution of known composition, in particular comprising a defined concentration of autoantibody or a recombinant antibody of defined concentration which binds to the autoantigen. This artificial solution can be used as a positive control. The term "calibrating", as used herein, can be understood as using an antibody binding to a polypeptide selected from the group comprising NSF, STX1B, DNM1 and VAMP2 or a variant thereof on the diagnostic test system to obtain qualitative, semi-quantitative or quantitative data of the antibody binding to a corresponding antigen. Preferably, the antigen may be a polypeptide selected from the group comprising NSF, STX1B, DNM1 and VAMP2 or a variant expressed in a cell of a tissue section or a cell transfected with a nucleic acid molecule comprising the genetic information to express the antigen of interest. The diagnostic system may be any system that allows the detection of autoantibodies in a sample, such as a medical or diagnostic device according to the present invention.

In the case of a therapeutic system, for example an apparatus for apharesis, the method may be used to develop such a system and test its reliability and/or efficiency and/or capacity. For example, following an apharesis run or prior to starting an apharesis run, a solution comprising a defined concentration of an antibody binding to the polypeptide of the present invention may be contacted with the system, and the method according to the present invention may be used to confirming that the system is capable of depleting the solution of the antibody.

In a preferred embodiment, the patient has or the disease is associated with one or more, preferably two or more symptoms selected from the group comprising progressive stiffness in truncal muscles, including thoracolumbar paraspinal and abdominal muscles, abdominal wall muscles and proximal leg, rigid gait, lumbar hyperlordosis, chronic pain, spasms in proximal limb and axial muscles, sensitivity to touch and sound, hyperekplexia, myoclonus, depression, anxiety, phobia, fever, headache, confusion, dysarthria, dysphagia, nystagmus, oscillopsia, vertigo, nausea, ataxia, paraesthesia, muscle wasting, dizziness, seizures, epilepsy and tremor.

In a 10$^{th}$ aspect, the problem is solved by a use of a polypeptide according to the present invention or the autoantibody according to the present invention or an antibody to a polypeptide from the group comprising NSF, STX1B, DNM1 and VAMP2 or the medical device according to the present invention for the manufacture of a kit, medical device, preferably diagnostic device, preferably for the diagnosis of a disease.

In a preferred embodiment, the disease is a neurological disease, preferably an autoimmune disease of the nervous system, more preferably selected from the group comprising stiff-person syndrome and encephalitis, preferably encephalitis. In a preferred embodiment, the method or use according to the present invention is intended to determine whether the disease, preferably neurological disease, has an autoimmune component, preferably one amenable to immunosuppressive treatment.

In a preferred embodiment, the sample is a bodily fluid comprising antibodies, preferably selected from the group comprising whole blood, serum, cerebrospinal fluid and saliva.

In a preferred embodiment, the autoantibody or complex is detected using a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, more preferably ELISA, chemiluminscence immunoassays, and immunofluorescence, preferably indirect immunofluorescence.

In a preferred embodiment, the medical device is selected from the group comprising a glass slide, preferably for microscopy, a biochip, a microtiter plate, a test strip, a membrane, preferably a line blot, a chromatography column and a bead, preferably a magnetic bead.

In a preferred embodiment, the autoantibody or complex is detected using a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, more preferably ELISA, chemiluminscence immunoassays, and immunofluorescence, preferably indirect immunofluorescence.

The present invention is based on the inventors' surprising finding that an autoantibody to NSF, an autoantibody to STX1B, an autoantibody to DNM1 and an autoantibody to VAMP2 exist and may be detected in samples from a number of patients suffering from neurological symptoms, but not in samples obtained from healthy subjects.

Furthermore, the present invention is based on the inventors' surprising finding that the novel neurological disease may be diagnosed by the way of detection of an autoantibody to a polypeptide selected from the group comprising NSF, STX1B, DNM1 and VAMP2

Without wishing to be bound to any theory, the presence of such autoantibodies suggests that activity and function of one or more than one polypeptide selected from the group comprising NSF, STX1B, DNM1 and VAMP2 and/or downstream effectors is impaired in patients having such autoantibodies to the effect that neurological symptoms occur.

N-ethylmaleimide sensitive fusion protein (NSF), syntaxin 1B (STX1B), dynamin 1 (DNM1) and vesicle-associated membrane protein 2 (VAMP2) are intracellular peripheral membrane proteins highly expressed in the brain, especially in the cell body and axons of neurons (Hong W, Lev S Tethering the assembly of SNARE complexes. Trends Cell Biol. 2014 24: 35-43).

They are part of SNARE (Soluble NSF Attachment Protein Receptor) complexes that are involved in the docking and/or fusion of synaptic vesicles with the presynaptic membrane in neurons. Thereby, NSF, STX1B, DNM1 and VAMP2, respectively, modulate neurotransmitter release, including release of gamma-amino butyric acid (GABA) and glycine from inhibitory neurons (Südhof T C, Rizo J. Synaptic vesicle exocytosis. Cold Spring Harb Perspect Biol. 2011 Dec. 1; 3(12). pii: a005637).

Cleavage of STX1B and VAMP2 by botulinum toxin from Clostridium botulinum, consisting of several proteases designated as botulinum neurotoxin A-G, abolishes the release of the neurotransmitter acetylcholine from axon endings at the neuromuscular junction and thus causes flaccid paralysis. Similarly, cleavage of VAMP2 by tetanus toxin from Clostridium tetani leads to lockjaw characterized by muscle spams.

NSF is a 82 kDa polypeptide containing 744 amino acids. It is required for vesicle-mediated transport. It catalyzes the fusion of transport vesicles within the Golgi cisternae. It is also required for transport from the endoplasmic reticulum to the Golgi stack. It seems to function as a fusion protein required for the delivery of cargo proteins to all compartments of the Golgi stack independent of vesicle origin.

STX1B is a 33 kDa polypeptide containing 288 amino acids. It is potentially involved in docking of synaptic vesicles at presynaptic active zones.

VAMP2 is a 13 kDa polypeptide containing 116 amino acids. It is involved in the targeting and/or fusion of transport vesicles to their target membrane. Modulates the gating characteristics of the delayed rectifier voltage-dependent potassium channel KCNB1.

STX1B and VAMP2 are part of the SNARE core complex in neurons.

DNM1 is a 97 kDa polypeptide containing 864 amino acids. Said protein possesses mechanochemical properties used to tubulate and sever membranes, and is involved in clathrin-mediated endocytosis and other vesicular trafficking processes. Actin and other cytoskeletal proteins act as binding partners for DNM1, which can also self-assemble leading to stimulation of GTPase activity.

The present invention relates to a polypeptide comprising a mammalian, preferably human polypeptide selected from the group comprising NSF, STX1B, DNM1 and VAMP2, or antigenic variants reactive to autoantibodies binding to NSF, STX1B, DNM1 or VAMP2, respectively. Mammalian NSF, STX1B, DNM1 and VAMP2 include those from human, monkey, mouse, rat, rabbit, guinea pig or pig and are preferably human NSF, STX1B, DNM1 and VAMP2.

In a more preferred embodiment, NSF is the polypeptide encoded by the data base codes P46459-1 or P46459-2, preferably P46459-1. The data base codes of the corresponding cDNA are NM_006178 (NCBI), respectively. Throughout this application, any data base codes cited refers to the Uniprot data base, more specifically the version on the filing date of this application or its earliest priority application.

In a more preferred embodiment, STX1B is the polypeptide encoded by data base codes P61266-1 or P61266-2, preferably P61266-1. The data base codes of the corresponding cDNA are NM_052874 (NCBI), respectively.

In a more preferred embodiment, DNM1 is the polypeptide encoded by data base codes Q05193, preferably Q05193-1 (UniProt). The data base codes of the corresponding cDNA are NM_004408 (NCBI), respectively.

In a more preferred embodiment, VAMP2 is the polypeptide encoded by data base code P63027-1. The data base codes of the corresponding cDNA are NM_014232 (NCBI), respectively.

The teachings of the present invention may not only be carried out using polypeptides, in particular a polypeptide comprising the native sequence of a polypeptide selected from the group comprising NSF, STX1B, DNM1 and VAMP2 or nucleic acids having the exact sequences referred to in this application explicitly, for example by function, name, sequence or accession number, or implicitly, but also using variants of such polypeptides or nucleic acids.

In a preferred embodiment, the term "variant", as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150 or 200 successive amino acids of the original sequence or a variant thereof. The total length of the variant may be at least 6, 7, 8, 9, 10, 11, 12, 20, 25, 30, 40, 50, 60, 70, 80, 90, 100 or more amino acids.

In another preferred embodiment, the term "variant" relates not only to at least one fragment, but also to a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, $3^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings.

In a preferred embodiment, the variant is a linear, non-folded polypeptide, which is optionally denatured.

In a preferred embodiment, the polypeptide and variants thereof may, in addition, comprise chemical modifications, for example isotopic labels or covalent modifications such as glycosylation, phosphorylation, acetylation, decarboxylation, citrullination, methylation, hydroxylation and the like. The person skilled in the art is familiar with methods to modify polypeptides. Any modification is designed such that it does not abolish the biological activity of the variant.

Moreover, variants may also be generated by fusion with other known polypeptides or variants thereof and comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In a preferred embodiment, the term "variant" of a nucleic acid comprises nucleic acids the complementary strand of which hybridizes, preferably under stringent conditions, to the reference or wild type nucleic acid. Stringency of hybridization reactions is readily determinable by one of ordinary skilled in the art, and in general is an empirical calculation dependent on probe length, washing temperature and salt concentration. In general longer probes require higher temperatures for proper annealing, while shorter probes less so. Hybridization generally depends on the ability of denatured DNA to reanneal to complementary strands present in an environment below their melting temperature: The higher the degree of desired homology between the probe and hybridizable sequence, the higher the relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the probe is 70% or more identical to the target sequence. Probes having a lower degree of identity with respect to the target sequence may hybridize, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence and variants thereof as the reference nucleic acid sequence, in line with the degeneracy of the genetic code.

The variant of the polypeptide has biological activity. In a preferred embodiment, such biological activity is the ability to bind to an autoantibody binding to the respective polypeptide selected from the group comprising NSF, STX1B, DNM1 and VAMP2, as found in a patient suffering from an autoimmune disease associated with such autoantibody, preferably associated with a neurological disease such as stiff-person syndrome, paraneoplastic stiff-person syndrome, progressive encephalomyelitis with rigidity and myoclonus and encephalitiy, preferably stiff-person syndrome associated with such an autoantibody. For example, whether or not a variant of NSF has such biological activity may be checked by determining whether or not the variant of interest binds to an autoantibody from a sample of a patient which autoantibody binds to wild type NSF, preferably as determined by Western blotting using recombinant protein as described in the experimental section of this application. Whether or not a variant of STX1B has such biological activity may be checked by determining whether or not the variant of interest binds to an autoantibody from a sample of a patient which autoantibody binds to wild type STX1B, preferably as determined by indirect immunofluorescence with mammalian cells expressing STX1B as described in the experimental section of this application. Whether or not a variant of DNM1 has such biological activity may be checked by determining whether or not the variant of interest binds to an autoantibody from a sample of a patient which autoantibody binds to wild type DNM1, preferably as determined by indirect immunofluorescence with mammalian cells expressing DNM1 as described in the experimental section of this application. Whether or not a variant of VAMP2 has such biological activity may be checked by determining whether or not the variant of interest binds to an autoantibody from a sample of a patient which autoantibody binds to wild type VAMP2, preferably as determined by indirect immunofluorescence with mammalian cells expressing VAMP2 as described in the experimental section of this application.

The polypeptide according to the present invention, which comprises a polypeptide selected from the group comprising NSF, STX1B, DNM1 and VAMP2 or a variant thereof, including the autoantibody according to the present invention, when used to carry out the teachings of the present invention, may be provided in any form and at any degree of purification, from liquid samples, tissues or cells comprising said polypeptide in an endogenous form, more preferably cells overexpressing the polypeptide, crude or enriched lysates of such cells, to purified and/or isolated polypeptide which is optionally essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", "Purifying Challenging Proteins" (2009/2010), published by GE Healthcare Life Sciences, and in Burgess, R. R., Deutscher, M. P. (2009), Guide to Protein Purification). In a preferred embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection.

If the inventive polypeptide is provided in the form of tissue, it is preferred that the tissue is mammalian tissue, for example human, rat, primate, donkey, mouse, goat, horse, sheep, pig or cow, more preferably brain tissue, most preferably cerebellum. If a cell lysate is used, it is preferred that the cell lysate comprises the membranes associated with the surface of the cell or is in fact a fraction enriched in membranes. If said polypeptide is provided in the form of a recombinant cell, it is preferred that the recombinant cell is a eukaryotic cell such as a yeast cell, more preferably a cell from a multicellular eukaryote such as a plant, mammal, frog or insect, most preferably from a mammal, for example rat, human, primate, donkey, mouse, goat, horse, sheep, pig or cow.

The polypeptide used to carry out the inventive teachings, including any variants, is preferably designed such that it comprises at least one epitope recognized by and/or binds specifically to the autoantibody binding to a polypeptide selected from the group comprising NSF, STX1B, DNM1 and VAMP2. Any epitope is more preferably an epitope recognized by such an autoantibody only, by contrast to antibodies other than an autoantibody to NSF, DNM1, STX1B or VAMP2. In one embodiment, such epitope comprises a stretch of 6, 7, 8, 9, 10, 11, 12, 20, 25, 30, 40, 50, 60, 70, 80, 90, 100 or more, preferably at least 9 but no more than 16, consecutive amino acids from NSF, STX1B, DNM1 and VAMP2, respectively. The person skilled in the art is familiar with guidelines used to design peptides having sufficient immunogenicity, for example those described in Jackson, D. C., Fitzmaurice, C. J., Brown, L. E., Zeng, W. (1999), Preparation and properties of totally synthetic immunogens, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173. Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) is has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71. If the polypeptide is STX1B or a variant thereof, the epitope is preferably in SEQ ID NO: 5.

The inventive polypeptide, which comprises a polypeptide selected from the group comprising NSF, STX1B, DNM1 and VAMP2 or a variant thereof, when used according to the present invention, may be provided in any kind of conformation. For example, the polypeptide may be an essentially unfolded, a partially or a fully folded polypeptide. In a preferred embodiment, the polypeptide is folded in the sense that the epitopes essential for the binding to the inventive autoantibody, or the protein or variant thereof in its entirety, adopt the fold adopted by the native protein in its natural environment. The person skilled in the art is familiar with methods suitable to determine whether or not a polypeptide is folded and if it is, which structure it has, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably CD spectroscopy is used.

The inventive polypeptide may be a fusion protein which comprises amino acid sequences other than those taken from NSF, STX1B, DNM1 and VAMP2, in particular a C-terminal or N-terminal tag, preferably a C-terminal tag, which is, in a preferred embodiment, as used herein, an additional sequence motif or polypeptide having a function that has some biological or physical function and may, for example, be used to purify, immobilize, precipitate or identify the inventive polypeptide. In a more preferred embodiment, the tag is a sequence or domain capable of binding specifically to a ligand, for example a tag selected from the group comprising His tags, thioredoxin, maltose binding protein, glutathione-S-transferase, a fluorescence tag, for example from the group comprising green fluorescent protein.

The inventive polypeptide may be an immobilized polypeptide. In a preferred embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Various suitable carriers, for example paper, polystyrene, metal, silicon or glass surfaces, microfluidic channels, membranes, beads such as magnetic beads, column chromatography media, biochips, polyacrylamide gels and the like have been described in the literature, for example in Kim, D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, and A. E. (2013), Protein immobilizsation techniques for microfluidic assays, Biomicrofluidics 7(4), 041501. In addition, various reagents and kits for immobilization reactions are commercially available, for example from Pierce Biotechnology.

It is essential that the sample used for the diagnosis in line with the detection of autoantibodies according to the present invention comprises antibodies, also referred to as immunoglobulins. Typically the sample of a bodily fluid comprises a representative set of the entirety of the subject's immunoglobulins. However, the sample, once provided, may be subjected to further processing which may include fractionation, centrifugation, enriching or isolating the entirety of immunoglobulins or any immunoglobulin class of the subject, which may affect the relative distribution of immunoglobulins of the various classes.

The reagents, devices, methods and uses described throughout this application may be used for the diagnosis of a disease. In a preferred embodiment, the disease is a neurological disease. In a more preferred embodiment, the term "neurological disease", as used herein, refers to any disease associated with a defect of the nervous system, in another preferred embodiment, the term "PNS", abbreviation of paraneoplastic neurological syndrome, as used herein, refers to a systemic disorder indirectly caused by the presence of a tumor, for example, as a result of the production release of substances such as hormones or cytokines not normally produced by the cell of origin of the tumor or are produced at increased concentration or the production and release of biologically active cells. The tumor may be too small for detection.

In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from certain a disease or disorder in the past, at the time of the diagnosis or in the future, to find out how the disease is progressing or is likely to progress in the future or to evaluate the responsiveness of a patient with regard to a certain treatment, for example the administration of immunosuppressive drugs. In other words, the term "diagnosis" comprises not only diagnosing, but also prognosticating and/or monitoring the course of a disease or disorder.

In many cases the mere detection, in other words determining whether or not detectable levels of the antibody are present in the sample, is sufficient for the diagnosis. If the autoantibody can be detected, this will be information instrumental for the clinician's diagnosis and indicates an increased likelihood that the patient suffers from a disease. In a preferred embodiment, the autoantibody is deemed detectable if it can be detected using one or more methods selected from the group comprising immunoprecipitation, indirect immunofluorescence, ELISA or line blot, preferably immunoprecipitation. Experimental details are as described in the experimental section of this application or as in text books or practical manuals as available at the priority date of this application. In a preferred embodiment, the relative concentration of the antibody in the serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 0.1, preferably 0.2, 0.5, 1, 2, 5, 10, 20, 25, 50, 100, 200, 500, 1000, 10000 or 100000 times higher than the concentration found in the average healthy subject. In a preferred embodiment, the relative concentration of the autoantibody is determined using one or more methods selected from the group comprising semi-quantitative immunoprecipitation, semi-quantitative semi-quantitative indirect immunofluorescence, ELISA or semi-quantitative line blot, preferably ELISA. Experimental details are as described in the experimental section of this application or as in text books or practical manuals as available at the priority date of this application.

The person skilled in the art will appreciate that a clinician does usually not conclude whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other non-invasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. In a preferred embodiment, the meaning of any symptoms or diseases referred to throughout this application is in line with the person skilled in the art's understanding as of the filing date or, preferably, earliest priority date of this application as evidenced by text books and scientific publications.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i. e. a systematic diagnostic procedure considering the likelihood of a range of possible conditions on the basis of a range of diagnostic parameters. Consequently, the inventive method, polypeptide or use, optionally for determining whether a patient suffers from the a disease, may comprise obtaining a sample from a patient, preferably a human patient, determining whether an autoantibody binding to a polypeptide selected from the group comprising NSF, STX1B, DNM1 and VAMP2 is present in said sample, wherein said determining is performed by contacting the sample with the inventive polypeptide and detecting whether binding occurs between said polypeptide and said autoantibody, preferably using a labeled secondary antibody, wherein said autoantibody binds to said polypeptide if present in the sample, and diagnosing the patient as suffering or being more likely to suffer from said neurological disorder if the autoantibody was determined to be present in the sample.

In a preferred embodiment, the method according to the present invention comprises detecting more than one autoantibody from the group comprising an autoantibody to each of the polypeptides NSF, STX1B, DNM1, VAMP2, GAD65, GAD67, IA-2, ZNT8 and amphiphysin. In a more preferred embodiment, this may involve a) detecting an autoantibody from the group comprising an autoantibody to each of the polypeptides GAD65, GAD67, IA-2, ZNT8 and amphiphysin, preferably GAD65 and GAD67 and b) detecting an autoantibody from the group comprising an autoantibody to each of the polypeptides NSF, STX1B, DNM1, VAMP2, preferably NSF.

The term "diagnosis" may also refer to a method or agent used to distinguish between two or more conditions associated with similar or identical symptoms.

The term "diagnosis" may also refer to a method or agent used to choose the most promising treatment regime for a patient. In other words, the method or agent may relate to selecting a treatment regimen for a subject. For example, the detection of autoantibodies may indicate that an immunosuppressive therapy is to be selected, which may include administrating to the patient one or more immunosuppressive drugs.

The present invention relates to a complex comprising an antibody, preferably autoantibody, binding to the inventive polypeptide. Such a complex may be used or detected as part of a method for diagnosing a disease. A liquid sample comprising antibodies from a subject may be used to practice the method if autoantibodies to a polypeptide selected from the group comprising NSF, STX1B, DNM1 and VAMP2 are to be detected. Such a liquid sample may be any bodily fluid comprising a representative set of antibodies from the subject, preferably a sample comprising antibodies of the IgG immunoglobulin class from the subject. For example, a sample may be cerebrospinal fluid (CSF), blood or blood serum, lymph, insterstitial fluid and is preferably serum or CSF, more preferably serum.

The step contacting a liquid sample comprising antibodies with the inventive polypeptide(s) may be carried out by incubating an immobilized form of said polypeptide(s) in the presence of the sample comprising antibodies under conditions that are compatible with the formation of the complex comprising the respective polypeptide and an antibody, preferably an autoantibody, binding to the inventive polypeptide. The liquid sample, then depleted of antibodies binding to the inventive polypeptide(s) may be removed subsequently, followed by one or more washing steps. Finally the complex comprising the antibody or antibodies and the polypeptide(s) may be detected. In a preferred embodiment, the term "conditions compatible with the formation of the complex" are conditions that allow for the specific antigen-antibody interactions to build up the complex comprising the polypeptide an the antibody. In a preferred embodiment such conditions may comprise incubating the polypeptide in sample diluted 1:100 in PBS buffer for 30 minutes at 25° C. In a preferred embodiment, the term "autoantibody", as used herein, refers to an antibody binding specifically to an endogenous molecule of the animal, preferably mammal, which produces said autoantibody, wherein the level of such antibody is more preferably elevated compared to the average healthy person or person not suffering from the disease, preferably healthy person. In a most preferred embodiment, the autoantibody is an autoantibody binding to a polypeptide selected from the group comprising NSF, STX1B, DNM1 and VAMP2.

The method according to the present invention is preferably an in vitro method.

In a preferred embodiment, the detection of the complex for the prognosis, diagnosis, methods or test kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, preferably ELISA, chemiluminscence immunoassays, and immunofluorescence, preferably indirect immunofluorescence techniques. The person skilled in the art is familiar with these methods, which are also described in the state of the art, for example in Zane, H. D. (2001), Immunology—Theoretical & Practical Concepts in Laboratory Medicine, W. B. Saunders Company, in particular in Chapter 14.

Alternatively, a sample comprising tissue comprising the inventive polypeptide rather than a liquid sample may be used. The tissue sample is preferably from a tissue expressing endogenous polypeptide selected from the group comprising NSF, STX1B, DNM1 and VAMP2, preferably at an increased level compared to the average tissue in the respective organism's, preferably human body. Such a sample, which may be in the form of a tissue section fixed on a carrier, for example a glass slide for microscopic analysis, may then be contacted with the inventive antibody, preferably autoantibody, binding to the inventive polypeptide. The antibody is preferably labeled to allow for distinction from endogenous antibodies binding to the inventive polypeptide, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and the inventive polypeptide may be correlated with reference data. For example, detection of said complex indicates that the patient who provided the sample analyzed has suffered, is suffering or is likely to suffer in the future from a disease. If a patient has been previously diagnosed and the method for obtaining diagnostically relevant information is run again, the amount of complex detected in both runs may be correlated to find out about the progression of the disease and/or the success of a treatment. For example, if the amount of complex is found to increase, this suggests that the disorder is progressing, likely to manifest in the future and/or that any treatment attempted is unsuccessful.

In a preferred embodiment, a microtiterplate, membrane, blot such as dot blot or line blot is used to carry out the diagnostic method according to the invention. The person skilled in the art is familiar with the experimental setup, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540).

In another preferred embodiment, the prognosis, diagnosis, methods or test kit in line with the inventive teachings contemplate the use of indirect immunofluorescence. The person skilled in the art is familiar with such techniques and the preparation of suitable samples, which are described in the state of the art (U.S. Pat. No. 4,647,543; Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007). Suitable reagents, devices and software packages are commercially available, for example from EUROIMMUN, Lübeck, Germany.

A sample may be subjected to a test to determine only whether an autoantibody binding to polypeptide selected from the group comprising NSF, STX1B, DNM1 and VAMP2 is present, but it is preferred that diagnostic methods, tests, devices and the like contemplate determining the presence of autoantibodies to one or more additional polypeptides, preferably related to neurological autoimmune diseases, preferably selected from the group comprising Hu, Yo, Ri, CV2, PNMA1, PNMA2, DNER/Tr, ARHGAP26, ITPR1, ATP1A3, NBC1, Neurochrondrin, CARPVIII, Zic4, Sox1, Ma, MAG, MP0, MBP, GAD65, amphiphysin, recoverin, GABA A receptor (EP13189172.3), GABA B receptor (EP2483417), glycine receptor, gephyrin, IgLON5 (2016/0349275), DPPX (US2015/0247847), aquaporin-4, MOG, NMDA receptor, AMPA receptors, GRM1, GRM5, LGI1, VGCC and mGluR1 and CASPR2, which antigens are preferably immobilized, for example on a medical device such as a line blot. In a more preferred embodiment, an autoantibody to a polypeptide selected from the group comprising NSF, STX1B, DNM1 and VAMP2, and an autoantibody to GAD65 is detected. The diagnostically relevant markers Neurochrondrin (EP15001186), ITPR1 (EP14003703.7), NBC1 (EP14003958.7), ATP1A3, also referred to as alpha 3 subunit of human neuronal Na(+)/K(+) ATPase (EP14171561.5), Flotillin1/2 (EP3101424) and RGS8 (EP17000666.2), autoantibodies to one or more of which may be detected in addition, have been described in the state of the art.

According to the teachings of the present invention, an antibody, preferably an autoantibody binding to the inventive polypeptide used for the diagnosis of a disease is provided. The person skilled in the art is familiar with methods for purifying antibodies, for example those described in Hermanson, G. T., Mallia, A. K., and Smith, P. K. (1992), Immobilized Affinity Ligand Techniques, San Diego: Academic Press. Briefly, an antigen binding specifically to the antibody of interest, which antigen is the inventive polypeptide, is immobilized and used to purify, via affinity chromatography, the antibody of interest from an adequate source. A liquid sample comprising antibodies from a patient suffering from the ndisease may be used as the source.

According to the invention, an antibody, for example an autoantibody, is provided that is capable of binding specifically to the inventive polypeptide. In a preferred embodiment, the term "antibody", as used herein, refers to any immunoglobulin-based binding moieties, more preferably one comprising at least one immunoglobulin heavy chain and one immunoglobulin light chain, including, but not limited to monoclonal and polyclonal antibodies as well as variants of an antibody, in particular fragments, which binding moieties are capable of binding to the respective antigen, more preferably binding specifically to it. In a preferred embodiment, the term "binding specifically", as used herein, means that the binding is stronger than a binding reaction characterized by a dissociation constant of $1 \times 10^{-5}$ M, more preferably $1 \times 10^{-7}$ M, more preferably $1 \times 10^{-8}$ M, more preferably $1 \times 10^{-9}$ M, more preferably $1 \times 10^{-10}$ M, more preferably $1 \times 10^{-11}$ M, more preferably $1 \times 10^{-12}$ M, as determined by surface plasmon resonance using Biacore equipment at 25° C. in PBS buffer at pH 7. The antibody may be part of an autoantibody preparation which is heterogeneous or may be a homogenous autoantibody, wherein a heterogeneous preparation comprises a plurality of different autoantibody species as obtainable by preparation from the sera of human donors, for example by affinity chromatography using the immobilized antigen to purify any autoantibody capable of binding to said antigen. The antibody may be glycosylated or non-glycosylated. The person skilled in the art is familiar with methods that may be used for the identification, production and purification of antibodies and variants thereof, for examples those described in EP 2 423 226 A2 and references therein. The antibody may be used as a diagnostic agent, by itself, or in combination, for example in complex with the inventive polypeptide.

The present invention provides a method for isolating an antibody, preferably an autoantibody, binding to the inventive polypeptide, comprising the steps a) contacting a sample comprising the antibody with the inventive polypeptide such that a complex is formed, b) isolating the complex formed in step a), c) dissociating the complex isolated in step b), and d) separating the antibody from the inventive polypeptide. A sample from a patient suffering from the novel neurological disorder identified by the inventors may be used as the source of antibody. Suitable methods are described in the state of the art, for example in the Handbooks "Affinity chromatography", "Strategies for Protein Purification" and "Antibody Purification" (2009/2010), published by GE Healthcare Life Sciences, and in in Philips, Terry, M., Analytical techniques in immunochemistry, 1992, Marcel Dekker, Inc.

The invention provides a pharmaceutical composition comprising the inventive polypeptide, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject. In a preferred embodiment, the invention provides a vaccine comprising the inventive polypeptide, optionally comprising an auxiliary agent such as an adjuvants or a buffer, and the use of the inventive polypeptide for the preparation of a vaccine.

Within the scope of the present invention, a medical or diagnostic device comprising, preferably coated with a reagent for detecting the inventive (auto)antibody and/or the inventive polypeptide is provided. Preferably such a medical or diagnostic device comprises the inventive polypeptide in a form that allows contacting it with an aqueous solution, more preferably the liquid human sample, in a straightforward manner. In particular, the inventive polypeptide comprising may be immobilized on the surface of a carrier, preferably selected from the group comprising glass plates or slides, biochips, microtiter plates, beads, for example magnetic beads, apharesis devices, chromatography columns, membranes or the like. Exemplary medical devices include line blots, microtiter plates, glass slides for microscopy, beads, preferably magnetic beads, and biochips. In addition to the inventive polypeptide, the medical or diagnostic device may comprise additional polypeptides, for example positive or negative controls such as samples comprising or not comprising an antibody binding to the polypeptide of interest, or known other antigens binding to autoantibodies of diagnostic value, particularly those related other diseases associated with one or more identical or similar symptoms.

The inventive teachings provide a kit, preferably for diagnosing a disease. Such a kit may comprise instructions detailing how to use the kit and a means for contacting the inventive polypeptide with a bodily fluid sample from a subject, preferably a human subject, for example a line blot, wherein the inventive polypeptide is immobilized on the line blot. Furthermore, the kit may comprise a positive control, for example a batch of autoantibody or recombinant antibody known to bind to the polypeptide according to the present invention and a negative control, for example a protein having no detectable affinity to the inventive polypeptide such as bovine serum albumin. Finally, such a kit may comprise a standard solution of the antibody or antigen for preparing a calibration curve.

In a preferred embodiment, the kit comprises a means for detecting an autoantibody binding to the inventive polypeptide, preferably by detecting a complex comprising the inventive polypeptide and an antibody binding to the inventive polypeptide. Such means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, preferably a secondary antibody specific for mammalian IgG class of antibodies. A multitude of methods and means for detecting such a complex have been described in the state of the art, for example in Philips, Terry, M., Analytical techniques in immunochemistry, 1992, Marcel Dekker, Inc.

The polypeptides according to the present invention, comprising a polypeptide selected from the group comprising NSF, STX1B, DNM1 and VAMP2, or a variant thereof may be produced or provided in the form of a cell comprising and/or expressing a nucleic acid encoding said polypeptide. If a nucleic acid comprising a sequence that encodes for the inventive polypeptide or variant thereof is used, such a nucleic acid may be an unmodified nucleic acid. In a preferred embodiment, the nucleic acid is a nucleic acid that, as such, does not occur in nature and comprises, compared to natural nucleic acid, at least one modification, for example an isotopic content or chemical modifications, for example a methylation, sequence modification, label or the like indicative of synthetic origin. In a preferred embodiment, the nucleic acid is a recombinant nucleic acid, and is, in a more preferred embodiment, part of a vector, in which it may be functionally linked with a promoter that allows for expression, preferably overexpression of the nucleic acid. The person skilled in the art is familiar with a variety of suitable vectors, of which are commercially available, for example from Origene. For example, a vector encoding for fusion constructs with a C-terminal GFP may be used. The cell may be a eukaryotic or prokaryotic cell, preferably of eukaryotic cell, such as a yeast cell, and is more preferably a mammalian, more preferably a human cell such as a HEK293 cell. Examples of a mammalian cell include a HEK293, CHO or COS-7 cell. The cell comprising the nucleic acid encoding for the inventive polypeptide may be a recombinant cell or an isolated cell wherein the term "isolated" means that the cell is enriched such that, compared to the environment of the wild type of said cell, fewer cells of other differentiation or species or in fact no such other cells are present.

The inventive teachings may not only be used for a diagnosis, but also for preventing or treating a disease, more specifically a method for preventing or treating a disease, comprising the steps a) reducing the concentration of autoantibodies binding to the inventive polypeptide in the subject's blood and/or b) administering one or more immunosuppressive pharmaceutical substances, preferably selected from the group comprising rituximab, prednisone, methylprednisolone, cyclophosphamide, mycophenolate-mofetil, intravenous immunoglobulin, tacrolimus, cyclosporine, methotrexate, azathioprine and/or the pharmaceutical composition.

In a preferred embodiment, the present invention provides a use of a means for the detection of an autoantibody to a polypeptide selected from the group comprising NSF, STX1B, DNM1 and VAMP2, or of a nucleic acid encoding NSF, STX1B, DNM1 or VAMP2 or the variant or a vector or cell comprising said nucleic acid for the manufacture of kit for the diagnosis of a disease such as stiff-person syndrome. In another preferred embodiment, the present invention provides a use of a reagent for the detection of an autoantibody to a polypeptide selected from the group comprising NSF, STX1B, DNM1 and VAMP2, or of a nucleic acid encoding NSF, STX1B, DNM1 or VAMP2 or the variant or a vector or cell comprising said nucleic acid for the manufacture of kit for the diagnosis of a disease such as stiff-person syndrome.

In a preferred embodiment, any method or use according to the present invention may be intended for a non-diagnostic use, i.e. determining the presence of an autoantibody to a polypeptide selected from the group comprising NSF, STX1B, DNM1 and VAMP2 for a use other than diagnosing a patient. For example, the method or use may be for testing in vitro the efficiency of a medical device designed to remove an autoantibody from a patient's blood, wherein the testing is performed on a liquid other than patient's blood. In a preferred embodiment, any method or use according to the present invention may be intended for generating an autoantibody profile, preferably for detecting a disease in a mammal, preferably a human. In a preferred embodiment, any method or use may be for detecting disease-associated markers in a sample from neurological disease patients.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2B shows Immunoprecipitation and antigen identification. Lysates of rat cerebellum were incubated with patient or control sera. Immunocomplexes were isolated with protein-G-coated magnetic beads, eluted by SDS and subjected to SDS-PAGE analysis followed by (FIG. 2A) staining with colloidal coomassie or (FIG. 2B) Western blot and incubation with anti-STX1B mouse antibody. Arrow indicates the position of the immunoprecipitated antigen at about 33 kDa.

FIGS. 3A-3C shows the verification of STX1B as the novel autoantigen by indirect immunofluorescence and Western blot with the recombinant antigen. (FIG. 3A) Indirect immunofluorescence using acetone-fixed STX1B or mock-transfected HEK293 cells incubated with patient CSF (1:1) or sera (1:10) or a healthy control serum (1:10). (FIG. 3B) Western blot with STX1B(ic)-His incubated with anti-His, patient sera (1:200) or healthy control sera (1:200). (FIG. 3C) Neutralization of immunofluorescence reaction on neuronal tissues. Patient serum was pre-incubated with extracts of HEK293 cells transfected with STX1B or with empty vector as control. The extract containing STX1B abolished the immune reaction.

(FIG. 4C) Western blot with STX1B(ic)-His incubated with patient sera (1:200) or healthy control sera (1:200).

FIGS. 6A-6B shows the verification of VAMP2 as the novel autoantigen by indirect immunofluorescence with the recombinant antigen. Indirect immunofluorescence using (FIG. 6A) cryosections incubated with patient serum (1:32) or (FIG. 6B) acetone-fixed VAMP2 or mock-transfected HEK293 cells incubated with patient or a healthy control serum (1:10) in the first step, and with Alexa488-labelled goat anti-human IgG in the second step.

Figure 1:
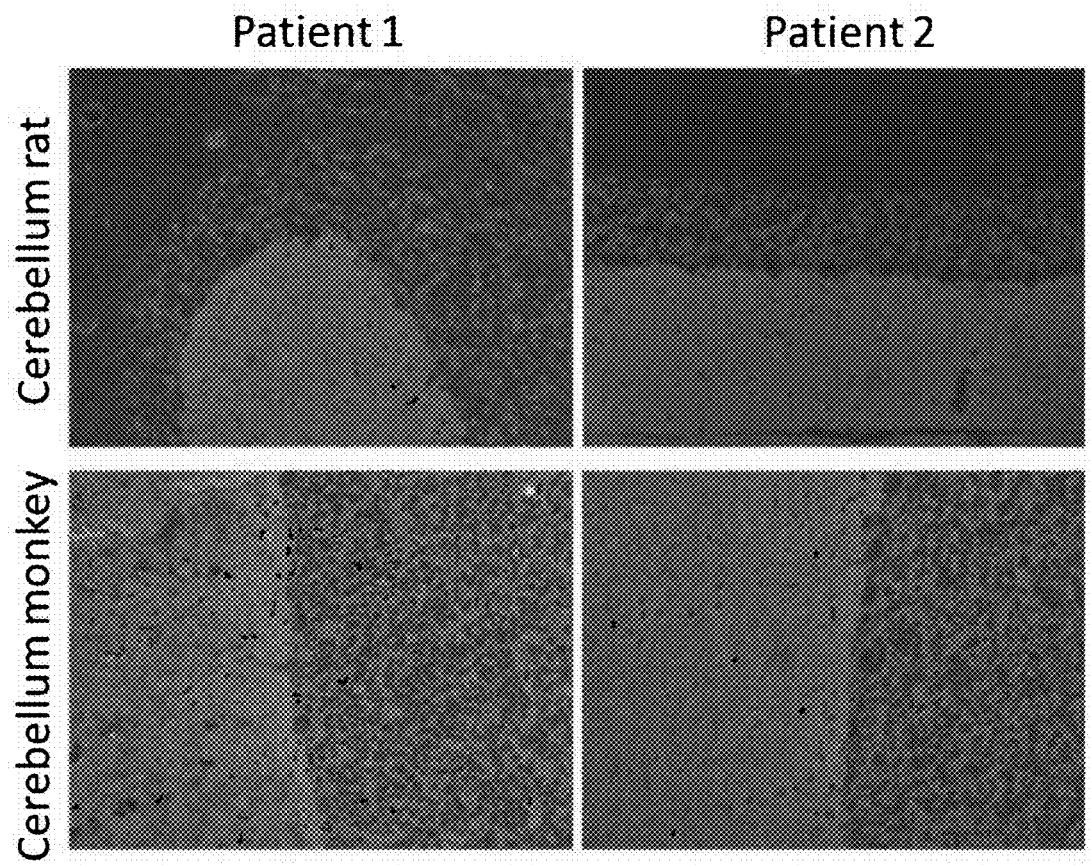
FIG. 1 shows immunofluorescence staining of cerebellum. Cryosections were incubated with patient sera (P1 1:32; P2 1:100) in the first step, and with Alexa488-labelled goat anti-human IgG in the second step. A smooth staining of cerebellar molecular layer and granular layer was obtained with the strongest reaction on the molecular layer.

The present invention comprises a range of sequences, more specifically

```
(NSF, UNIPROT)
                                                      SEQ ID NO: 1
MAGRSMQAARCPTDELSLTNCAVVNEKDFQSGQHVIVRTSPNHRYTFTLKTHPSVVPG

SIAFSLPQRKWAGLSIGQEIEVSLYTFDKAKQCIGTMTIEIDFLQKKSIDSNPYDTDKMAA

EFIQQFNNQAFSVGQQLVFSFNEKLFGLLVKDIEAMDPSILKGEPATGKRQKIEVGLVVG

NSQVAFEKAENSSLNLIGKAKTKENRQSIINPDWNFEKMGIGGLDKEFSDIFRRAFASRV

FPPEIVEQMGCKHVKGILLYGPPGCGKTLLARQIGKMLNAREPKVVNGPEILNKYVGES

EANIRKLFADAEEEQRRLGANSGLHIIIFDEIDAICKQRGSMAGSTGVHDTVVNQLLSKID

GVEQLNNILVIGMTNRPDLIDEALLRPGRLEVKMEIGLPDEKGRLQILHIHTARMRGHQL

LSADVDIKELAVETKNFSGAELEGLVRAAQSTAMNRHIKASTKVEVDMEKAESLQVTR

GDFLASLENDIKPAFGTNQEDYASYIMNGIIKWGDPVTRVLDDGELLVQQTKNSDRTPL

VSVLLEGPPHSGKTALAAKIAEESNFPFIKICSPDKMIGFSETAKCQAMKKIFDDAYKSQL

SCVVVDDIERLLDYVPIGPRFSNLVLQALLVLLKKAPPQGRKLLIIGTTSRKDVLQEMEM

LNAFSTTIHVPNIATGEQLLEALELLGNFKDKERTTIAQQVKGKKVWIGIKKLLMLIEMS

LQMDPEYRVRKFLALLREEGASPLDFD (NSF, REC)
                                                      SEQ ID NO: 2
MAGRSMQAARCPTDELSLTNCAVVNEKDFQSGQHVIVRTSPNHRYTFTLKTHPSVVPG

SIAFSLPQRKWAGLSIGQEIEVSLYTFDKAKQCIGTMTIEIDFLQKKSIDSNPYDTDKMAA

EFIQQFNNQAFSVGQQLVFSFNEKLFGLLVKDIEAMDPSILKGEPATGKRQKIEVGLVVG
```

-continued

NSQVAFEKAENSSLNLIGKAKTKENRQSIINPDWNFEKMGIGGLDKEFSDIFRRAFASRV

FPPEIVEQMGCKHVKGILLYGPPGCGKTLLARQIGKMLNAREPKVVNGPEILNKYVGES

EANIRKLFADAEEEQRRLGANSGLHIIIFDEIDAICKQRGSMAGSTGVHDTVVNQLLSKID

GVEQLNNILVIGMTNRPDLIDEALLRPGRLEVKMEIGLPDEKGRLQILHIHTARMRGHQL

LSADVDIKELAVETKNFSGAELEGLVRAAQSTAMNRHIKASTKVEVDMEKAESLQVTR

GDFLASLENDIKPAFGTNQEDYASYIMNGIIKWGDPVTRVLDDGELLVQQTKNSDRTPL

VSVLLEGPPHSGKTALAAKIAEESNFPFIKICSPDKMIGFSETAKCQAMKKIFDDAYKSQL

SCVVVDDIERLLDYVPIGPRFSNLVLQALLVLLKKAPPQGRKLLIIGTTSRKDVLQEMEM

LNAFSTTIHVPNIATGEQLLEALELLGNFKDKERTTIAQQVKGKKVWIGIKKLLMLIEMS

LQMDPEYRVRKFLALLREEGASPLDFD (STX1B, UNIPROT)
SEQ ID NO: 3
MKDRTQELRSAKDSDDEEEVVHVDRDHFMDEFFEQVEEIRGCIEKLSEDVEQVKKQHS

AILAAPNPDEKTKQELEDLTADIKKTANKVRSKLKAIEQSIEQEEGLNRSSADLRIRKTQH

STLSRKFVEVMTEYNATQSKYRDRCKDRIQRQLEITGRTTTNEELEDMLESGKLAIFTDD

IKMDSQMTKQALNEIETRHNEIIKLETSIRELHDMFVDMAMLVESQGEMIDRIEYNVEHS

VDYVERAVSDTKKAVKYQSKARRKKIMIIICCVVLGVVLASSIGGTLGL (STX1B, REC)
SEQ ID NO: 4
MKDRTQELRSAKDSDDEEEVVHVDRDHFMDEFFEQVEEIRGCIEKLSEDVEQVKKQHS

AILAAPNPDEKTKQELEDLTADIKKTANKVRSKLKAIEQSIEQEEGLNRSSADLRIRKTQH

STLSRKFVEVMTEYNATQSKYRDRCKDRIQRQLEITGRTTTNEELEDMLESGKLAIFTDD

IKMDSQMTKQALNEIETRHNEIIKLETSIRELHDMFVDMAMLVESQGEMIDRIEYNVEHS

VDYVERAVSDTKKAVKYQSKARRKKIMIIICCVVLGVVLASSIGGTLGL (STX1B(ic)-His, REC)
SEQ ID NO: 5
MKDRTQELRSAKDSDDEEEVVHVDRDHFMDEFFEQVEEIRGCIEKLSEDVEQVKKQHS

AILAAPNPDEKTKQELEDLTADIKKTANKVRSKLKAIEQSIEQEEGLNRSSADLRIRKTQH

STLSRKFVEVMTEYNATQSKYRDRCKDRIQRQLEITGRTTTNEELEDMLESGKLAIFTDD

IKMDSQMTKQALNEIETRHNEIIKLETSIRELHDMFVDMAMLVESQGEMIDRIEYNVEHS

VDYVERAVSDTKKAVKYQSKARRKKLEHHHHHHHH (VAMP2, UNIPROT)
SEQ ID NO: 6
MSATAATAPPAAPAGEGGPPAPPPNLTSNRRLQQTQAQVDEVVDIMRVNVDKVLERDQ

KLSELDDRADALQAGASQFETSAAKLRKYWWKNLKMMIILGVICAIILIIIVYFST (VAMP2, REC)
SEQ ID NO: 7
MSATAATAPPAAPAGEGGPPAPPPNLTSNRRLQQTQAQVDEVVDIMRVNVDKVLERDQ

KLSELDDRADALQAGASQFETSAAKLRKYWWKNLKMMIILGVICAIILIIIVYFST (sense NSF)
SEQ ID NO: 8
ATACGTCTCACATGGCGGGCCGGAGCATGCAAG (asense NSF)
SEQ ID NO: 9
TATCGTCTCCTCGATCAATCAAAATCAAGGGGGCTAG (sense STX1B)
SEQ ID NO: 10
ATACGTCTCACATGAAGGATCGGACTCAAGAGCTGC -continued (asense STX1B)
SEQ ID NO: 11
ATACGTCTCCTCGAGCTACAAGCCCAGCGTCCCCCCAATG (asense STX1B(ic)-His)
SEQ ID NO: 12
ATACGTCTCCTCGAGTTTCTTCCTCCGGGCCTTGCTCTG (sense VAMP2)
SEQ ID NO: 13
ATACGTCTCTCATGTCTGCTACCGCTGCCACGGCCC (asense VAMP2)
SEQ ID NO: 14
ATACGTCTCCTCGAGTTAAGTGCTGAAGTAAACTATGATG (pTriEx-1-NSF)
SEQ ID NO: 15
TAATACGACTCACTATAGGGGAATTGTGAGCGGATAACAATTCCCCGGAGTTAATCC

GGGACCTTTAATTCAACCCAACACAATATATTATAGTTAAATAAGAATTATTATCAA

ATCATTTGTATATTAATTAAAATACTATACTGTAAATTACATTTTATTTACAATCAAA

GGAGATATACCATGGCGGGCCGGAGCATGCAAGCGGCAAGATGTCCTACAGATGAA

TTATCTTTAACCAATTGTGCAGTTGTGAATGAAAAGGATTTCCAGTCTGGCCAGCAT

GTGATTGTGAGGACCTCTCCCAATCACAGGTACACATTTACACTGAAGCACATCCA

TCGGTGGTTCCAGGGAGCATTGCATTCAGTTTACCTCAGAGAAAATGGGCTGGGCTT

TCTATTGGGCAAGAAATAGAAGTCTCCTTATATACATTTGACAAAGCCAAACAGTGT

ATTGGCACAATGACCATCGAGATTGATTTCCTGCAGAAAAAAAGCATTGACTCCAAC

CCTTATGACACCGACAAGATGGCAGCAGAATTTATTCAGCAATTCAACAACCAGGC

CTTCTCAGTGGGACAACAGCTTGTCTTTAGCTTCAATGAAAAGCTTTTTGGCTTACTG

GTGAAGGACATTGAAGCCATGGATCCTAGCATCCTGAAGGGAGAGCCTGCGACAGG

GAAAAGGCAGAAGATTGAAGTAGGACTGGTTGTTGGAAACAGTCAAGTTGCATTTG

AAAAAGCAGAAAATTCGTCACTTAATCTTATTGGCAAAGCTAAAACCAAGGAAAAT

CGCCAATCAATTATCAATCCTGACTGGAACTTTGAAAAAATGGGAATAGGAGGTCT

AGACAAGGAATTTTCAGATATTTTCCGACGAGCATTTGCTTCCCGAGTATTTCCTCCA

GAGATTGTGGAGCAGATGGGTTGTAAACATGTTAAAGGCATCCTGTTATATGGACCC

CCAGGTTGTGGTAAGACTCTCTTGGCTCGACAGATTGGCAAGATGTTGAATGCAAGA

GAGCCCAAAGTGGTCAATGGGCCAGAAATCCTTAACAAATATGTGGGAGAATCAGA

GGCTAACATTCGCAAACTTTTTGCTGATGCTGAAGAGGAGCAAAGGAGGCTTGGTG

CTAACAGTGGTTTGCACATCATCATCTTTGATGAAATTGATGCCATCTGCAAGCAGA

GAGGGAGCATGGCTGGTAGCACGGGAGTTCATGACACTGTTGTCAACCAGTTGCTGT

CCAAAATTGATGGCGTGGAGCAGCTAAACAACATCCTAGTCATTGGAATGACCAAT

AGACCAGATCTGATAGATGAGGCTCTTCTTAGACCTGGAAGACTGGAAGTTAAAAT

GGAGATAGGCTTGCCAGATGAGAAAGGCCGACTACAGATTCTTCACATCCACACAG

CAAGAATGAGAGGGCATCAGTTACTCTCTGCTGATGTAGACATTAAAGAACTGGCC

GTGGAGACCAAGAATTTCAGTGGTGCTGAATTGGAGGGTCTAGTGCGAGCAGCCCA

GTCCACTGCTATGAATAGACACATAAAGGCCAGTACTAAAGTGGAAGTGGACATGG

AGAAAGCAGAAAGCCTGCAAGTGACGAGAGGAGACTTCCTTGCTTCTTTGGAGAAT

GATATCAAACCAGCCTTTGGCACAAACCAAGAAGATTATGCAAGTTACATTATGAA

CGGTATCATCAAATGGGGTGACCCAGTTACTCGAGTTCTAGATGATGGGGAGCTGCT

GGTGCAGCAGACTAAGAACAGTGACCGCACACCATTGGTCAGCGTGCTTCTGGAAG

-continued

```
GCCCTCCTCACAGTGGGAAGACTGCTTTAGCTGCAAAAATTGCAGAGGAATCCAACT
TCCCATTCATCAAGATCTGTTCTCCTGATAAAATGATTGGCTTTTCTGAAACAGCCAA
ATGTCAGGCCATGAAGAAGATCTTTGATGATGCGTACAAATCCCAGCTCAGTTGTGT
GGTTGTGGATGACATTGAGAGATTGCTTGATTACGTCCCTATTGGCCCTCGATTTTCA
AATCTTGTATTACAGGCTCTTCTCGTTTTACTGAAAAAGGCACCTCCTCAGGGCCGC
AAGCTTCTTATCATTGGGACCACTAGCCGCAAAGATGTCCTTCAGGAGATGGAAATG
CTTAACGCTTTCAGCACCACCATCCACGTGCCCAACATTGCCACAGGAGAGCAGCTG
TTGGAAGCTTTGGAGCTTTTGGGCAACTTCAAGGATAAGGAACGCACCACAATTGCA
CAGCAAGTCAAAGGGAAGAAGGTCTGGATAGGAATCAAGAAGTTACTAATGCTGAT
CGAGATGTCCCTACAGATGGATCCTGAATACCGTGTGAGAAAATTCTTGGCCCTCTT
AAGAGAAGAAGGAGCTAGCCCCCTTGATTTTGATTGATCGAGCACCACCATCACCAT
CACCATCACTAAGTGATTAACCTCAGGTGCAGGCTGCCTATCAGAAGGTGGTGGCTG
GTGTGGCCAATGCCCTGGCTCACAAATACCACTGAGATCGATCTTTTTCCCTCTGCC
AAAAATTATGGGGACATCATGAAGCCCCTTGAGCATCTGACTTCTGGCTAATAAAGG
AAATTTATTTTCATTGCAATAGTGTGTTGGAATTTTTTGTGTCTCTCACTCGGAAGGA
CATATGGGAGGGCAAATCATTTAAAACATCAGAATGAGTATTTGGTTTAGAGTTTGG
CAACATATGCCCATATGTAACTAGCATAACCCCTTGGGGCCTCTAAACGGGTCTTGA
GGGGTTTTTGCTGAAAGCATGCGGAGGAAATTCTCCTTGAAGTTTCCCTGGTGTTC
AAAGTAAAGGAGTTTGCACCAGACGCACCTCTGTTCACTGGTCCGGCGTATTAAAAC
ACGATACATTGTTATTAGTACATTTATTAAGCGCTAGATTCTGTGCGTTGTTGATTTA
CAGACAATTGTTGTACGTATTTTAATAATTCATTAAATTTATAATCTTTAGGGTGGTA
TGTTAGAGCGAAAATCAAATGATTTTCAGCGTCTTTATATCTGAATTTAAATATTAA
ATCCTCAATAGATTTGTAAAATAGGTTTCGATTAGTTTCAAACAAGGGTTGTTTTTCC
GAACCGATGGCTGGACTATCTAATGGATTTTCGCTCAACGCCACAAAACTTGCCAAA
TCTTGTAGCAGCAATCTAGCTTTGTCGATATTCGTTTGTGTTTTGTTTTGTAATAAAG
GTTCGACGTCGTTCAAAATATTATGCGCTTTTGTATTTCTTTCATCACTGTCGTTAGT
GTACAATTGACTCGACGTAAACACGTTAAATAGAGCTTGGACATATTTAACATCGGG
CGTGTTAGCTTTATTAGGCCGATTATCGTCGTCGTCCCAACCCTCGTCGTTAGAAGTT
GCTTCCGAAGACGATTTTGCCATAGCCACACGACGCCTATTAATTGTGTCGGCTAAC
ACGTCCGCGATCAAATTTGTAGTTGAGCTTTTTGGAATTATTTCTGATTGCGGGCGTT
TTTGGGCGGGTTTCAATCTAACTGTGCCCGATTTTAATTCAGACAACACGTTAGAAA
GCGATGGTGCAGGCGGTGGTAACATTTCAGACGGCAAATCTACTAATGGCGGCGGT
GGTGGAGCTGATGATAAATCTACCATCGGTGGAGGCGCAGGCGGGGCTGGCGGCGG
AGGCGGAGGCGGAGGTGGTGGCGGTGATGCAGACGGCGGTTTAGGCTCAAATGTCT
CTTTAGGCAACACAGTCGGCACCTCAACTATTGTACTGGTTTCGGGCGCCGTTTTTG
GTTTGACCGGTCTGAGACGAGTGCGATTTTTTCGTTTCTAATAGCTTCCAACAATTG
TTGTCTGTCGTCTAAAGGTGCAGCGGGTTGAGGTTCCGTCGGCATTGGTGGAGCGGG
CGGCAATTCAGACATCGATGGTGGTGGTGGTGGAGGCGCTGGAATGTTAGGCA
CGGGAGAAGGTGGTGGCGGCGGTGCCGCCGGTATAATTTGTTCTGGTTTAGTTTGTT
CGCGCACGATTGTGGGCACCGGCGCAGGCGCCGCTGGCTGCACAACGGAAGGTCGT
```

-continued

```
CTGCTTCGAGGCAGCGCTTGGGGTGGTGGCAATTCAATATTATAATTGGAATACAAA

TCGTAAAAATCTGCTATAAGCATTGTAATTTCGCTATCGTTTACCGTGCCGATATTTA

ACAACCGCTCAATGTAAGCAATTGTATTGTAAAGAGATTGTCTCAAGCTCGGAACGC

TGCGCTCGGTCGTTCGGCTGCGGCGAGCGGTATCAGCTCACTCAAAGGCGGTAATAC

GGTTATCCACAGAATCAGGGGATAACGCAGGAAAGAACATGTGAGCAAAAGGCCA

GCAAAAGGCCAGGAACCGTAAAAAGGCCGCGTTGCTGGCGTTTTTCCATAGGCTCC

GCCCCCCTGACGAGCATCACAAAAATCGACGCTCAAGTCAGAGGTGGCGAAACCCG

ACAGGACTATAAAGATACCAGGCGTTTCCCCCTGGAAGCTCCCTCGTGCGCTCTCCT

GTTCCGACCCTGCCGCTTACCGGATACCTGTCCGCCTTTCTCCCTTCGGGAAGCGTG

GCGCTTTCTCAATGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTATCCGGTA

ACTATCGTCTTGAGTCCAACCCGGTAAGACACGACTTATCGCCACTGGCAGCAGCCA

CTGGTAACAGGATTAGCAGAGCGAGGTATGTAGGCGGTGCTACAGAGTTCTTGAAG

TGGTGGCCTAACTACGGCTACACTAGAAGGACAGTATTTGGTATCTGCGCTCTGCTG

AAGCCAGTTACCTTCGGAAAAAGAGTTGGTAGCTCTTGATCCGGCAAACAAACCAC

CGCTGGTAGCGGTGGTTTTTTTGTTTGCAAGCAGCAGATTACGCGCAGAAAAAAAGG

ATCTCAAGAAGATCCTTTGTTACCAATGCTTAATCAGTGAGGCACCTATCTCAGCGA

TCTGTCTATTTCGTTCATCCATAGTTGCCTGACTCCCCGTCGTGTAGATAACTACGAT

ACGGGAGGGCTTACCATCTGGCCCCAGTGCTGCAATGATACCGCGAGACCCACGCT

CACCGGCTCCAGATTTATCAGCAATAAACCAGCCAGCCGGAAGGGCCGAGCGCAGA

AGTGGTCCTGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCTACAGGCA

TCGTGGTGTCACGCTCGTCGTTTGGTATGGCTTCATTCAGCTCCGGTTCCCAACGATC

AAGGCGAGTTACATGATCCCCCATGTTGTGCAAAAAAGCGGTTAGCTCCTTCGGTCC

TCCGATCGTTGTCAGAAGTAAGTTGGCCGCAGTGTTATCACTCATGGTTATGGCAGC

ACTGCATAATTCTCTTACTGTCATGCCATCCGTAAGATGCTTTTCTGTGACTGGTGAG

TACTCAACCAAGTCATTCTGAGAATAGTGTATGCGGCGACCGAGTTGCTCTTGCCCG

GCGTCAATACGGGATAATACCGCGCCACATAGCAGAACTTTAAAAGTGCTCATCATT

GGAAAACGTTCTTCGGGGCGAAAACTCTCAAGGATCTTACCGCTGTTGAGATCCAGT

TCGATGTAACCCACTCGTGCACCCAACTGATCTTCAGCATCTTTTACTTTCACCAGCG

TTTCTGGGTGAGCAAAAACAGGAAGGCAAAATGCCGCAAAAAAGGGAATAAGGGC

GACACGGAAATGTTGAATACTCATACTCTTCCTTTTTCAATATTATTGAAGCATTTAT

CAGGGTTATTGTCTCATGTCCGCGCGTTTCCTGCATCTTTTAATCAAATCCCAAGATG

TGTATAAACCACCAAACTGCCAAAAAATGAAAACTGTCGACAAGCTCTGTCCGTTTG

CTGGCAACTGCAAGGGTCTCAATCCTATTTGTAATTATTGAATAATAAAACAATTAT

AAATGTCAAATTTGTTTTTTATTAACGATACAAACCAAACGCAACAAGAACATTTGT

AGTATTATCTATAATTGAAAACGCGTAGTTATAATCGCTGAGGTAATATTTAAAATC

ATTTTCAAATGATTCACAGTTAATTTGCGACAATATAATTTTATTTTCACATAAACTA

GACGCCTTGTCGTCTTCTTCTTCGTATTCCTTCTCTTTTTCATTTTTCTCTTCATAAAA

ATTAACATAGTTATTATCGTATCCATATATGTATCTATCGTATAGAGTAAATTTTTTG

TTGTCATAAATATATATGTCTTTTTTAATGGGGTGTATAGTACCGCTGCGCATAGTTT
```

-continued

```
TTCTGTAATTTACAACAGTGCTATTTTCTGGTAGTTCTTCGGAGTGTGTTGCTTTAAT
TATTAAATTTATATAATCAATGAATTTGGGATCGTCGGTTTTGTACAATATGTTGCCG
GCATAGTACGCAGCTTCTTCTAGTTCAATTACACCATTTTTTAGCAGCACCGGATTAA
CATAACTTTCCAAAATGTTGTACGAACCGTTAAACAAAAACAGTTCACCTCCCTTTT
CTATACTATTGTCTGCGAGCAGTTGTTTGTTGTTAAAAATAACAGCCATTGTAATGA
GACGCACAAACTAATATCACAAACTGGAAATGTCTATCAATATATAGTTGCTCTAGT
TATTAATAGTAATCAATTACGGGGTCATTAGTTCATAGCCCATATATGGAGTTCCGC
GTTACATAACTTACGGTAAATGGCCCGCCTGGCTGACCGCCCAACGACCCCCGCCCA
TTGACGTCAATAATGACGTATGTTCCCATAGTAACGCCAATAGGGACTTTCCATTGA
CGTCAATGGGTGGACTATTTACGGTAAACTGCCCACTTGGCAGTACATCAAGTGTAT
CATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAG
TCATCGCTATTACCATGCATGGTCGAGGTGAGCCCCACGTTCTGCTTCACTCTCCCCA
TCTCCCCCCCCTCCCCACCCCCAATTTTGTATTTATTTATTTTTTAATTATTTTGTGCA
GCGATGGGGGCGGGGGGGGGGGGGGGCGCGCGCCAGGCGGGGCGGGGCGGGGC
GAGGGGCGGGGCGGGGCGAGGCGGAGAGGTGCGGCGGCAGCCAATCAGAGCGGCG
CGCTCCGAAAGTTTCCTTTTATGGCGAGGCGGCGGCGGCGGCGGCCCTATAAAAAG
CGAAGCGCGCGGCGGGCGGGAGTCGCTGCGACGCTGCCTTCGCCCCGTGCCCCGCT
CCGCCGCCGCCTCGCGCCGCCCGCCCCGGCTCTGACTGACCGCGTTACTCCCACAGG
TGAGCGGGCGGGACGGCCCTTCTCCTTCGGGCTGTAATTAGCGCTTGGTTTAATGAC
GGCTTGTTTCTTTTCTGTGGCTGCGTGAAAGCCTTGAGGGGCTCCGGGAGGGCCCTT
TGTGCGGGGGGAGCGGCTCGGGGCTGTCCGCGGGGGGACGGCTGCCTTCGGGGGGG
ACGGGGCAGGGCGGGGTTCGGCTTCTGGCGTGTGACCGGCGGCTCTAGAGCCTCTG
CTAACCATGTTCATGCCTTCTTCTTTTTCCTACAGCTCCTGGGCAACGTGCTGGTTAT
TGTGCTGTCTCATCATTTTGGCAAAGAATTGGATCGGACCGAAAT
(pTriEx-1-STX1B)                                SEQ ID NO: 16
GGAGTCGCTGCGACGCTGCCTTCGCCCCGTGCCCCGCTCCGCCGCCGCCTCGCGCCG
CCCGCCCCGGCTCTGACTGACCGCGTTACTCCCACAGGTGAGCGGGCGGGACGGCC
CTTCTCCTTCGGGCTGTAATTAGCGCTTGGTTTAATGACGGCTTGTTTCTTTTCTGTG
GCTGCGTGAAAGCCTTGAGGGGCTCCGGGAGGGCCCTTTGTGCGGGGGAGCGGCT
CGGGGCTGTCCGCGGGGGACGGCTGCCTTCGGGGGGACGGGGCAGGGCGGGGTT
CGGCTTCTGGCGTGTGACCGGCGGCTCTAGAGCCTCTGCTAACCATGTTCATGCCTT
CTTCTTTTTCCTACAGCTCCTGGGCAACGTGCTGGTTATTGTGCTGTCTCATCATTTTG
GCAAAGAATTGGATCGGACCGAAATTAATACGACTCACTATAGGGGAATTGTGAGC
GGATAACAATTCCCCGGAGTTAATCCGGGACCTTTAATTCAACCCAACACAATATAT
TATAGTTAAATAAGAATTATTATCAAATCATTTGTATATTAATTAAAATACTATACTG
TAAATTACATTTTATTTACAATCAAAGGAGATATACCATGAAGGATCGGACTCAAGA
GCTGCGGAGTGCGAAAGACAGTGATGATGAAGAGGAGGTGGTCCACGTGGATCGGG
ACCACTTCATGGATGAGTTCTTTGAACAGGTGGAAGAGATCCGGGGCTGCATTGAG
AAACTGTCGGAGGATGTGGAGCAGGTGAAAAAACAGCATAGCGCCATCCTGGCCGC
```

-continued

```
ACCCAACCCAGATGAGAAGACCAAACAGGAGCTGGAGGATCTCACTGCAGACATCA

AGAAGACGGCCAACAAGGTTCGGTCCAAATTGAAAGCGATCGAGCAAAGCATTGAA

CAGGAGGAGGGGCTGAACCGTTCCTCCGCGGACCTGCGCATCCGCAAGACCCAGCA

CTCCACACTGTCCCGGAAGTTCGTGGAGGTAATGACCGAATATAACGCGACCCAGT

CCAAGTACCGGGACCGCTGCAAGGACCGGATCCAGCGGCAACTGGAGATCACTGGA

AGGACCACCACCAACGAAGAACTGGAAGACATGCTGGAGAGCGGGAAGCTGGCCA

TCTTCACAGATGACATCAAAATGGACTCACAGATGACGAAGCAGGCGCTGAATGAG

ATTGAGACGAGGCACAATGAGATCATCAAGCTGGAGACCAGCATCCGCGAGCTGCA

CGATATGTTTGTGGACATGGCCATGCTCGTAGAGAGCCAGGGAGAGATGATTGACC

GCATCGAGTACAACGTGGAACATTCTGTGGACTACGTGGAGCGAGCTGTGTCTGAC

ACCAAGAAAGCAGTGAAATATCAGAGCAAGGCCCGGAGGAAGAAAATCATGATCA

TCATTTGCTGTGTGGTGCTGGGGGTGGTCTTGGCGTCGTCCATTGGGGGACGCTGG

GCTTGTAGCTCGAGCACCACCATCACCATCACCATCACTAAGTGATTAACCTCAGGT

GCAGGCTGCCTATCAGAAGGTGGTGGCTGGTGTGGCCAATGCCCTGGCTCACAAAT

ACCACTGAGATCGATCTTTTTCCCTCTGCCAAAAATTATGGGGACATCATGAAGCCC

CTTGAGCATCTGACTTCTGGCTAATAAAGGAAATTTATTTTCATTGCAATAGTGTGTT

GGAATTTTTTGTGTCTCTCACTCGGAAGGACATATGGGAGGGCAAATCATTTAAAAC

ATCAGAATGAGTATTTGGTTTAGAGTTTGGCAACATATGCCCATATGTAACTAGCAT

AACCCCTTGGGGCCTCTAAACGGGTCTTGAGGGGTTTTTGCTGAAAGCATGCGGAG

GAAATTCTCCTTGAAGTTTCCCTGGTGTTCAAAGTAAAGGAGTTTGCACCAGACGCA

CCTCTGTTCACTGGTCCGGCGTATTAAAACACGATACATTGTTATTAGTACATTTATT

AAGCGCTAGATTCTGTGCGTTGTTGATTTACAGACAATTGTTGTACGTATTTTAATAA

TTCATTAAATTTATAATCTTTAGGGTGGTATGTTAGAGCGAAAATCAAATGATTTTC

AGCGTCTTTATATCTGAATTTAAATATTAAATCCTCAATAGATTTGTAAAATAGGTTT

CGATTAGTTTCAAACAAGGGTTGTTTTTCCGAACCGATGGCTGGACTATCTAATGGA

TTTTCGCTCAACGCCACAAAACTTGCCAAATCTTGTAGCAGCAATCTAGCTTTGTCG

ATATTCGTTTGTGTTTTGTTTTGTAATAAAGGTTCGACGTCGTTCAAAATATTATGCG

CTTTTGTATTTCTTTCATCACTGTCGTTAGTGTACAATTGACTCGACGTAAACACGTT

AAATAGAGCTTGGACATATTTAACATCGGGCGTGTTAGCTTTATTAGGCCGATTATC

GTCGTCGTCCCAACCCTCGTCGTTAGAAGTTGCTTCCGAAGACGATTTTGCCATAGC

CACACGACGCCTATTAATTGTGTCGGCTAACACGTCCGCGATCAAATTTGTAGTTGA

GCTTTTTGGAATTATTTCTGATTGCGGGCGTTTTTGGGCGGGTTTCAATCTAACTGTG

CCCGATTTTAATTCAGACAACACGTTAGAAAGCGATGGTGCAGGCGGTGGTAACATT

TCAGACGGCAAATCTACTAATGGCGGCGGTGGTGGAGCTGATGATAAATCTACCAT

CGGTGGAGGCGCAGGCGGGGCTGGCGGCGGAGGCGGAGGCGGAGGTGGTGGCGGT

GATGCAGACGGCGGTTTAGGCTCAAATGTCTCTTTAGGCAACACAGTCGGCACCTCA

ACTATTGTACTGGTTTCGGGCGCCGTTTTTGGTTTGACCGGTCTGAGACGAGTGCGA

TTTTTTTCGTTTCTAATAGCTTCCAACAATTGTTGTCTGTCGTCTAAAGGTGCAGCGG

GTTGAGGTTCCGTCGGCATTGGTGGAGCGGGCGGCAATTCAGACATCGATGGTGGT

GGTGGTGGTGGAGGCGCTGGAATGTTAGGCACGGGAGAAGGTGGTGGCGGCGGTGC

CGCCGGTATAATTTGTTCTGGTTTAGTTTGTTCGCGCACGATTGTGGGCACCGGCGC
```

-continued

```
AGGCGCCGCTGGCTGCACAACGGAAGGTCGTCTGCTTCGAGGCAGCGCTTGGGGTG
GTGGCAATTCAATATTATAATTGGAATACAAATCGTAAAAATCTGCTATAAGCATTG
TAATTTCGCTATCGTTTACCGTGCCGATATTTAACAACCGCTCAATGTAAGCAATTGT
ATTGTAAAGAGATTGTCTCAAGCTCGGAACGCTGCGCTCGGTCGTTCGGCTGCGGCG
AGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCAATGCTCACGCTGTAGG
TATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGTTACCAA
TGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCA
GTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGG
CCGCAGTGTTATCACTCATGGTTATGGCAGCACTGCATAATTCTCTTACTGTCATGCC
ATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACT
CTCAAGGATCTTACCGCTGTTGAGATCCAGTTCGATGTAACCCACTCGTGCACCCAA
CTGATCTTCAGCATCTTTTACTTTCACCAGCGTTTCTGGGTGAGCAAAAACAGGAAG
GCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGTCCGCGCG
TTTCCTGCATCTTTTAATCAAATCCCAAGATGTGTATAAACCACCAAACTGCCAAAA
AATGAAAACTGTCGACAAGCTCTGTCCGTTTGCTGGCAACTGCAAGGGTCTCAATCC
TATTTGTAATTATTGAATAATAAAACAATTATAAATGTCAAATTTGTTTTTTATTAAC
GATACAAACCAAACGCAACAAGAACATTTGTAGTATTATCTATAATTGAAAACGCG
TAGTTATAATCGCTGAGGTAATATTTAAAATCATTTTCAAATGATTCACAGTTAATTT
GCGACAATATAATTTTATTTTCACATAAACTAGACGCCTTGTCGTCTTCTTCTTCGTA
TTCCTTCTCTTTTTCATTTTTCTCTTCATAAAAATTAACATAGTTATTATCGTATCCAT
```

-continued

ATATGTATCTATCGTATAGAGTAAATTTTTTGTTGTCATAAATATATATGTCTTTTTT

AATGGGGTGTATAGTACCGCTGCGCATAGTTTTTCTGTAATTTACAACAGTGCTATTT
TCTGGTAGTTCTTCGGAGTGTGTTGCTTTAATTATTAAATTTATATAATCAATGAATT
TGGGATCGTCGGTTTTGTACAATATGTTGCCGGCATAGTACGCAGCTTCTTCTAGTTC
AATTACACCATTTTTTAGCAGCACCGGATTAACATAACTTTCCAAAATGTTGTACGA
ACCGTTAAACAAAAACAGTTCACCTCCCTTTTCTATACTATTGTCTGCGAGCAGTTGT
TTGTTGTTAAAAATAACAGCCATTGTAATGAGACGCACAAACTAATATCACAAACTG
GAAATGTCTATCAATATATAGTTGCTCTAGTTATTAATAGTAATCAATTACGGGGTC
ATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCC
CATAGTAACGCCAATAGGGACTTTCCATTGACGTCAATGGGTGGACTATTTACGGTA
AACTGCCCACTTGGCAGTACATCAAGTGTATCATATGCCAAGTACGCCCCCTATTGA
CGTCAATGACGGTAAATGGCCCGCCTGGCATTATGCCCAGTACATGACCTTATGGGA
CTTTCCTACTTGGCAGTACATCTACGTATTAGTCATCGCTATTACCATGCATGGTCGA
GGTGAGCCCCACGTTCTGCTTCACTCTCCCCATCTCCCCCCCCTCCCCACCCCCAATT
TTGTATTTATTTATTTTTTAATTATTTTGTGCAGCGATGGGGGCGGGGGGGGGGGGG
GGGCGCGCGCCAGGCGGGGCGGGGCGGGGCGAGGGGCGGGGCGGGGCGAGGCGG
AGAGGTGCGGCGGCAGCCAATCAGAGCGGCGCGCTCCGAAAGTTTCCTTTTATGGC

GAGGCGGCGGCGGCGGCGGCCCTATAAAAAGCGAAGCGCGCGGCGGGCG (pTriEx-1-STX1B(ic)-His)

SEQ ID NO: 17

GGAGTCGCTGCGACGCTGCCTTCGCCCCGTGCCCCGCTCCGCCGCCGCCTCGCGCCG

CCCGCCCCGGCTCTGACTGACCGCGTTACTCCCACAGGTGAGCGGGCGGGACGGCC

CTTCTCCTTCGGGCTGTAATTAGCGCTTGGTTTAATGACGGCTTGTTTCTTTTCTGTG

GCTGCGTGAAAGCCTTGAGGGGCTCCGGGAGGGCCCTTTGTGCGGGGGGAGCGGCT

CGGGGCTGTCCGCGGGGGGACGGCTGCCTTCGGGGGGGACGGGGCAGGGCGGGGTT

CGGCTTCTGGCGTGTGACCGGCGGCTCTAGAGCCTCTGCTAACCATGTTCATGCCTT

CTTCTTTTTCCTACAGCTCCTGGGCAACGTGCTGGTTATTGTGCTGTCTCATCATTTTG

GCAAAGAATTGGATCGGACCGAAATTAATACGACTCACTATAGGGGAATTGTGAGC

GGATAACAATTCCCCGGAGTTAATCCGGGACCTTTAATTCAACCCAACACAATATAT

TATAGTTAAATAAGAATTATTATCAAATCATTTGTATATTAATTAAAATACTATACTG

TAAATTACATTTTATTTACAATCAAAGGAGATATACCATGAAGGATCGGACTCAAGA

GCTGCGGAGTGCGAAAGACAGTGATGATGAAGAGGAGGTGGTCCACGTGGATCGGG

ACCACTTCATGGATGAGTTCTTTGAACAGGTGGAAGAGATCCGGGGCTGCATTGAG

AAACTGTCGGAGGATGTGGAGCAGGTGAAAAAACAGCATAGCGCCATCCTGGCCGC

ACCCAACCCAGATGAGAAGACCAAACAGGAGCTGGAGGATCTCACTGCAGACATCA

AGAAGACGGCCAACAAGGTTCGGTCCAAATTGAAAGCGATCGAGCAAAGCATTGAA

CAGGAGGAGGGGCTGAACCGTTCCTCCGCGGACCTGCGCATCCGCAAGACCCAGCA

CTCCACACTGTCCCGGAAGTTCGTGGAGGTAATGACCGAATATAACGCGACCCAGT

CCAAGTACCGGGACCGCTGCAAGGACCGGATCCAGCGGCAACTGGAGATCACTGGA

AGGACCACCACCAACGAAGAACTGGAAGACATGCTGGAGAGCGGGAAGCTGGCCA

TCTTCACAGATGACATCAAAATGGACTCACAGATGACGAAGCAGGCGCTGAATGAG

-continued

```
ATTGAGACGAGGCACAATGAGATCATCAAGCTGGAGACCAGCATCCGCGAGCTGCA

CGATATGTTTGTGGACATGGCCATGCTCGTAGAGAGCCAGGGAGAGATGATTGACC

GCATCGAGTACAACGTGGAACATTCTGTGGACTACGTGGAGCGAGCTGTGTCTGAC

ACCAAGAAAGCAGTGAAATATCAGAGCAAGGCCCGGAGGAAGAAACTCGAGCACC

ACCATCACCATCACCATCACTAAGTGATTAACCTCAGGTGCAGGCTGCCTATCAGAA

GGTGGTGGCTGGTGTGGCCAATGCCCTGGCTCACAAATACCACTGAGATCGATCTTT

TTCCCTCTGCCAAAAATTATGGGGACATCATGAAGCCCCTTGAGCATCTGACTTCTG

GCTAATAAAGGAAATTTATTTTCATTGCAATAGTGTGTTGGAATTTTTTGTGTCTCTC

ACTCGGAAGGACATATGGGAGGGCAAATCATTTAAAACATCAGAATGAGTATTTGG

TTTAGAGTTTGGCAACATATGCCCATATGTAACTAGCATAACCCCTTGGGGCCTCTA

AACGGGTCTTGAGGGGTTTTTTGCTGAAAGCATGCGGAGGAAATTCTCCTTGAAGTT

TCCCTGGTGTTCAAAGTAAAGGAGTTTGCACCAGACGCACCTCTGTTCACTGGTCCG

GCGTATTAAAACACGATACATTGTTATTAGTACATTTATTAAGCGCTAGATTCTGTG

CGTTGTTGATTTACAGACAATTGTTGTACGTATTTTAATAATTCATTAAATTTATAAT

CTTTAGGGTGGTATGTTAGAGCGAAAATCAAATGATTTTCAGCGTCTTTATATCTGA

ATTTAAATATTAAATCCTCAATAGATTTGTAAAATAGGTTTCGATTAGTTTCAAACA

AGGGTTGTTTTCCGAACCGATGGCTGGACTATCTAATGGATTTTCGCTCAACGCCA

CAAAACTTGCCAAATCTTGTAGCAGCAATCTAGCTTTGTCGATATTCGTTTGTGTTTT

GTTTTGTAATAAAGGTTCGACGTCGTTCAAAATATTATGCGCTTTTGTATTTCTTTCA

TCACTGTCGTTAGTGTACAATTGACTCGACGTAAACACGTTAAATAGAGCTTGGACA

TATTTAACATCGGGCGTGTTAGCTTTATTAGGCCGATTATCGTCGTCGTCCCAACCCT

CGTCGTTAGAAGTTGCTTCCGAAGACGATTTTGCCATAGCCACACGACGCCTATTAA

TTGTGTCGGCTAACACGTCCGCGATCAAATTTGTAGTTGAGCTTTTTGGAATTATTTC

TGATTGCGGGCGTTTTTGGGCGGGTTTCAATCTAACTGTGCCCGATTTTAATTCAGAC

AACACGTTAGAAAGCGATGGTGCAGGCGGTGGTAACATTTCAGACGGCAAATCTAC

TAATGGCGGCGGTGGTGGAGCTGATGATAAATCTACCATCGGTGGAGGCGCAGGCG

GGGCTGGCGGCGGAGGCGGAGGCGGAGGTGGTGGCGGTGATGCAGACGGCGGTTT

AGGCTCAAATGTCTCTTTAGGCAACACAGTCGGCACCTCAACTATTGTACTGGTTTC

GGGCGCCGTTTTTGGTTTGACCGGTCTGAGACGAGTGCGATTTTTTTCGTTTCTAATA

GCTTCCAACAATTGTTGTCTGTCGTCTAAAGGTGCAGCGGGTTGAGGTTCCGTCGGC

ATTGGTGGAGCGGGCGGCAATTCAGACATCGATGGTGGTGGTGGTGGAGGCGC

TGGAATGTTAGGCACGGGAGAAGGTGGTGGCGGCGGTGCCGCCGGTATAATTTGTT

CTGGTTTAGTTTGTTCGCGCACGATTGTGGGCACCGGCGCAGGCGCCGCTGGCTGCA

CAACGGAAGGTCGTCTGCTTCGAGGCAGCGCTTGGGGTGGTGGCAATTCAATATTAT

AATTGGAATACAAATCGTAAAAATCTGCTATAAGCATTGTAATTTCGCTATCGTTTA

CCGTGCCGATATTTAACAACCGCTCAATGTAAGCAATTGTATTGTAAAGAGATTGTC

TCAAGCTCGGAACGCTGCGCTCGGTCGTTCGGCTGCGGCGAGCGGTATCAGCTCACT

CAAAGGCGGTAATACGGTTATCCACAGAATCAGGGGATAACGCAGGAAAGAACATG

TGAGCAAAAGGCCAGCAAAAGGCCAGGAACCGTAAAAAGGCCGCGTTGCTGGCGTT

TTTCCATAGGCTCCGCCCCCCTGACGAGCATCACAAAAATCGACGCTCAAGTCAGAG
```

-continued

```
GTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCC
TTCGGGAAGCGTGGCGCTTTCTCAATGCTCACGCTGTAGGTATCTCAGTTCGGTGTA
GGTCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGGACAGTATTTGGTA
TCTGCGCTCTGCTGAAGCCAGTTACCTTCGGAAAAAGAGTTGGTAGCTCTTGATCCG
GCAAACAAACCACCGCTGGTAGCGGTGGTTTTTTGTTTGCAAGCAGCAGATTACGC
GCAGAAAAAAAGGATCTCAAGAAGATCCTTTGTTACCAATGCTTAATCAGTGAGGC
ACCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCG
CGAGACCCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGC
CATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGACCGA
GTTGCTCTTGCCCGGCGTCAATACGGGATAATACCGCGCCACATAGCAGAACTTTAA
AAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAA
AGGGAATAAGGGCGACACGGAAATGTTGAATACTCATACTCTTCCTTTTTCAATATT
ATTGAAGCATTTATCAGGGTTATTGTCTCATGTCCGCGCGTTTCCTGCATCTTTTAAT
CAAATCCCAAGATGTGTATAAACCACCAAACTGCCAAAAAATGAAAACTGTCGACA
AGCTCTGTCCGTTTGCTGGCAACTGCAAGGGTCTCAATCCTATTTGTAATTATTGAAT
AATAAAACAATTATAAATGTCAAATTTGTTTTTTATTAACGATACAAACCAAACGCA
ACAAGAACATTTGTAGTATTATCTATAATTGAAAACGCGTAGTTATAATCGCTGAGG
TAATATTTAAAATCATTTTCAAATGATTCACAGTTAATTTGCGACAATATAATTTTAT
TTTCACATAAACTAGACGCCTTGTCGTCTTCTTCTTCGTATTCCTTCTCTTTTTCATTT
TTCTCTTCATAAAAATTAACATAGTTATTATCGTATCCATATATGTATCTATCGTATA
GAGTAAATTTTTGTTGTCATAAATATATATGTCTTTTTTAATGGGGTGTATAGTACC
GCTGCGCATAGTTTTTCTGTAATTTACAACAGTGCTATTTTCTGGTAGTTCTTCGGAG
TGTGTTGCTTTAATTATTAAATTTATATAATCAATGAATTTGGGATCGTCGGTTTTGT
ACAATATGTTGCCGGCATAGTACGCAGCTTCTTCTAGTTCAATTACACCATTTTTTAG
CAGCACCGGATTAACATAACTTTCCAAAATGTTGTACGAACCGTTAAACAAAAACA
GTTCACCTCCCTTTTCTATACTATTGTCTGCGAGCAGTTGTTTGTTGTTAAAAATAAC
AGCCATTGTAATGAGACGCACAAACTAATATCACAAACTGGAAATGTCTATCAATAT
ATAGTTGCTCTAGTTATTAATAGTAATCAATTACGGGGTCATTAGTTCATAGCCCAT
```

-continued

ATATGGAGTTCCGCGTTACATAACTTACGGTAAATGGCCCGCCTGGCTGACCGCCCA

ACGACCCCCGCCCATTGACGTCAATAATGACGTATGTTCCCATAGTAACGCCAATAG

GGACTTTCCATTGACGTCAATGGGTGGACTATTTACGGTAAACTGCCCACTTGGCAG

TACATCAAGTGTATCATATGCCAAGTACGCCCCCTATTGACGTCAATGACGGTAAAT

GGCCCGCCTGGCATTATGCCCAGTACATGACCTTATGGGACTTTCCTACTTGGCAGT

ACATCTACGTATTAGTCATCGCTATTACCATGCATGGTCGAGGTGAGCCCCACGTTC

TGCTTCACTCTCCCCATCTCCCCCCCCTCCCCACCCCCAATTTTGTATTTATTTATTTT

TTAATTATTTTGTGCAGCGATGGGGGCGGGGGGGGGGGGGGGCGCGCGCCAGGCG

GGGCGGGGCGGGGCGAGGGGCGGGGCGGGGCGAGGCGGAGAGGTGCGGCGGCAG

CCAATCAGAGCGGCGCGCTCCGAAAGTTTCCTTTTATGGCGAGGCGGCGGCGGCGG

CGGCCCTATAAAAAGCGAAGCGCGCGGCGGGCG (pTriEx-1-VAMP2)
SEQ ID NO: 18

GGAGTCGCTGCGACGCTGCCTTCGCCCCGTGCCCCGCTCCGCCGCCGCCTCGCGCCG

CCCGCCCCGGCTCTGACTGACCGCGTTACTCCCACAGGTGAGCGGGCGGGACGGCC

CTTCTCCTTCGGGCTGTAATTAGCGCTTGGTTTAATGACGGCTTGTTTCTTTTCTGTG

GCTGCGTGAAAGCCTTGAGGGGCTCCGGGAGGGCCCTTTGTGCGGGGGGAGCGGCT

CGGGGCTGTCCGCGGGGGGACGGCTGCCTTCGGGGGGGACGGGGCAGGGCGGGGTT

CGGCTTCTGGCGTGTGACCGGCGGCTCTAGAGCCTCTGCTAACCATGTTCATGCCTT

CTTCTTTTTCCTACAGCTCCTGGGCAACGTGCTGGTTATTGTGCTGTCTCATCATTTTG

GCAAAGAATTGGATCGGACCGAAATTAATACGACTCACTATAGGGGAATTGTGAGC

GGATAACAATTCCCCGGAGTTAATCCGGGACCTTTAATTCAACCCAACACAATATAT

TATAGTTAAATAAGAATTATTATCAAATCATTTGTATATTAATTAAAATACTATACTG

TAAATTACATTTTATTTACAATCAAAGGAGATATACCATGTCTGCTACCGCTGCCAC

GGCCCCCCCTGCTGCCCCGGCTGGGGAGGGTGGTCCCCCTGCACCCCCTCCAAACCT

CACCAGTAACAGGAGACTGCAGCAGACCCAGGCCCAGGTGGATGAGGTGGTGGAC

ATCATGAGGGTGAACGTGGACAAGGTCCTGGAGCGAGACCAGAAGCTGTCGGAGCT

GGACGACCGTGCAGATGCACTCCAGGCGGGGCCTCCCAGTTTGAAACAAGCGCAG

CCAAGCTCAAGCGCAAATACTGGTGGAAAAACCTCAAGATGATGATCATCTTGGGA

GTGATTTGCGCCATCATCCTCATCATCATCATAGTTTACTTCAGCACTTAACTCGAGC

ACCACCATCACCATCACCATCACTAAGTGATTAACCTCAGGTGCAGGCTGCCTATCA

GAAGGTGGTGGCTGGTGTGGCCAATGCCCTGGCTCACAAATACCACTGAGATCGAT

CTTTTTCCCTCTGCCAAAAATTATGGGGACATCATGAAGCCCCTTGAGCATCTGACTT

CTGGCTAATAAAGGAAATTTATTTTCATTGCAATAGTGTGTTGGAATTTTTTGTGTCT

CTCACTCGGAAGGACATATGGGAGGGCAAATCATTTAAAACATCAGAATGAGTATT

TGGTTTAGAGTTTGGCAACATATGCCCATATGTAACTAGCATAACCCCTTGGGGCCT

CTAAACGGGTCTTGAGGGGTTTTTTGCTGAAAGCATGCGGAGGAAATTCTCCTTGAA

GTTTCCCTGGTGTTCAAAGTAAAGGAGTTTGCACCAGACGCACCTCTGTTCACTGGT

CCGGCGTATTAAAACACGATACATTGTTATTAGTACATTTATTAAGCGCTAGATTCT

GTGCGTTGTTGATTTACAGACAATTGTTGTACGTATTTTAATAATTCATTAAATTTAT

AATCTTTAGGGTGGTATGTTAGAGCGAAAATCAAATGATTTTCAGCGTCTTTATATC

-continued

```
TGAATTTAAATATTAAATCCTCAATAGATTTGTAAAATAGGTTTCGATTAGTTTCAA
ACAAGGGTTGTTTTTCCGAACCGATGGCTGGACTATCTAATGGATTTTCGCTCAACG
CCACAAAACTTGCCAAATCTTGTAGCAGCAATCTAGCTTTGTCGATATTCGTTTGTGT
TTTGTTTTGTAATAAAGGTTCGACGTCGTTCAAAATATTATGCGCTTTTGTATTTCTTT
CATCACTGTCGTTAGTGTACAATTGACTCGACGTAAACACGTTAAATAGAGCTTGGA
CATATTTAACATCGGGCGTGTTAGCTTTATTAGGCCGATTATCGTCGTCGTCCCAACC
CTCGTCGTTAGAAGTTGCTTCCGAAGACGATTTTGCCATAGCCACACGACGCCTATT
AATTGTGTCGGCTAACACGTCCGCGATCAAATTTGTAGTTGAGCTTTTTGGAATTATT
TCTGATTGCGGGCGTTTTTGGGCGGGTTTCAATCTAACTGTGCCCGATTTTAATTCAG
ACAACACGTTAGAAAGCGATGGTGCAGGCGGTGGTAACATTTCAGACGGCAAATCT
ACTAATGGCGGCGGTGGTGGAGCTGATGATAAATCTACCATCGGTGGAGGCGCAGG
CGGGGCTGGCGGCGGAGGCGGAGGCGGAGGTGGTGGCGGTGATGCAGACGGCGGT
TTAGGCTCAAATGTCTCTTTAGGCAACACAGTCGGCACCTCAACTATTGTACTGGTTT
CGGGCGCCGTTTTTGGTTTGACCGGTCTGAGACGAGTGCGATTTTTTTCGTTTCTAAT
AGCTTCCAACAATTGTTGTCTGTCGTCTAAAGGTGCAGCGGGTTGAGGTTCCGTCGG
CATTGGTGGAGCGGGCGGCAATTCAGACATCGATGGTGGTGGTGGTGGAGGCG
CTGGAATGTTAGGCACGGGAGAAGGTGGTGGCGGCGGTGCCGCCGGTATAATTTGT
TCTGGTTTAGTTTGTTCGCGCACGATTGTGGGCACCGGCGCAGGCGCCGCTGGCTGC
ACAACGGAAGGTCGTCTGCTTCGAGGCAGCGCTTGGGGTGGTGGCAATTCAATATTA
TAATTGGAATACAAATCGTAAAAATCTGCTATAAGCATTGTAATTTCGCTATCGTTT
ACCGTGCCGATATTTAACAACCGCTCAATGTAAGCAATTGTATTGTAAAGAGATTGT
CTCAAGCTCGGAACGCTGCGCTCGGTCGTTCGGCTGCGGCGAGCGGTATCAGCTCAC
TCAAAGGCGGTAATACGGTTATCCACAGAATCAGGGGATAACGCAGGAAAGAACAT
GTGAGCAAAAGGCCAGCAAAAGGCCAGGAACCGTAAAAAGGCCGCGTTGCTGGCG
TTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTC
CCTTCGGGAAGCGTGGCGCTTTCTCAATGCTCACGCTGTAGGTATCTCAGTTCGGTG
TAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGTGC
TACAGAGTTCTTGAAGTGGTGGCCTAACTACGGCTACACTAGAAGGACAGTATTTGG
TATCTGCGCTCTGCTGAAGCCAGTTACCTTCGGAAAAAGAGTTGGTAGCTCTTGATC
CGGCAAACAAACCACCGCTGGTAGCGGTGGTTTTTTTGTTTGCAAGCAGCAGATTAC
GCGCAGAAAAAAAGGATCTCAAGAAGATCCTTTGTTACCAATGCTTAATCAGTGAG
GCACCTATCTCAGCGATCTGTCTATTTCGTTCATCCATAGTTGCCTGACTCCCCGTCG
TGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGA
AGGGCCGAGCGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTCATTCAGCT
```

-continued

```
CCGGTTCCCAACGATCAAGGCGAGTTACATGATCCCCCATGTTGTGCAAAAAAGCG

GTTAGCTCCTTCGGTCCTCCGATCGTTGTCAGAAGTAAGTTGGCCGCAGTGTTATCA

CTCATGGTTATGGCAGCACTGCATAATTCTCTTACTGTCATGCCATCCGTAAGATGCT

TTTCTGTGACTGGTGAGTACTCAACCAAGTCATTCTGAGAATAGTGTATGCGGCGAC

CGAGTTGCTCTTGCCCGGCGTCAATACGGGATAATACCGCGCCACATAGCAGAACTT

TAAAAGTGCTCATCATTGGAAAACGTTCTTCGGGGCGAAAACTCTCAAGGATCTTAC

CGCTGTTGAGATCCAGTTCGATGTAACCCACTCGTGCACCCAACTGATCTTCAGCAT

CTTTTACTTTCACCAGCGTTTCTGGGTGAGCAAAAACAGGAAGGCAAATGCCGCAA

AAAAGGGAATAAGGGCGACACGGAAATGTTGAATACTCATACTCTTCCTTTTTCAAT

ATTATTGAAGCATTTATCAGGGTTATTGTCTCATGTCCGCGCGTTTCCTGCATCTTTT

AATCAAATCCCAAGATGTGTATAAACCACCAAACTGCCAAAAAATGAAAACTGTCG

ACAAGCTCTGTCCGTTTGCTGGCAACTGCAAGGGTCTCAATCCTATTTGTAATTATTG

AATAATAAAACAATTATAAATGTCAAATTTGTTTTTTATTAACGATACAAACCAAAC

GCAACAAGAACATTTGTAGTATTATCTATAATTGAAAACGCGTAGTTATAATCGCTG

AGGTAATATTTAAAATCATTTTCAAATGATTCACAGTTAATTTGCGACAATATAATTT

TATTTTCACATAAACTAGACGCCTTGTCGTCTTCTTCTTCGTATTCCTTCTCTTTTTCA

TTTTTCTCTTCATAAAAATTAACATAGTTATTATCGTATCCATATATGTATCTATCGT

ATAGAGTAAATTTTTTGTTGTCATAAATATATATGTCTTTTTTAATGGGGTGTATAGT

ACCGCTGCGCATAGTTTTTCTGTAATTTACAACAGTGCTATTTTCTGGTAGTTCTTCG

GAGTGTGTTGCTTTAATTATTAAATTTATATAATCAATGAATTTGGGATCGTCGGTTT

TGTACAATATGTTGCCGGCATAGTACGCAGCTTCTTCTAGTTCAATTACACCATTTTT

TAGCAGCACCGGATTAACATAACTTTCCAAAATGTTGTACGAACCGTTAAACAAAA

ACAGTTCACCTCCCTTTTCTATACTATTGTCTGCGAGCAGTTGTTTGTTGTTAAAAAT

AACAGCCATTGTAATGAGACGCACAAACTAATATCACAAACTGGAAATGTCTATCA

ATATATAGTTGCTCTAGTTATTAATAGTAATCAATTACGGGGTCATTAGTTCATAGCC

CATATATGGAGTTCCGCGTTACATAACTTACGGTAAATGGCCCGCCTGGCTGACCGC

CCAACGACCCCCGCCCATTGACGTCAATAATGACGTATGTTCCCATAGTAACGCCAA

TAGGGACTTTCCATTGACGTCAATGGGTGGACTATTTACGGTAAACTGCCCACTTGG

CAGTACATCAAGTGTATCATATGCCAAGTACGCCCCCTATTGACGTCAATGACGGTA

AATGGCCCGCCTGGCATTATGCCCAGTACATGACCTTATGGGACTTTCCTACTTGGC

AGTACATCTACGTATTAGTCATCGCTATTACCATGCATGGTCGAGGTGAGCCCCACG

TTCTGCTTCACTCTCCCCATCTCCCCCCCCTCCCCACCCCCAATTTTGTATTTATTTAT

TTTTTAATTATTTTGTGCAGCGATGGGGGCGGGGGGGGGGGGGGCGCGCGCCAG

GCGGGGCGGGGCGGGGCGAGGGGCGGGGCGGGGCGAGGCGGAGAGGTGCGGCGG

CAGCCAATCAGAGCGGCGCGCTCCGAAAGTTTCCTTTTATGGCGAGGCGGCGGCGG

CGGCGGCCCTATAAAAAGCGAAGCGCGCGGCGGGCG
```

(DNM1)

SEQ ID NO: 19

```
MGNRGMEDLIPLVNRLQDAFSAIGQNADLDLPQIAVVGGQSAGKSSVLENFVGRDFLPR

GSGIVTRRPLVLQLVNATTEYAEFLHCKGKKFTDFEEVRLEIEAETDRVTGTNKGISPVPI

NLRVYSPHVLNLTLVDLPGMTKVPVGDQPPDIEFQIRDMLMQFVTKENCLILAVSPANS
```

-continued

DLANSDALKVAKEVDPQGQRTIGVITKLDLMDEGTDARDVLENKLLPLRRGYIGVVNR

SQKDIDGKKDITAALAAERKFFLSHPSYRHLADRMGTPYLQKVLNQQLTNHIRDTLPGL

RNKLQSQLLSIEKEVEEYKNFRPDDPARKTKALLQMVQQFAVDFEKRIEGSGDQIDTYE

LSGGARINRIFHERFPFELVKMEFDEKELRREISYAIKNIHGIRTGLFTPDMAFETIVKKQV

KKIREPCLKCVDMVISELISTVRQCTKKLQQYPRLREEMERIVTTHIREREGRTKEQVML

LIDIELAYMNTNHEDFIGFANAQQRSNQMNKKKTSGNQDEILVIRKGWLTINNIGIMKG

GSKEYWFVLTAENLSWYKDDEEKEKKYMLSVDNLKLRDVEKGFMSSKHIFALFNTEQR

NVYKDYRQLELACETQEEVDSWKASFLRAGVYPERVGDKEKASETEENGSDSFMHSM

DPQLERQVETIRNLVDSYMAIVNKTVRDLMPKTIMHLMINNTKEFIFSELLANLYSCGDQ

NTLMEESAEQAQRRDEMLRMYHALKEALSIIGDINTTTVSTPMPPPVDDSWLQVQSVPA

GRRSPTSSPTPQRRAPAVPPARPGSRGPAPGPPPAGSALGGAPPVPSRPGASPDPFGPPPQ

VPSRPNRAPPGVPSRSGQASPSRPESPRPPFDL

SEQ ID NO: 20 gggcgggggccccgcggcgcaggcagtctgggcgcgcggctgcagcggcggagccggagtcggag ccgggagcgctagcggcagccggatcgcagcctgcggggcccgccgcagccatgggcaaccgcgg catggaagatctcatcccgctggtcaaccggctgcaagacgccttctctgccatcggccagaacg cggacctcgacctgccgcagatcgctgtggtgggcggccagagcgccggcaagagctcggtgctc gagaatttcgtaggcagggacttcttgcctcgaggatctggcattgtcacccgacgtccctggt cttgcagctggtcaatgcaaccacagaatatgccgagttcctgcactgcaagggaaagaaattca ccgacttcgaggaggtgcgccttgagatcgaggccgagaccgacagggtcaccggcaccaacaag ggcatctcgccggtgcctatcaacctccgcgtctactcgccgcacgtgctgaacctgaccctggt ggacctgcccggaatgaccaaggtcccggtgggggaccaacctcccgacatcgagttccagatcc gagacatgcttatgcagtttgtcaccaaggagaactgcctcatcctggccgtgtccccgccaac tctgacctggccaattctgacgccctcaaggtcgccaaggaggtggaccccagggccagcgcac catcggggtcatcaccaagctggacctgatggacgagggcacagatgcccgtgatgtgctggaga acaagctgctcccccctgcgcagaggctacattggagtggtgaaccggagccagaaggacattgat ggcaagaaggacattaccgccgccttggctgctgaacgaaagttcttcctctcccatccatctta tcgccacttggctgaccgtatgggcacgccctacctgcagaaggtcctcaatcagcaactgacga accacatccgggacacactgccggggctgcggaacaagctgcagagccagctactgtccattgag aaggaggtggaggaatacaagaacttccgccctgatgacccagctcgcaagaccaaggccctgct gcagatggtccagcagttcgccgtagactttgagaagcgcattgagggctcaggagatcagatcg acacctacgaactgtcaggggagcccgcattaaccgaatcttccacgagcgcttcccttttcgag ctggtcaagatggagtttgatgagaaggaactccgaagggagatcagctatgctatcaagaatat ccatggcattagaacgggctgtttaccccagacatggcctttgagaccattgtgaaaaagcagg tgaagaagatccgagaaccgtgtctcaagtgtgtggacatggttatctcggagctaatcagcacc gttagacagtgcaccaagaagctccagcagtacccgcggctacgggaggagatggagcgcatcgt gaccacccacatccgggagcgcgagggccgcactaaggagcaggtcatgcttctcatcgatatcg agctggcttacatgaacaccaaccatgaggacttcataggctttgccaatgctcagcagaggagc aaccagatgaacaagaagaagacttcagggaaccaggatgagattctggtcatccgcaagggctg gctgactatcaataatattggcatcatgaaaggggggctccaaggagtactggtttgtgctgactg ctgagaatctgtcctggtacaaggatgatgaggagaaagagaagaaatacatgctgtctgtggac -continued

```
aacctcaagctgcgggacgtggagaagggctttatgtcgagcaagcatatctttgccctctttaa cacggagcagaggaatgtctacaaggattatcggcagctggagctagcctgtgagacacaggagg aggtggacagctggaaggcctccttcctgagggctggcgtgtaccctgagcgtgttggggacaaa gagaaagccagcgagaccgaggagaatggctccgacagcttcatgcattccatggacccacagct ggaacggcaagtggagaccatccggaatcttgtggactcatacatggccattgtcaacaagaccg tgagggacctcatgcccaagaccatcatgcacctcatgattaacaataccaaggagttcatcttc tcggagctgctggccaacctgtactcgtgtggggaccagaacacgctgatggaggagtcggcgga gcaggcacagcggcgcgacgagatgctgcgcatgtaccacgcactgaaggaggcgctcagcatca tcggcgacatcaacacgaccaccgtcagcacgccatgccccgccgtggacgactcctggctg caggtgcagagcgtaccggccggacgcaggtcgcccacgtccagcccacgccgcagcgccgagc ccccgccgtgccccagcccggcccgggtcgcggggccctgctcctgggcctccgcctgctgggt ccgccctggggggggcgcccccgtgccctccaggccggggcttccctgacccttcggccct cccctcaggtgcctcgcgccccaaccgcgcccgccggggtcccagccgatcgggtcaggc aagtccatcccgtcctgagagcccaggcccccttcgacctctaaacagatccctcctcttctc ggagacctccctttccaagcctgcctggacggctgttctgtgacttgacagtggctcccccagcc ccaaagccagccccttcatctgtgacttaatctgttgtagtggtgagctgatacattcaggtgt gaccgttggtgaaaacttgtgcccttctgtggtatgcccttgccctgttctataaatatctata aatactcatatatatacacacctacacatggccaaccgcctcgcctctagcgctgggaatcagtc actgtgctatccttgtggagtcttgtggcccaactaccagagaacgctgtccccgacatcccac tccaaagtgtgccacctccagtgagcctccttgtcatgcccggcctgtggacagccagccccgc catccctcccacccctaccaagcatgggggtgctgtgcaggcagccgtgtggcctgacagtttc taccagtcctgctgtccctcggctgagaataaaacccatttctggatgatggggaatgtcaaaaa aaaaaaaaaa
```

The present invention is further illustrated by the following non-limiting examples from which further features, embodiments, aspects and advantages of the present invention may be taken.

EXAMPLES

Summary

Methods: Two patients (P1-P2) with idiopathic encephalitis and an autoimmune background underwent serological investigation. For this purpose, sera from both patients and matched cerebrospinal fluid (CSF) from P2 were subjected to comprehensive autoantibody screening by indirect immunofluorescence assay (IFA) and immunoblot. Immunoprecipitation with lysates of cerebellum followed by mass spectrometry (MS) was used to identify the autoantigen, which was verified by Western blot (WB) with monospecific animal antibody against the respective target antigen as well as by recombinant expression in HEK293 cells and use of the recombinant protein in immunoassays. Furthermore, sera of patients with neurological symptoms and defined anti-neural autoantibodies, sera with a similar staining pattern as patient 1 and 2 without known autoantibody reactivity, as well as negative control sera were screened for anti-STX1B antibodies. All sera were additionally analyzed by IFA or Western blot with other recombinant SNARE complex proteins (VAMP2, NSF) as substrates.

Results: IFA screening of P1 and P2 revealed IgG reactivity in sera and CSF with the molecular and granular layers in rodent and monkey cerebellum. Furthermore, no IgG reactivity was found with a panel of 30 recombinantly expressed established neural autoantigens. The sera of P1 and P2 immunoprecipitated syntaxin 1B (STX1B), as detected by Coomassie-stained SDS-PAGE followed by MALDI-TOF mass spectrometry. When the immunoprecipitates were analyzed by Western blot using monospecific animal antibodies against STX1B, anti-STX1B showed reactivity with the immunoprecipitate of P1 and P2. Anti-STX1B antibodies were not found in any of 45 healthy controls. However, in two patient sera (P3 and P4) with a similar staining pattern on cerebellum as P1 and P2 anti-STX1B antibodies could be detected by RC-IFA and Western blot with the recombinant protein. Furthermore, anti-GAD65 positive sera of two patients who were pre-diagnosed with stiff person syndrome (P6 and P7) were positive in IFA with recombinant STX1B. Screening of control and anti-STX1B positive sera against other recombinant SNARE proteins revealed three anti-NSF (P3, P6 and P7) positive and one anti-VAMP2 (P5) positive sample.

These results show that the emergence and detection of an autoantibody is specifically linked to the emergence of AE and SPS, respectively, and, consequently, diagnostically useful.

Patients

Control collectives included 45 healthy donors, 33 patients with neurological symptoms and defined anti-neural autoantibodies (3× anti-CASPR2, 3× anti-NMDAR, 3× anti- LGI1, 3× anti-Hu, 3× anti-Ri, 2× anti-Yo/anti-Ri, 3× anti-Yo, 3× anti-AQP4, 10× anti-GAD65), and 10 sera with a similar staining pattern as P1 and P2 without known autoantibody reactivity.

Indirect Immunofluorescence Assay (IFA)

IFA was conducted using slides with a biochip array of brain tissue cryosections (hippocampus of rat, cerebellum of rat and monkey) combined with recombinant HEK293 cells separately expressing 30 different brain antigens Hu, Yo, Ri, CV2, PNMA2, ITPR1, Homer 3, CARP VIII, ARHGAP26, ZIC4, DNER/Tr, GAD65, GAD67, amphiphysin, recoverin, $GABA_B$ receptor, glycine receptor, DPPX, IgLON5, glutamate receptors (types NMDA, AMPA, mGluR1, mGluR5, GLURD2), LGI1, CASPR2, AQP4 (M1 and M23), MOG, ATP1A3, NCDN (EUROIMMUN, FA 111a-1003-51, FA 1112-1003-50, FA-1128-1003-50, FA112d-1003-1, FA 112m-1003-50, FA 1151-1003-50, Miske R, Hahn S, Rosenkranz T, Müller M, Dettmann I M, Mindorf S, Denno Y, Brakopp S, Scharf M, Teegen B, Probst C, Melzer N, Meinck H M, Terborg C, Stöcker W, Komorowski L., 2016, Autoantibodies against glutamate receptor δ2 after allogenic stem cell transplantation. Neurol Neuroimmunol Neuroinflamm., 3(4):e255; Scharf M, Miske R, Heidenreich F, Giess R, Landwehr P, Blöcker I M, Begemann N, Denno Y, Tiede S, Dähnrich C, Schlumberger W, Unger M, Teegen B, Stöcker W, Probst C, Komorowski L, 2015, Neuronal Na+/K+ ATPase is an autoantibody target in paraneoplastic neurologic syndrome, Neurology; 84(16):1673-9; Miske R, Gross C C, Scharf M, Golombeck K S, Hartwig M, Bhatia U, Schulte-Mecklenbeck A, Bönte K, Strippel C, Schöls L, Synofzik M, Lohmann H, Dettmann I M, Deppe M, Mindorf S, Warnecke T, Denno Y, Teegen B, Probst C, Brakopp S, Wandinger K P, Wiendl H, Stöcker W, Meuth S G, Komorowski L, Melzer N, 2016, Neurochondrin is a neuronal target antigen in autoimmune cerebellar degeneration, Neurol Neuroimmunol Neuroinflamm.; 4(1):e307)). Each biochip mosaic was incubated with 70 μL of PBS-diluted sample at room temperature for 30 min, washed with PBS-Tween and immersed in PBS-Tween for 5 min. In the second step, either Alexa488-labelled goat anti-human IgG (Jackson Research, Suffolk, United Kingdom), or fluorescein isothiocyanate (FITC)-labelled goat anti-human IgG (EUROIMMUN Medizinische Labordiagnostika AG, Lübeck) were applied and incubated at room temperature for 30 min. Slides were washed again with a flush of PBS-Tween and then immersed in PBS-Tween for 5 min. Slides were embedded in PBS-buffered, DABCO containing glycerol (approximately 20 μL per field) and examined by fluorescence microscopy. Positive and negative controls were included. Samples were classified as positive or negative based on fluorescence intensity of the transfected cells in direct comparison with non-transfected cells and control samples. Endpoint titers refer to the last dilution showing visible fluorescence.

Results were evaluated by two independent observers using a EUROSTARII microscope (EUROIMMUN Medizinische Labordiagnostika AG, Lübeck, Germany). Reagents were obtained from Merck, Darmstadt, Germany or Sigma-Aldrich, Heidelberg, Germany if not specified otherwise.

Immunoblot

Immunoprecipitated cerebellum lysate or lysate of HEK293 cells expressing SEQ ID NO: 2 or SEQ-ID 4, or SEQ-ID 5 or SEQ-ID 7 in 0,1% Triton-X-100, 1 mM EDTA buffer, 150 mM NaCl, 100 mM Tris pH 7,4, were incubated with NuPage LDS sample buffer (ThermoFisher Scientific, Schwerte, Germany) containing 25 mmol/L dithiothreitol at 70° C. for 10 minutes, followed by SDS-PAGE (NuPAGE, ThermoFisher Scientific, Schwerte, Germany). Separated proteins were electrotransferred onto a nitrocellulose membrane by tank blotting with transfer buffer (ThermoFisher Scientific) according to the manufacturer's instructions. The membranes were blocked with Universal Blot Buffer plus (EUROIMMUN Medizinische Labordiagnostika AG, Lübeck) for 15 min and incubated with the patient or control sera (dilution 1:200) or monospecific mouse antibody against STX1B (R+D Systems, MAB6848, 1:10,000) in Universal Blot Buffer plus for 3 hours, followed by 3 washing steps with Universal Blot Buffer (EUROIMMUN Medizinische Labordiagnostika AG, Lübeck), a second incubation for 30 min with anti-human-IgG-AP (EUROIMMUN Medizinische Labordiagnostika AG, Lübeck, 1:10) or anti-mouse-IgG-AP (1:2,000) in Universal Blot Buffer plus, 3 washing steps, and staining with NBT/BCIP substrate (EUROIMMUN Medizinische Labordiagnostika AG, Lübeck). Reagents were obtained from Merck, Darmstadt, Germany or Sigma-Aldrich, Heidelberg, Germany if not specified otherwise.

Identification of the Antigens

Cerebellum from rat was dissected and shock-frozen in liquid nitrogen. The tissues were homogenised in solubilization buffer (100 mmol/L tris-HCl pH 7.4, 150 mmol/L sodium chloride, 2.5 mmol/L ethylenediamine tetraacetic acid, 0.5% (w/v) sodium deoxycholate, 1% (w/v) Triton X-100) containing protease inhibitors (Complete mini, Roche Diagnostics, Penzberg, Germany) with a Miccra D-8 (Roth, Karlsruhe, Germany) and a hand homogenizer (Sartorius, Göttingen, Germany) at 4° C. The tissue lysates was centrifuged at 21,000×g at 4° C. for 15 min and clear supernatants were incubated with patient's serum (diluted 1:16,7) at 4° C. overnight. The samples were then incubated with Protein G Dynabeads (ThermoFisher Scientific, Dreieich, Germany) at 4° C. for 3 h to capture immunocomplexes. Beads were washed 3 times with PBS, and eluted with NuPage LDS sample buffer (ThermoFisher Scientific, Schwerte, Germany) containing 25 mmol/L dithiothreitol at 70° C. for 10 min. Carbamidomethylation with 59 mM iodoacetamide (Bio-Rad, Hamburg, Germany) was performed prior to SDS-PAGE (NuPAGE, ThermoFisher Scientific, Schwerte, Germany). Separated proteins were visualized with Coomassie Brillant Blue (G-250) (Merck), and identified by mass spectrometric analysis.

Mass Spectrometry

Visible protein bands were excised from Coomassie Brilliant Blue G-250 stained gels. After destaining and tryptic digestion peptides were extracted and spotted with α-cyano-4-hydroxycinnamic acid onto a MTP AnchorChip™ 384 TF target.

MALDI-TOF/TOF measurements were performed with an Autoflex III smartbeam TOF/TOF200 System using flexControl 3.4 software. MS spectra for peptide mass fingerprinting (PMF) were recorded in positive ion reflector mode with 4,000-10,000 shots and in a mass range from 600 Da to 4,000 Da. Spectra were calibrated externally with the commercially available Peptide Calibration Standard II, processed with flexAnalysis 3.4 and peak lists were analyzed with BioTools 3.2.

The Mascot search engine Mascot Server 2.3 (Matrix Science, London, UK) was used for protein identification by searching against the NCBI or SwissProt database limited to Mammalia. Search parameters were as follows: Mass tolerance was set to 80 ppm, one missed cleavage site was accepted, and carbamidomethylation of cysteine residues as well as oxidation of methionine residues were set as fixed and variable modifications, respectively. To evaluate the protein hits, a significance threshold of p<0.05 was chosen.

For further confirmation of the PMF hits two to five peptides of each identified protein were selected for MS/MS measurements using the WARP feedback mechanism of BioTools. Parent and fragment masses were recorded with 400 and 1000 shots, respectively. Spectra were processed and analyzed as described above with a fragment mass tolerance of 0.7 Da.

Recombinant expression of NSF, STX1B, DNM1 and VAMP2 in HEK293 The coding DNAs for human NSF (SEQ ID NO: 1) was obtained by RT-PCR on brain total RNA and primers ATACGTCTCACATGGCGGGCCG-GAGCATGCAAG ([sense NSF], SEQ ID NO: 8) and TATCGTCTCCTCGATCAATCAAAATCAAGGGGG-CTAG ([asense NSF] SEQ ID NO: 9). The amplification products were digested with BsmBI and DpnI. The digested cDNAs were ligated with pTriEx-1 (Merck, Darmstadt, Germany). The resulting construct (SEQ ID NO: 15) coded SEQ ID NO: 2.

The coding DNAs for human STX1B (SEQ ID NO: 3) was obtained by RT-PCR on brain total RNA and primers ATACGTCTCACATGAAGGATCGGACTCAAGAGC-TGC ([sense STX1B], SEQ ID NO: 10) and either ATACGTCTCCTCGAGCTACAAGCCCAGCGTCCCC-CCAATG ([asense STX1B], SEQ ID NO: 11) or ATACGTCTCCTCGAGTTTCTTCCTCCGGGCCTTGC-TCTG ([asense STX1B(ic)-His], SEQ ID NO: 12). The amplification products were digested with Esp3I and DpnI. The digested cDNAs were ligated with pTriEx-1 (Merck, Darmstadt, Germany). The resulting constructs (SEQ ID NO: 16 and SEQ ID NO: 17) coded SEQ ID NO: 4 and SEQ ID NO: 5.

The coding DNAs for human VAMP2 (SEQ ID NO: 6) was obtained by RT-PCR on brain total RNA and primers ATACGTCTCTCATGTCTGCTACCGCTGCCACGGCCC ([sense VAMP2], SEQ ID NO: 13) and ATACGTCTCCTCGAGTTAAGTGCTGAAGTAAAC-TATGATG ([asense VAMP2], SEQ ID NO: 14). The amplification products were digested with Esp3I and DpnI. The digested cDNAs were ligated with pTriEx-1 (Merck, Darmstadt, Germany). The resulting construct (SEQ ID NO: 18) coded SEQ ID NO: 7.

NSF, STX1B, DNM1 and VAMP2, respectively, were expressed in the human cell line HEK293 after ExGen500-mediated transfection (ThermoFisher Scientific) according to the manufacturer's instructions. Cells were transfected in standard T-flasks and the cells were harvested after 5 days. The cell sediment was extracted with solubilization buffer. The extracts were stored in aliquots at −80° C. until further use.

Characterization of the Patients' Autoantibodies

Indirect immunofluorescence assays (IFA) of sera P1 to P2 using permeabilized cryosections of cerebellum showed smooth staining of the molecular and granular layers (FIG. 1). Further monospecific analyses were conducted with recombinant HEK293 cells expressing 30 neural autoantigens: Hu, Yo, Ri, CV2, PNMA2, SOX1, ITPR1, Homer 3, CARP VIII, ARHGAP26, ZIC4, DNER/Tr, GAD65, GAD67, amphiphysin, recoverin, GABAB receptor, glycine receptor, DPPX, IgLON5, glutamate receptors (types NMDA, AMPA, mGluR1, mGluR5, GLURD2), LGI1, CASPR2, AQP4 (M1 and M23), MOG, ATP1A3 and NCDN. No specific reactivity was observed.

Identification of STX1B as the Target Neuronal Autoantigens

Figure 3A:
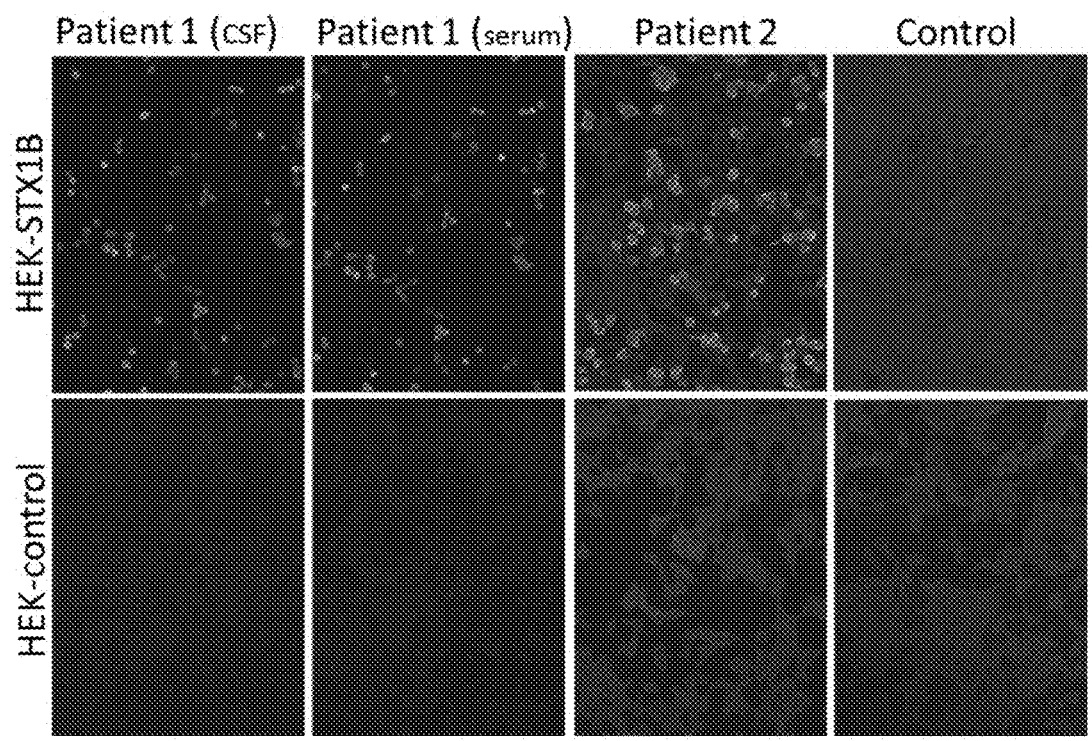
Figure 3B:
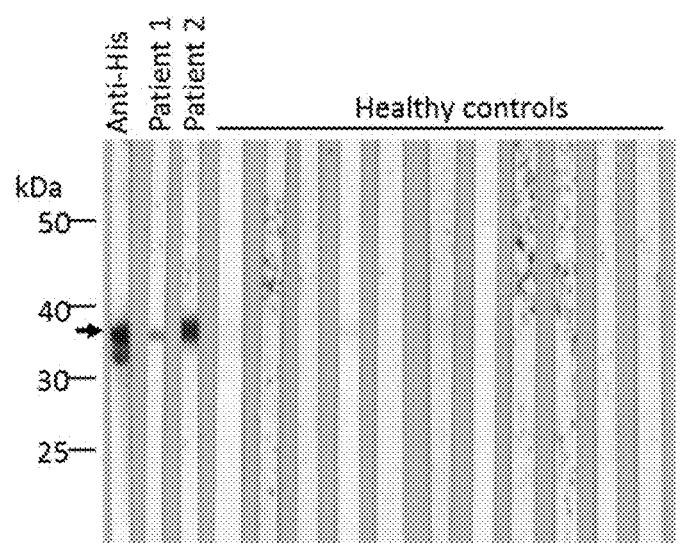

The immunoprecipitate from homogenized rat cerebellum obtained with P1 and P2 presented a protein of approximately 33 kDa in Coomassie-stained SDS-PAGE which was absent if the homogenates were incubated with control sera (FIG. 2A). Using MALDI-TOF MS, the protein was identified as STX1B (UNIPROT acc. #P61265). As a proof for correct antigen identification, immunoprecipitates were tested by Western blot using antibodies against STX1B. The immunoprecipitates of the patients' sera contained STX1B as demonstrated by a 33 kDa band (FIG. 2B). Furthermore, the patients' samples were tested by IFA using transfected HEK293 cells which expressed STX1B (SEQ ID NO: 4) (FIG. 3A). Patients' sera and CSFs reacted with the STX1B-expressing cells. In contrast, mock-transfected cell did not demonstrate any specific antibody binding. Both samples also reacted with recombinant His-STX1B in immunoblot using STX1B(ic)-His (SEQ ID NO: 5) (FIG. 3B).

Figure 3C:
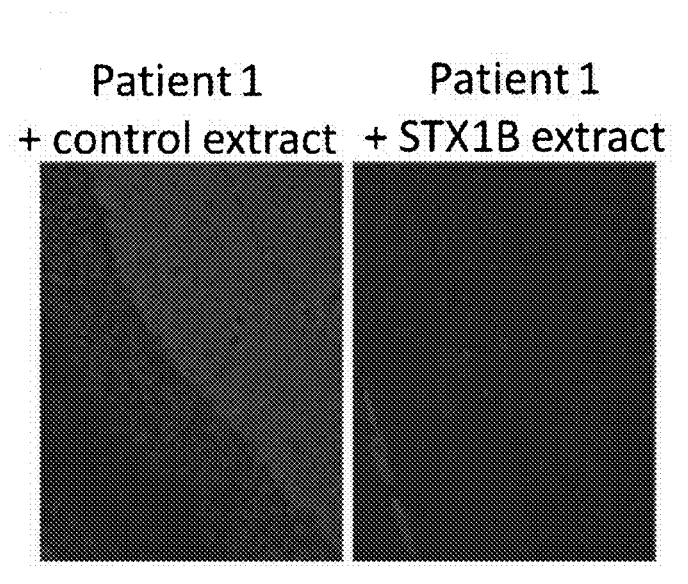

The reaction of the patients' auto-antibodies on tissue could be abolished by pre-incubation with HEK293 lysate containing STX1B (SEQ ID NO: 4) (FIG. 3C). Antibody binding was unaffected when a comparable fraction from mock-transfected HEK293 cells was used.

Specificity of anti-STX1B auto-antibodies

Sera from 33 patients with various neural auto-antibody-associated neurological syndromes (3× anti-CASPR2, 3× anti-NMDAR, 3× anti-LGI1, 3× anti-Hu, 3× anti-Ri, 2× anti-Yo/anti-Ri, 3× anti-Yo, 3× anti-AQP4, 10× anti-GAD65), 10 sera with a similar staining pattern as patient 1 and 2 on cerebellum without known anti-neural autoantibody reactivity and 45 healthy controls were analyzed by IFA with HEK293-STX1B-His in parallel to the samples of the patients. None of the healthy control sera produced a similar immunofluorescence pattern as the patients' sera on rat brain tissue, and all were all negative when tested on HEK293 cells expressing STX1B. Two of the 10 anti-GAD65 positive sera which were pre-diagnosed with stiff person syndrome (P6, P7) and two (P3, P4) of the 10 sera with a similar staining pattern as patient 1 and 2 on cerebellum were positive in IFA and Western blot with recombinant STX1B (FIG. 4).

Reactivity Against Other SNARE Complex Proteins

Figure 4A:
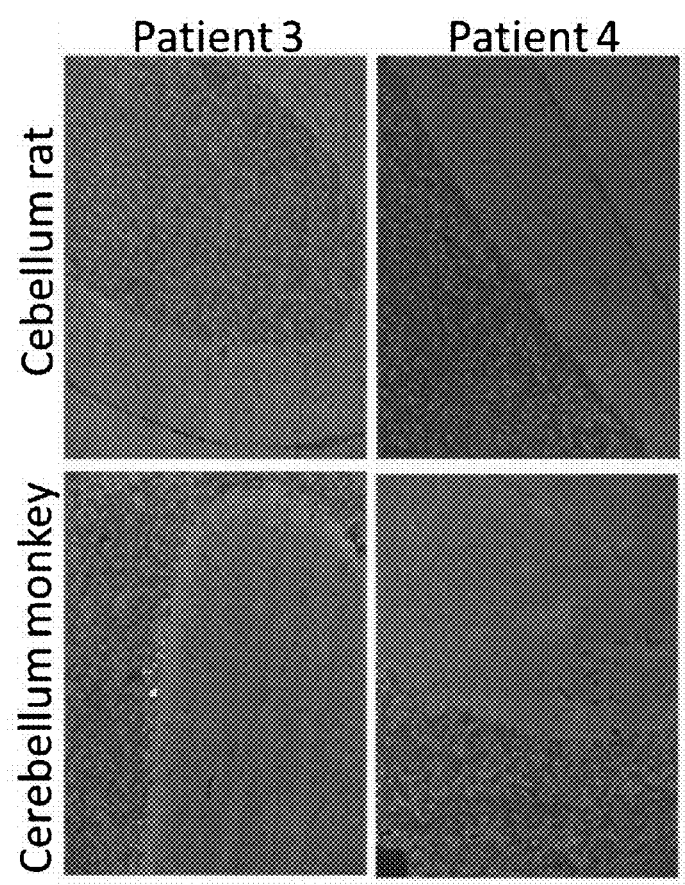
FIGS. 4A-4C shows the determination of anti-STX1B by IFA and WB. Indirect immunofluorescence using (FIG. 4A) cryosections incubated with patient sera (1:32) or (FIG. 4B) acetone-fixed STX1B or mock-transfected HEK293 cells incubated with patient serum (1:10) in the first step, and with Alexa488-labelled goat anti-human IgG in the second step.
Figure 4B:
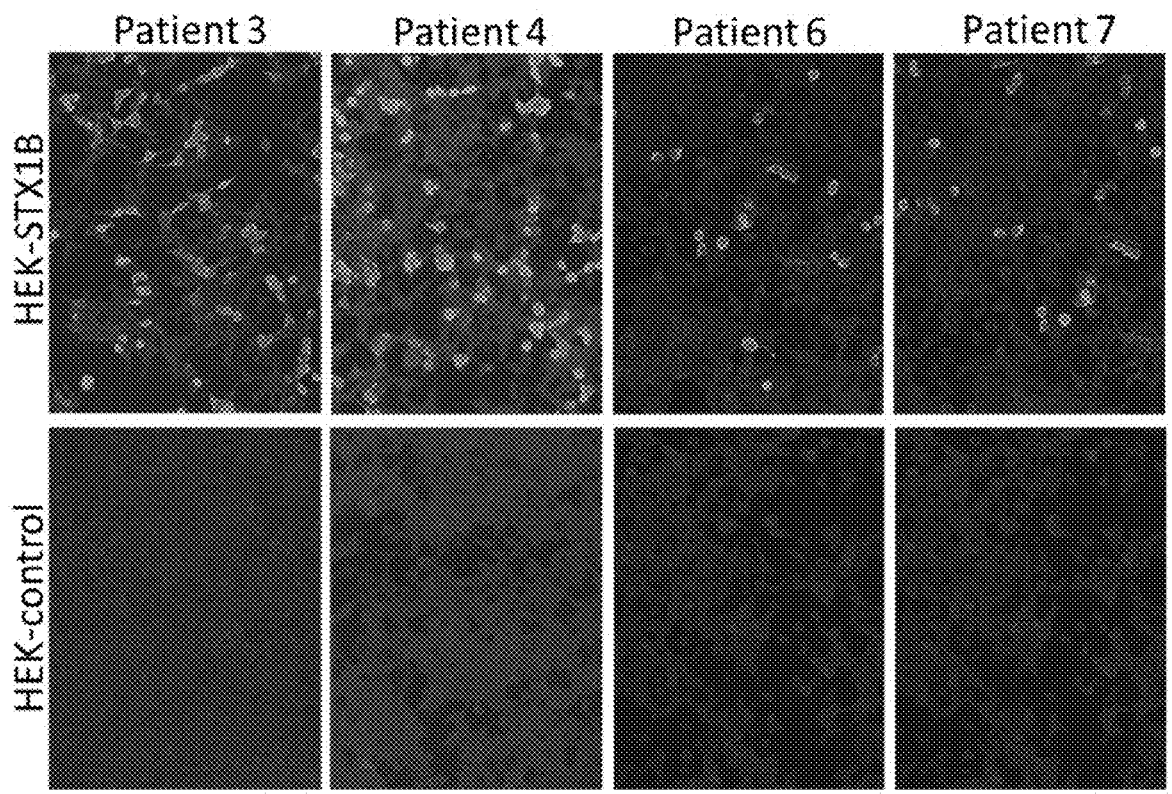
Figure 4C:
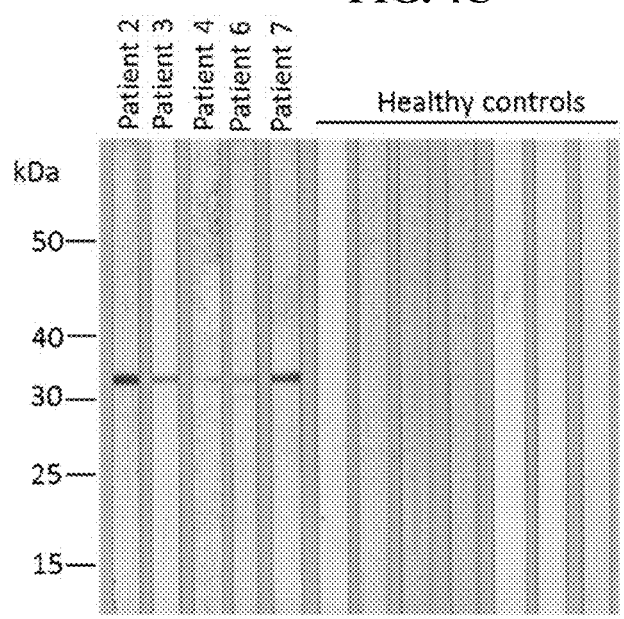
Figure 5:
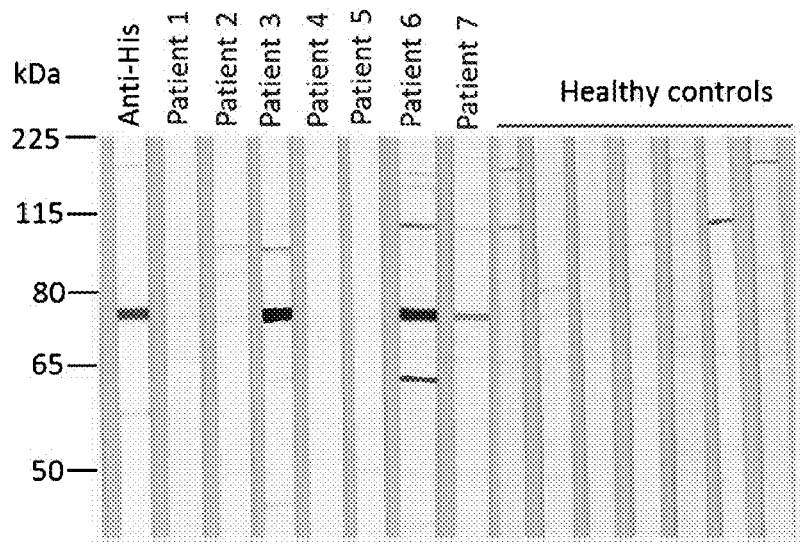
FIG. 5 shows the verification of NSF as the novel autoantigen by Western blot with the recombinant antigen. Western blot with NSF transfected HEK293 cell extract incubated with anti-His, patient sera or healthy control sera (1:1000).

Screening of anti-STX1B positive and additional sera from patients under suspicion of having and autoimmune encephalitis characterized by producing similar IFA patterns as the index sera or sera of patients with neurological symptoms and defined anti-neural autoantibodies by IFA or Western blot using transfected HEK293 cells recombinantly expressing NSF (SEQ ID NO: 2) and VAMP2 (SEQ ID NO: 7) revealed three anti-NSF (P3, P6, P7) positive (FIG. 5) and one anti-VAMP2 (P5) positive sample (FIG. 6B). Mock-transfected cells did not demonstrate any specific antibody binding. P3 and P5 produced a similar immunofluorescence pattern as the index patients' sera (P1, P2) on rat brain tissue (FIG. 4A and FIG. 6A). P6 and P7 were anti-GAD65 positive and diagnosed with stiff person syndrome. The three anti-NSF-positive sera (P3, P6, P7) were also anti-STX1B positive (FIGS. 4A-4C). None of the 45 healthy controls showed a positive reaction against NSF and VAMP2, respectively.

Immunoprecipitation of Dynamin 1 from the cerebellum by the patients' sera

An immunoprecipitation analysis using the patients' sera and the pig cerebellum lysate was implemented to identify additional target auto-antigens. The total protein concentration of the pig cerebellum lysate as determined by the BCA assay (section 2.2.2) was ≈20-23 mg/ml during every preparation.

Figure 7:
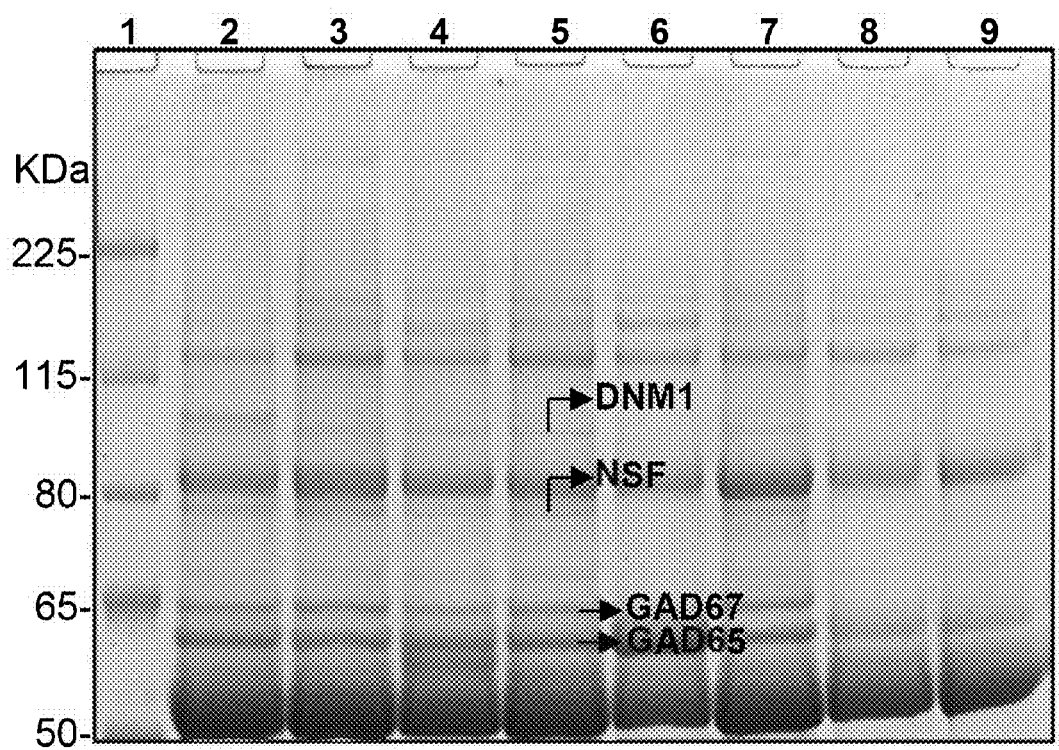
FIG. 7 shows an image of a blue silver stained gel following total lysate immunoprecipitation to demonstrate pull-down of DNM1 by patients' sera.

The analysis was performed by total lysate immunoprecipitation. The immunoprecipitated proteins were then resolved by gel electrophoresis and stained with blue silver stain to identify bands unique to the sera from patients compared with controls, which were subsequently identified by MS. An image of a blue silver stained gel following total lysate immunoprecipitation is shown in FIG. 7.

In this experiment, sera from six patients positive for anti-GAD65 and -GAD67 AAbs compared with two healthy controls were included. Following staining of the gel, the pull down of the primary target antigens GAD65 and GAD67 at positions ≈65 kDa and ≈67 kDa, respectively, was observed in all patients' sera lanes (FIG. 7, line arrows), but not in the sera from controls. Additionally, another band unique to the patients' sera lanes was identified as dynamin 1 (DNM1) at positions ≈97 kDa, (FIG. 7, elbow arrow).

Figure 8:
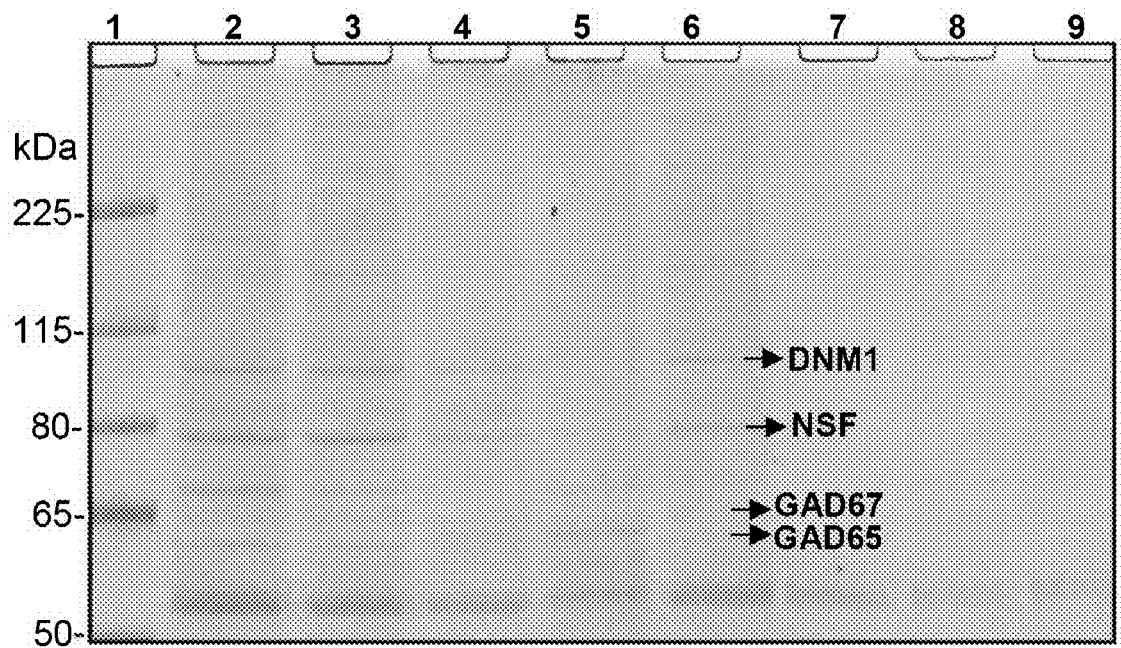
FIG. 8 shows an image of a blue silver stained gel to show pull-down of DNM1 following cryo-immunoprecipitation.

This result was verified by the second immunoprecipitation method, namely cryo-immunoprecipitation. In this method, the pig cerebellum cryosections were used instead of a tissue lysate. Comparable to the above method, the immunoprecipitated proteins were resolved in a gel and stained with blue silver stain (FIG. 8). In this experiment, four patients' sera positive and one negative for anti-GAD65 and -GAD67 AAbs in addition to three sera from healthy controls were included for representation purposes. The results from the two immunoprecipitation methods were comparable. A strong pull-down of DNM1 (≈97 kDa) was observed in all anti-GAD AAb positive patients' sera (FIG. 8, arrow), except one, wherein the pull-down was weaker (FIG. 8, lane 5). Additionally, there was no pull-down of DNM1 with the healthy controls. The patient serum negative for the pull-down of DNM1 in total lysate immunoprecipitation (FIG. 7, lane 6) was also negative in this test.

Figure 9:
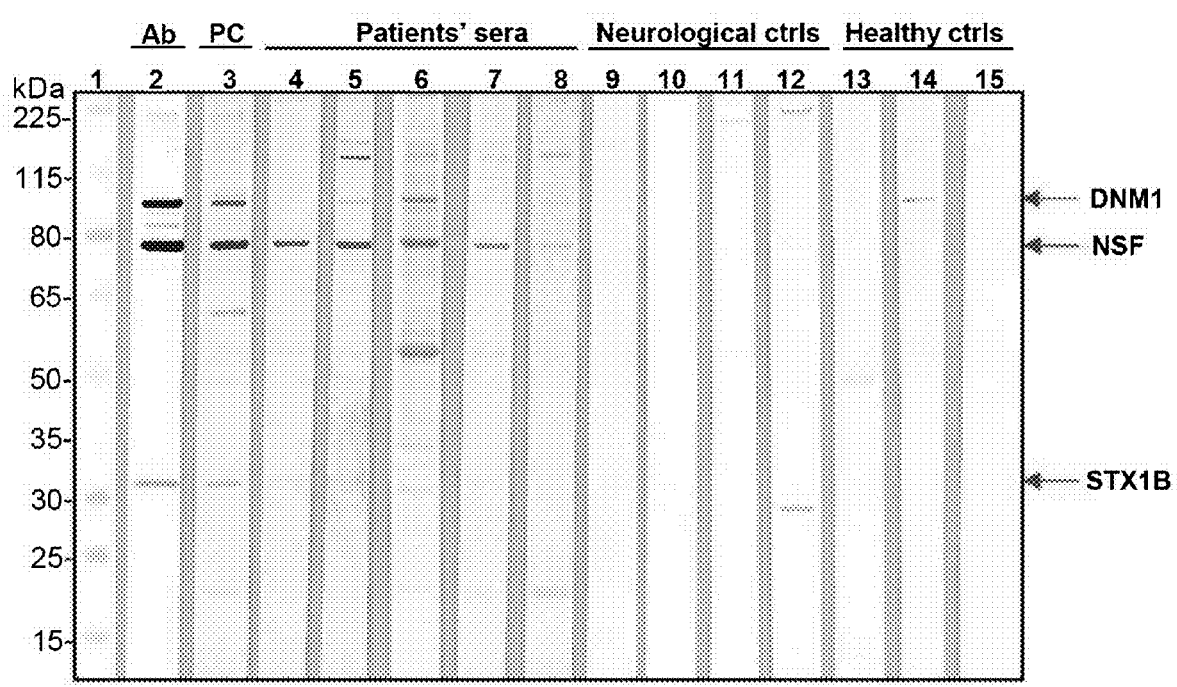
FIG. 9 shows that patients' sera demonstrate reactivity against DNM1 enriched from cerebellum.
Figure 10:
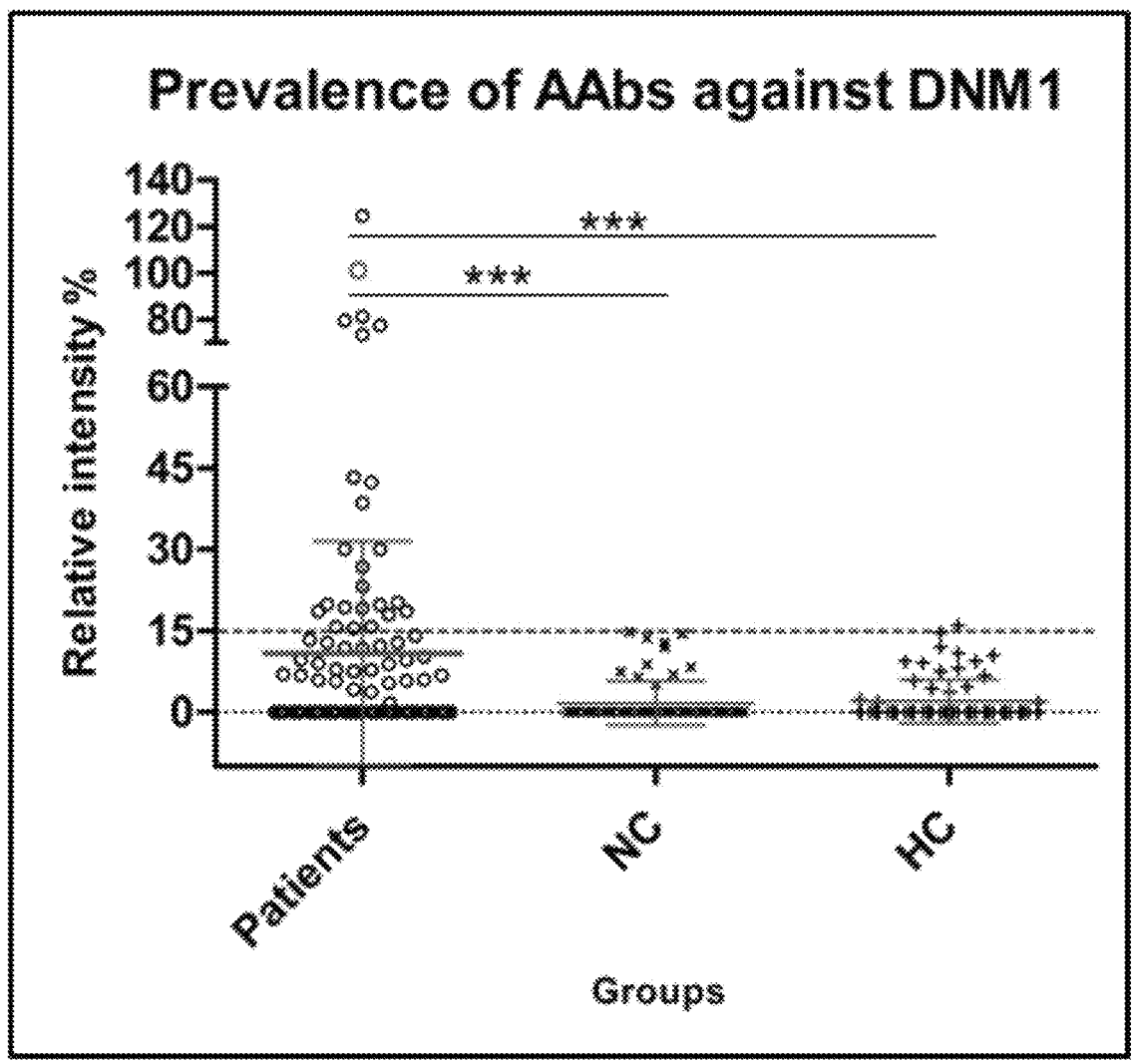
FIG. 10 shows that a patient cohort portrayed a significantly higher prevalence of AAbs against DNM1 compared with controls.

Detection of AAbs Against Cerebellar Enriched DNM1 by Immunoblotting with the Patients' Sera IMAC enriched SNARE protein fractions were separated by gel electrophoresis and transferred onto a nitrocellulose membrane. Results of the experiment are shown in FIG. 9. The membrane was cut vertically into strips and incubated with an antibody mixture containing anti-DNM1 (1:1000), anti-NSF (1:1000), and anti-STX1B (1:2000) (Ab, lane 2), an internal reference patient serum (1:350) from Euroimmun AG that was positive for AAbs against GAD, NSF, and STX1B as the positive control (PC, lane 3), and a panel of sera (1:350) from the patients (lanes: 4-8) versus neurological (lanes: 9-12) and healthy (lanes: 13-15) controls. The internal reference serum was immunoreactive against NSF and STX1B in the cell-based assays (data not shown). Reactivities against DNM1 (≈97 kDa), NSF (≈82 kDa), and STX1B 33 kDa) were observed with the antibody and the reference serum (lanes: 2 and 3, red arrows). Furthermore, patients' sera portrayed reactivity against DNM1 (lanes: 4-8). No neurological controls (lanes: 9-12) or healthy controls, except one (lane 14), portrayed any reactivity against DNM1.

Enriched fractions of DNM1 were resolved in gels and immunoblotted with patient's sera (n=100) versus neurological (n=65) and healthy (n=70) controls. The relative intensity of each band was normalized against that of a reference serum and was expressed as a percentage of the obtained relative intensity. The values were compared by implementing Kruskal-Wallis test followed by Dunn's multiple comparisons using the Graph Pad prism 5 software. The reference serum (second upper dot) was assigned a value of 100 and a cutoff of 3 SD above the mean of healthy controls was calculated (dashed line; relative intensity: ~15%) for screening purposes alone. In total, 23 patients' sera in the patient cohort, 0 patients' sera in the neurological control (NC), and 1 subject in the healthy control (HC), exhibited relative intensity values above the cutoff for DNM1 (15%). Therefore, the prevalence of AAbs against DNM1 is significantly higher in the patient cohort compared with the control groups (***$p<0.0001$). Graphs represent mean±SD of each group.

Amongst the patients' sera positive for AAbs against DNM1, the number of patients' sera positive for anti-GAD AAbs was 15. Remarkably, eight patients' sera that were negative for anti-GAD AAbs were positive for AAbs against DNM1. Altogether, patients' positive for anti-GAD AAbs might have a higher prevalence for AAbs against DNM1 compared to those negative for anti-GAD AAbs. Values from patients' having no anti-GAD AAbs were lower but not negative. With respect to individual disorders, the prevalence of AAbs against DNM1 was higher in patients with SPS, PERM, and cerebellitis compared with other associated movement disorders.

The invention claimed is:

1. A method for determining the presence or absence of an autoantibody that binds to a syntaxin 1B (STX1B) in a sample of a patient, comprising:
   (a) contacting the sample of the patient that comprises autoantibodies with the STX1B, and
   (b) determining the presence or absence of the autoantibody in the sample.

2. The method of claim 1, wherein the patient has a disease that is associated with one or more symptoms selected from the group consisting of progressive stiffness in truncal muscles, progressive stiffness in proximal leg, rigid gait, lumbar hyperlordosis, chronic pain, spasms in proximal limb and axial muscles, sensitivity to touch and sound, hyperekplexia, myoclonus, depression, anxiety, phobia, fever, headache, confusion, dysarthria, dysphagia, nystagmus, oscillopsia, vertigo, nausea, ataxia, dizziness, seizures, epilepsy and tremor.

3. The method of claim 1, wherein the sample is a bodily fluid comprising autoantibodies.

4. The method of claim 1, wherein step (b) comprises performing a technique or assay selected from the group consisting of immunodiffusion techniques, immunoelectrophoretic techniques, light scattering immunoassays, agglutination techniques, labeled immunoassays, radiolabeled immunoassay, enzyme immunoassays, chemiluminscence immunoassays, and immunofluorescence.

5. The method of claim 2, wherein the disease is associated with two or more of the symptoms.

6. The method of claim 2, wherein the truncal muscles include thoracolumbar paraspinal muscles, abdominal muscles, or abdominal wall muscles.

7. The method of claim 3, wherein the bodily fluid is selected from the group consisting of whole blood, serum, cerebrospinal fluid and saliva.

8. The method of claim 4, wherein the enzyme immunoassay is enzyme-linked immunosorbent assay (ELISA).

9. The method of claim 4, wherein the immunofluorescence is indirect immunofluorescence.

10. The method of claim 2, wherein the disease is a neurological disease.

11. The method of claim 10, wherein the disease is an autoimmune disease of the nervous system selected from the group consisting of stiff-person syndrome, paraneoplastic stiff-person syndrome, progressive encephalomyelitis with rigidity and myoclonus encephalitis, and encephalitis.

* * * * *

SEQUENCE LISTING

<160> NUMBER OF SEQ ID NOS: 20

<210> SEQ ID NO 1
<211> LENGTH: 744
<212> TYPE: PRT
<213> ORGANISM: Artificial Sequence
<220> FEATURE:
<223> OTHER INFORMATION: SEQ ID NO 1 (NSF, UNIPROT)

<400> SEQUENCE: 1

```
Met Ala Gly Arg Ser Met Gln Ala Ala Arg Cys Pro Thr Asp Glu Leu
1               5                   10                  15

Ser Leu Thr Asn Cys Ala Val Val Asn Glu Lys Asp Phe Gln Ser Gly
            20                  25                  30

Gln His Val Ile Val Arg Thr Ser Pro Asn His Arg Tyr Thr Phe Thr
        35                  40                  45

Leu Lys Thr His Pro Ser Val Val Pro Gly Ser Ile Ala Phe Ser Leu
    50                  55                  60
```

-continued

```
Pro Gln Arg Lys Trp Ala Gly Leu Ser Ile Gly Gln Glu Ile Glu Val
 65                  70                  75                  80

Ser Leu Tyr Thr Phe Asp Lys Ala Lys Gln Cys Ile Gly Thr Met Thr
                 85                  90                  95

Ile Glu Ile Asp Phe Leu Gln Lys Lys Ser Ile Asp Ser Asn Pro Tyr
            100                 105                 110

Asp Thr Asp Lys Met Ala Ala Glu Phe Ile Gln Gln Phe Asn Asn Gln
        115                 120                 125

Ala Phe Ser Val Gly Gln Gln Leu Val Phe Ser Phe Asn Glu Lys Leu
130                 135                 140

Phe Gly Leu Leu Val Lys Asp Ile Glu Ala Met Asp Pro Ser Ile Leu
145                 150                 155                 160

Lys Gly Glu Pro Ala Thr Gly Lys Arg Gln Lys Ile Glu Val Gly Leu
                165                 170                 175

Val Val Gly Asn Ser Gln Val Ala Phe Glu Lys Ala Glu Asn Ser Ser
            180                 185                 190

Leu Asn Leu Ile Gly Lys Ala Lys Thr Lys Glu Asn Arg Gln Ser Ile
        195                 200                 205

Ile Asn Pro Asp Trp Asn Phe Glu Lys Met Gly Ile Gly Gly Leu Asp
210                 215                 220

Lys Glu Phe Ser Asp Ile Phe Arg Arg Ala Phe Ala Ser Arg Val Phe
225                 230                 235                 240

Pro Pro Glu Ile Val Glu Gln Met Gly Cys Lys His Val Lys Gly Ile
                245                 250                 255

Leu Leu Tyr Gly Pro Pro Gly Cys Gly Lys Thr Leu Leu Ala Arg Gln
            260                 265                 270

Ile Gly Lys Met Leu Asn Ala Arg Glu Pro Lys Val Val Asn Gly Pro
        275                 280                 285

Glu Ile Leu Asn Lys Tyr Val Gly Glu Ser Glu Ala Asn Ile Arg Lys
290                 295                 300

Leu Phe Ala Asp Ala Glu Glu Gln Arg Arg Leu Gly Ala Asn Ser
305                 310                 315                 320

Gly Leu His Ile Ile Ile Phe Asp Glu Ile Asp Ala Ile Cys Lys Gln
                325                 330                 335

Arg Gly Ser Met Ala Gly Ser Thr Gly Val His Asp Thr Val Val Asn
            340                 345                 350

Gln Leu Leu Ser Lys Ile Asp Gly Val Glu Gln Leu Asn Asn Ile Leu
        355                 360                 365

Val Ile Gly Met Thr Asn Arg Pro Asp Leu Ile Asp Glu Ala Leu Leu
370                 375                 380

Arg Pro Gly Arg Leu Glu Val Lys Met Glu Ile Gly Leu Pro Asp Glu
385                 390                 395                 400

Lys Gly Arg Leu Gln Ile Leu His Ile His Thr Ala Arg Met Arg Gly
                405                 410                 415

His Gln Leu Leu Ser Ala Asp Val Asp Ile Lys Glu Leu Ala Val Glu
            420                 425                 430

Thr Lys Asn Phe Ser Gly Ala Glu Leu Glu Gly Leu Val Arg Ala Ala
        435                 440                 445

Gln Ser Thr Ala Met Asn Arg His Ile Lys Ala Ser Thr Lys Val Glu
450                 455                 460

Val Asp Met Glu Lys Ala Glu Ser Leu Gln Val Thr Arg Gly Asp Phe
465                 470                 475                 480

Leu Ala Ser Leu Glu Asn Asp Ile Lys Pro Ala Phe Gly Thr Asn Gln
```

```
            485                 490                 495
Glu Asp Tyr Ala Ser Tyr Ile Met Asn Gly Ile Ile Lys Trp Gly Asp
            500                 505                 510

Pro Val Thr Arg Val Leu Asp Asp Gly Glu Leu Leu Val Gln Gln Thr
        515                 520                 525

Lys Asn Ser Asp Arg Thr Pro Leu Val Ser Val Leu Leu Glu Gly Pro
    530                 535                 540

Pro His Ser Gly Lys Thr Ala Leu Ala Ala Lys Ile Ala Glu Glu Ser
545                 550                 555                 560

Asn Phe Pro Phe Ile Lys Ile Cys Ser Pro Asp Lys Met Ile Gly Phe
                565                 570                 575

Ser Glu Thr Ala Lys Cys Gln Ala Met Lys Lys Ile Phe Asp Asp Ala
            580                 585                 590

Tyr Lys Ser Gln Leu Ser Cys Val Val Val Asp Asp Ile Glu Arg Leu
        595                 600                 605

Leu Asp Tyr Val Pro Ile Gly Pro Arg Phe Ser Asn Leu Val Leu Gln
    610                 615                 620

Ala Leu Leu Val Leu Leu Lys Lys Ala Pro Pro Gln Gly Arg Lys Leu
625                 630                 635                 640

Leu Ile Ile Gly Thr Thr Ser Arg Lys Asp Val Leu Gln Glu Met Glu
                645                 650                 655

Met Leu Asn Ala Phe Ser Thr Thr Ile His Val Pro Asn Ile Ala Thr
            660                 665                 670

Gly Glu Gln Leu Leu Glu Ala Leu Glu Leu Leu Gly Asn Phe Lys Asp
        675                 680                 685

Lys Glu Arg Thr Thr Ile Ala Gln Gln Val Lys Gly Lys Lys Val Trp
    690                 695                 700

Ile Gly Ile Lys Lys Leu Leu Met Leu Ile Glu Met Ser Leu Gln Met
705                 710                 715                 720

Asp Pro Glu Tyr Arg Val Arg Lys Phe Leu Ala Leu Leu Arg Glu Glu
                725                 730                 735

Gly Ala Ser Pro Leu Asp Phe Asp
            740

<210> SEQ ID NO 2
<211> LENGTH: 744
<212> TYPE: PRT
<213> ORGANISM: Artificial Sequence
<220> FEATURE:
<223> OTHER INFORMATION: SEQ ID NO 2 (NSF, REC)

<400> SEQUENCE: 2

Met Ala Gly Arg Ser Met Gln Ala Ala Arg Cys Pro Thr Asp Glu Leu
1               5                   10                  15

Ser Leu Thr Asn Cys Ala Val Val Asn Glu Lys Asp Phe Gln Ser Gly
            20                  25                  30

Gln His Val Ile Val Arg Thr Ser Pro Asn His Arg Tyr Thr Phe Thr
        35                  40                  45

Leu Lys Thr His Pro Ser Val Val Pro Gly Ser Ile Ala Phe Ser Leu
    50                  55                  60

Pro Gln Arg Lys Trp Ala Gly Leu Ser Ile Gly Gln Glu Ile Glu Val
65                  70                  75                  80

Ser Leu Tyr Thr Phe Asp Lys Ala Lys Gln Cys Ile Gly Thr Met Thr
                85                  90                  95

Ile Glu Ile Asp Phe Leu Gln Lys Lys Ser Ile Asp Ser Asn Pro Tyr
```

```
            100             105             110
Asp Thr Asp Lys Met Ala Ala Glu Phe Ile Gln Gln Phe Asn Asn Gln
        115             120             125

Ala Phe Ser Val Gly Gln Gln Leu Val Phe Ser Phe Asn Glu Lys Leu
        130             135             140

Phe Gly Leu Leu Val Lys Asp Ile Glu Ala Met Asp Pro Ser Ile Leu
145             150             155             160

Lys Gly Glu Pro Ala Thr Gly Lys Arg Gln Lys Ile Glu Val Gly Leu
            165             170             175

Val Val Gly Asn Ser Gln Val Ala Phe Glu Lys Ala Glu Asn Ser Ser
            180             185             190

Leu Asn Leu Ile Gly Lys Ala Lys Thr Lys Glu Asn Arg Gln Ser Ile
        195             200             205

Ile Asn Pro Asp Trp Asn Phe Glu Lys Met Gly Ile Gly Gly Leu Asp
        210             215             220

Lys Glu Phe Ser Asp Ile Phe Arg Arg Ala Phe Ala Ser Arg Val Phe
225             230             235             240

Pro Pro Glu Ile Val Glu Gln Met Gly Cys Lys His Val Lys Gly Ile
            245             250             255

Leu Leu Tyr Gly Pro Pro Gly Cys Gly Lys Thr Leu Leu Ala Arg Gln
            260             265             270

Ile Gly Lys Met Leu Asn Ala Arg Glu Pro Lys Val Val Asn Gly Pro
        275             280             285

Glu Ile Leu Asn Lys Tyr Val Gly Glu Ser Glu Ala Asn Ile Arg Lys
        290             295             300

Leu Phe Ala Asp Ala Glu Glu Gln Arg Arg Leu Gly Ala Asn Ser
305             310             315             320

Gly Leu His Ile Ile Phe Asp Glu Ile Asp Ala Ile Cys Lys Gln
            325             330             335

Arg Gly Ser Met Ala Gly Ser Thr Gly Val His Asp Thr Val Val Asn
            340             345             350

Gln Leu Leu Ser Lys Ile Asp Gly Val Glu Gln Leu Asn Asn Ile Leu
        355             360             365

Val Ile Gly Met Thr Asn Arg Pro Asp Leu Ile Asp Glu Ala Leu Leu
        370             375             380

Arg Pro Gly Arg Leu Glu Val Lys Met Glu Ile Gly Leu Pro Asp Glu
385             390             395             400

Lys Gly Arg Leu Gln Ile Leu His Ile His Thr Ala Arg Met Arg Gly
            405             410             415

His Gln Leu Leu Ser Ala Asp Val Asp Ile Lys Glu Leu Ala Val Glu
            420             425             430

Thr Lys Asn Phe Ser Gly Ala Glu Leu Glu Gly Leu Val Arg Ala Ala
        435             440             445

Gln Ser Thr Ala Met Asn Arg His Ile Lys Ala Ser Thr Lys Val Glu
        450             455             460

Val Asp Met Glu Lys Ala Glu Ser Leu Gln Val Thr Arg Gly Asp Phe
465             470             475             480

Leu Ala Ser Leu Glu Asn Asp Ile Lys Pro Ala Phe Gly Thr Asn Gln
            485             490             495

Glu Asp Tyr Ala Ser Tyr Ile Met Asn Gly Ile Ile Lys Trp Gly Asp
            500             505             510

Pro Val Thr Arg Val Leu Asp Asp Gly Glu Leu Leu Val Gln Gln Thr
        515             520             525
```

```
Lys Asn Ser Asp Arg Thr Pro Leu Val Ser Val Leu Leu Glu Gly Pro
    530                 535                 540

Pro His Ser Gly Lys Thr Ala Leu Ala Ala Lys Ile Ala Glu Glu Ser
545                 550                 555                 560

Asn Phe Pro Phe Ile Lys Ile Cys Ser Pro Asp Lys Met Ile Gly Phe
                565                 570                 575

Ser Glu Thr Ala Lys Cys Gln Ala Met Lys Lys Ile Phe Asp Asp Ala
            580                 585                 590

Tyr Lys Ser Gln Leu Ser Cys Val Val Val Asp Asp Ile Glu Arg Leu
        595                 600                 605

Leu Asp Tyr Val Pro Ile Gly Pro Arg Phe Ser Asn Leu Val Leu Gln
    610                 615                 620

Ala Leu Leu Val Leu Leu Lys Lys Ala Pro Pro Gln Gly Arg Lys Leu
625                 630                 635                 640

Leu Ile Ile Gly Thr Thr Ser Arg Lys Asp Val Leu Gln Glu Met Glu
                645                 650                 655

Met Leu Asn Ala Phe Ser Thr Thr Ile His Val Pro Asn Ile Ala Thr
            660                 665                 670

Gly Glu Gln Leu Leu Glu Ala Leu Glu Leu Leu Gly Asn Phe Lys Asp
        675                 680                 685

Lys Glu Arg Thr Thr Ile Ala Gln Gln Val Lys Gly Lys Lys Val Trp
    690                 695                 700

Ile Gly Ile Lys Lys Leu Leu Met Leu Ile Glu Met Ser Leu Gln Met
705                 710                 715                 720

Asp Pro Glu Tyr Arg Val Arg Lys Phe Leu Ala Leu Leu Arg Glu Glu
                725                 730                 735

Gly Ala Ser Pro Leu Asp Phe Asp
            740

<210> SEQ ID NO 3
<211> LENGTH: 288
<212> TYPE: PRT
<213> ORGANISM: Artificial Sequence
<220> FEATURE:
<223> OTHER INFORMATION: SEQ ID NO 3 (STX1B, UNIPROT)

<400> SEQUENCE: 3

Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140
```

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
            165                 170                 175

Thr Asp Asp Ile Lys Met Asp Ser Gln Met Thr Lys Gln Ala Leu Asn
        180                 185                 190

Glu Ile Glu Thr Arg His Asn Glu Ile Ile Lys Leu Glu Thr Ser Ile
    195                 200                 205

Arg Glu Leu His Asp Met Phe Val Asp Met Ala Met Leu Val Glu Ser
210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
            245                 250                 255

Gln Ser Lys Ala Arg Arg Lys Lys Ile Met Ile Ile Cys Cys Val
        260                 265                 270

Val Leu Gly Val Val Leu Ala Ser Ser Ile Gly Gly Thr Leu Gly Leu
        275                 280                 285

<210> SEQ ID NO 4
<211> LENGTH: 288
<212> TYPE: PRT
<213> ORGANISM: Artificial Sequence
<220> FEATURE:
<223> OTHER INFORMATION: SEQ ID NO 4 (STX1B, REC)

<400> SEQUENCE: 4

Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
            245                 250                 255

Gln Ser Lys Ala Arg Arg Lys Ile Met Ile Ile Cys Cys Val
        260                 265                 270

Val Leu Gly Val Val Leu Ala Ser Ser Ile Gly Gly Thr Leu Gly Leu
        275                 280                 285

<210> SEQ ID NO 5
<211> LENGTH: 274
<212> TYPE: PRT
<213> ORGANISM: Artificial Sequence
<220> FEATURE:
<223> OTHER INFORMATION: SEQ ID NO 5 (STX1B(ic)-His, REC)

<400> SEQUENCE: 5

Met Lys Asp Arg Thr Gln Glu Leu Arg Ser Ala Lys Asp Ser Asp
1               5                   10                  15

Glu Glu Glu Val Val His Val Asp Arg Asp His Phe Met Asp Glu Phe
                20 25 30

Phe Glu Gln Val Glu Glu Ile Arg Gly Cys Ile Glu Lys Leu Ser Glu
35 40 45

Asp Val Glu Gln Val Lys Lys Gln His Ser Ala Ile Leu Ala Ala Pro
50 55 60

Asn Pro Asp Glu Lys Thr Lys Gln Glu Leu Glu Asp Leu Thr Ala Asp
65 70 75 80

Ile Lys Lys Thr Ala Asn Lys Val Arg Ser Lys Leu Lys Ala Ile Glu
85 90 95

Gln Ser Ile Glu Gln Glu Glu Gly Leu Asn Arg Ser Ser Ala Asp Leu
100 105 110

Arg Ile Arg Lys Thr Gln His Ser Thr Leu Ser Arg Lys Phe Val Glu
115 120 125

Val Met Thr Glu Tyr Asn Ala Thr Gln Ser Lys Tyr Arg Asp Arg Cys
130 135 140

Lys Asp Arg Ile Gln Arg Gln Leu Glu Ile Thr Gly Arg Thr Thr Thr
145 150 155 160

Asn Glu Glu Leu Glu Asp Met Leu Glu Ser Gly Lys Leu Ala Ile Phe
165 170 175

Thr Asp Asp Ile Lys Met Asp Ser Gln Met Thr Lys Gln Ala Leu Asn
180 185 190

Glu Ile Glu Thr Arg His Asn Glu Ile Ile Lys Leu Glu Thr Ser Ile
195 200 205

Arg Glu Leu His Asp Met Phe Val Asp Met Ala Met Leu Val Glu Ser
210 215 220

Gln Gly Glu Met Ile Asp Arg Ile Glu Tyr Asn Val Glu His Ser Val
225 230 235 240

Asp Tyr Val Glu Arg Ala Val Ser Asp Thr Lys Lys Ala Val Lys Tyr
245 250 255

Gln Ser Lys Ala Arg Arg Lys Lys Leu Glu His His His His His His
260 265 270

His His

<210> SEQ ID NO 6
<211> LENGTH: 116

<212> TYPE: PRT
<213> ORGANISM: Artificial Sequence
<220> FEATURE:
<223> OTHER INFORMATION: SEQ ID NO 6 (VAMP2, UNIPROT)

<400> SEQUENCE: 6

```
Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
        115
```

<210> SEQ ID NO 7
<211> LENGTH: 116
<212> TYPE: PRT
<213> ORGANISM: Artificial Sequence
<220> FEATURE:
<223> OTHER INFORMATION: SEQ ID NO 7 (VAMP2, REC)

<400> SEQUENCE: 7

```
Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
        115
```

<210> SEQ ID NO 8
<211> LENGTH: 33
<212> TYPE: DNA
<213> ORGANISM: Artificial Sequence
<220> FEATURE:
<223> OTHER INFORMATION: SEQ ID NO 8 (sense NSF)

<400> SEQUENCE: 8
atacgtctca catggcgggc cggagcatgc aag        33

<210> SEQ ID NO 9

```
<210> SEQ ID NO 9
<211> LENGTH: 37
<212> TYPE: DNA
<213> ORGANISM: Artificial Sequence
<220> FEATURE:
<223> OTHER INFORMATION: SEQ ID NO 9 (asense NSF)

<400> SEQUENCE: 9
tatcgtctcc tcgatcaatc aaaatcaagg gggctag                              37

<210> SEQ ID NO 10
<211> LENGTH: 36
<212> TYPE: DNA
<213> ORGANISM: Artificial Sequence
<220> FEATURE:
<223> OTHER INFORMATION: SEQ ID NO 10 (sense STX1B)

<400> SEQUENCE: 10
atacgtctca catgaaggat cggactcaag agctgc                               36

<210> SEQ ID NO 11
<211> LENGTH: 40
<212> TYPE: DNA
<213> ORGANISM: Artificial Sequence
<220> FEATURE:
<223> OTHER INFORMATION: SEQ ID NO 11 (asense STX1B)

<400> SEQUENCE: 11
atacgtctcc tcgagctaca agcccagcgt cccccccaatg                          40

<210> SEQ ID NO 12
<211> LENGTH: 39
<212> TYPE: DNA
<213> ORGANISM: Artificial Sequence
<220> FEATURE:
<223> OTHER INFORMATION: SEQ ID NO 12 (asense STX1B(ic)-His)

<400> SEQUENCE: 12
atacgtctcc tcgagtttct tcctccgggc cttgctctg                            39

<210> SEQ ID NO 13
<211> LENGTH: 36
<212> TYPE: DNA
<213> ORGANISM: Artificial Sequence
<220> FEATURE:
<223> OTHER INFORMATION: SEQ ID NO 13 (sense VAMP2)

<400> SEQUENCE: 13
atacgtctct catgtctgct accgctgcca cggccc                               36

<210> SEQ ID NO 14
<211> LENGTH: 40
<212> TYPE: DNA
<213> ORGANISM: Artificial Sequence
<220> FEATURE:
<223> OTHER INFORMATION: SEQ ID NO 14 (asense VAMP2)

<400> SEQUENCE: 14
atacgtctcc tcgagttaag tgctgaagta aactatgatg                           40

<210> SEQ ID NO 15
<211> LENGTH: 7848
<212> TYPE: DNA
<213> ORGANISM: Artificial Sequence
<220> FEATURE:
<223> OTHER INFORMATION: SEQ ID NO 15 (pTriEx-1-NSF)

<400> SEQUENCE: 15
```

```
taatacgact cactataggg gaattgtgag cggataacaa ttccccggag ttaatccggg      60
acctttaatt caacccaaca caatatatta tagttaaata agaattatta tcaaatcatt     120
tgtatattaa ttaaaatact atactgtaaa ttacatttta tttacaatca aaggagatat     180
accatggcgg gccggagcat gcaagcggca agatgtccta cagtgaatt atctttaacc     240 aattgtgcag ttgtgaatga aaaggatttc cagtctggcc agcatgtgat tgtgaggacc     300
tctcccaatc acaggtacac atttacactg aagcacatc catcggtggt tccagggagc     360
attgcattca gtttacctca gagaaaatgg gctgggcttt ctattgggca agaaatagaa     420
gtctccttat atacatttga caaagccaaa cagtgtattg gcacaatgac catcgagatt     480
gatttcctgc agaaaaaaag cattgactcc aaccttatg acaccgacaa gatggcagca     540
gaatttattc agcaattcaa caaccaggcc ttctcagtgg acaacagct tgtctttagc     600 ttcaatgaaa agcttttggg cttactggtg aaggacattg aagccatgga tcctagcatc     660
ctgaagggag agcctgcgac agggaaaagg cagaagattg aagtaggact ggttgttgga     720
aacagtcaag ttgcatttga aaaagcagaa aattcgtcac ttaatcttat tggcaaagct     780
aaaaccaagg aaaatcgcca atcaattatc aatcctgact ggaactttga aaaaatggga     840
ataggaggtc tagacaagga attttcagat attttccgac gagcatttgc ttcccgagta     900
tttcctccag agattgtgga gcagatgggt tgtaaacatg ttaaaggcat cctgttatat     960 ggaccccag gttgtggtaa gactctcttg gctcgacaga ttggcaagat gttgaatgca    1020
agagagccca aagtggtcaa tgggccagaa atccttaaca aatatgtggg agaatcagag    1080
gctaacattc gcaaactttt tgctgatgct gaagaggagc aaaggaggct tggtgctaac    1140
agtggtttgc acatcatcat ctttgatgaa attgatgcca tctgcaagca gagagggagc    1200
atggctggta gcacgggagt tcatgacact gttgtcaacc agttgctgtc caaaattgat    1260
ggcgtggagc agctaaacaa catcctagtc attggaatga ccaatagacc agatctgata    1320
gatgaggctc ttcttagacc tggaagactg gaagttaaaa tggagatagg cttgccagat    1380
gagaaaggcc gactacagat tcttcacatc cacacagcaa gaatgagagg gcatcagtta    1440
ctctctgctg atgtagacat taaagaactg gccgtggaga ccaagaattt cagtggtgct    1500
gaattggagg gtctagtgcg agcagcccag tccactgcta tgaatagaca cataaaggcc    1560
agtactaaag tggaagtgga catggagaaa gcagaaagcc tgcaagtgac gagaggagac    1620
ttccttgctt ctttggagaa tgatatcaaa ccagcctttg gcacaaacca agaagattat    1680
gcaagttaca ttatgaacgg tatcatcaaa tggggtgacc cagttactcg agttctagat    1740 gatgggagc tgctggtgca gcagactaag aacagtgacc gcacaccatt ggtcagcgtg    1800
cttctggaag gccctcctca gtgggaag actgctttag ctgcaaaaat tgcagaggaa    1860
tccaacttcc cattcatcaa gatctgttct cctgataaaa tgattggctt ttctgaaaca    1920
gccaaatgtc aggccatgaa gaagatcttt gatgatgcgt acaaatccca gctcagttgt    1980
gtggttgtgg atgacattga gagattgctt gattacgtcc ctattggccc tcgatttca    2040 aatcttgtat tacaggctct tctcgtttta ctgaaaaagg cacctcctca gggccgcaag    2100
cttcttatca ttgggaccac tagccgcaaa gatgtccttc aggagatgga aatgcttaac    2160
gctttcagca ccaccatcca cgtgcccaac attgccacag agagcagct gttggaagct    2220 ttggagcttt tgggcaactt caaggataag gaacgcacca caattgcaca gcaagtcaaa    2280
gggaagaagg tctggatagg aatcaagaag ttactaatgc tgatcgagat gtccctacag    2340
```

```
atggatcctg aataccgtgt gagaaaattc ttggccctct taagagaaga aggagctagc    2400
ccccttgatt ttgattgatc gagcaccacc atcaccatca ccatcactaa gtgattaacc    2460
tcaggtgcag gctgcctatc agaaggtggt ggctggtgtg gccaatgccc tggctcacaa    2520
ataccactga gatcgatctt tttccctctg ccaaaaatta tggggacatc atgaagcccc    2580
ttgagcatct gacttctggc taataaagga aatttatttt cattgcaata gtgtgttgga    2640
atttttgtg tctctcactc ggaaggacat atgggagggc aaatcattta aaacatcaga    2700
atgagtattt ggtttagagt ttggcaacat atgcccatat gtaactagca taaccccttg    2760
gggcctctaa acgggtcttg aggggttttt tgctgaaagc atgcggagga aattctcctt    2820
gaagtttccc tggtgttcaa agtaaaggag tttgcaccag acgcacctct gttcactggt    2880
ccggcgtatt aaaacacgat acattgttat tagtacattt attaagcgct agattctgtg    2940
cgttgttgat ttacagacaa ttgttgtacg tattttaata attcattaaa tttataatct    3000
ttagggtggt atgttagagc gaaaatcaaa tgattttcag cgtctttata tctgaattta    3060
aatattaaat cctcaataga tttgtaaaat aggtttcgat tagtttcaaa caagggttgt    3120
ttttccgaac cgatggctgg actatctaat ggattttcgc tcaacgccac aaaacttgcc    3180
aaatcttgta gcagcaatct agctttgtcg atattcgttt gtgttttgtt ttgtaataaa    3240
ggttcgacgt cgttcaaaat attatgcgct tttgtatttc tttcatcact gtcgttagtg    3300
tacaattgac tcgacgtaaa cacgttaaat agagcttgga catatttaac atcgggcgtg    3360
ttagctttat taggccgatt atcgtcgtcg tcccaaccct cgtcgttaga agttgcttcc    3420
gaagacgatt ttgccatagc cacacgacgc ctattaattg tgtcggctaa cacgtccgcg    3480
atcaaatttg tagttgagct ttttggaatt atttctgatt gcgggcgttt ttgggcgggt    3540
ttcaatctaa ctgtgcccga ttttaattca gacaacacgt tagaaagcga tggtgcaggc    3600
ggtggtaaca tttcagacgg caaatctact aatggcggcg gtggtggagc tgatgataaa    3660
tctaccatcg gtggaggcgc aggcggggct ggcggcggag gcggaggcgg aggtggtggc    3720
ggtgatgcag acggcggttt aggctcaaat gtctctttag gcaacacagt cggcacctca    3780
actattgtac tggtttcggg cgccgttttt ggtttgaccg gtctgagacg agtgcgattt    3840
ttttcgtttc taatagcttc caacaattgt tgtctgtcgt ctaaaggtgc agcgggttga    3900
ggttccgtcg gcattggtgg agcgggcggc aattcagaca tcgatggtgg tggtggtggt    3960
ggaggcgctg aatgttaggc acgggagaa ggtggtggcg gcggtgccgc cggtataatt    4020
tgttctggtt tagtttgttc gcgcacgatt gtgggcaccg cgcagggcgc cgctggctgc    4080
acaacggaag gtcgtctgct tcgaggcagc gcttggggtg gtggcaattc aatattataa    4140
ttggaataca aatcgtaaaa atctgctata agcattgtaa tttcgctatc gtttaccgtg    4200
ccgatattta acaaccgctc aatgtaagca attgtattgt aaagagattg tctcaagctc    4260
ggaacgctgc gctcggtcgt tcggctgcgg cgagcggtat cagctcactc aaaggcggta    4320
atacggttat ccacagaatc aggggataac gcaggaaaga acatgtgagc aaaaggccag    4380
caaaaggcca ggaaccgtaa aaaggccgcg ttgctggcgt ttttccatag gctccgcccc    4440
cctgacgagc atcacaaaaa tcgacgctca agtcagaggt ggcgaaaccc gacaggacta    4500
taaagatacc aggcgtttcc ccctggaagc tccctcgtgc gctctcctgt tccgaccctg    4560
ccgcttaccg gatacctgtc cgcctttctc ccttcgggaa gcgtggcgct ttctcaatgc    4620
tcacgctgta ggtatctcag ttcggtgtag gtcgttcgct ccaagctggg ctgtgtgcac    4680
gaaccccccg ttcagcccga ccgctgcgcc ttatccggta actatcgtct tgagtccaac    4740
```

```
ccggtaagac acgacttatc gccactggca gcagccactg gtaacaggat tagcagagcg    4800
aggtatgtag gcggtgctac agagttcttg aagtggtggc ctaactacgg ctacactaga    4860
aggacagtat ttggtatctg cgctctgctg aagccagtta ccttcggaaa aagagttggt    4920
agctcttgat ccggcaaaca aaccaccgct ggtagcggtg ttttttttgt ttgcaagcag    4980
cagattacgc gcagaaaaaa aggatctcaa gaagatcctt tgttaccaat gcttaatcag    5040
tgaggcacct atctcagcga tctgtctatt tcgttcatcc atagttgcct gactcccgt     5100 cgtgtagata actacgatac gggagggctt accatctggc cccagtgctg caatgatacc    5160
gcgagaccca cgctcaccgg ctccagattt atcagcaata aaccagccag ccggaagggc    5220
cgagcgcaga agtggtcctg caactttatc cgcctccatc cagtctatta attgttgccg    5280
ggaagctaga gtaagtagtt cgccagttaa tagtttgcgc aacgttgttg ccattgctac    5340
aggcatcgtg gtgtcacgct cgtcgtttgg tatggcttca ttcagctccg gttcccaacg    5400
atcaaggcga gttacatgat cccccatgtt gtgcaaaaaa gcggttagct ccttcggtcc    5460
tccgatcgtt gtcagaagta agttggccgc agtgttatca ctcatggtta tggcagcact    5520
gcataattct cttactgtca tgccatccgt aagatgcttt tctgtgactg gtgagtactc    5580
aaccaagtca ttctgagaat agtgtatgcg gcgaccgagt tgctcttgcc cggcgtcaat    5640
acgggataat accgcgccac atagcagaac tttaaaagtg ctcatcattg gaaaacgttc    5700
ttcggggcga aaactctcaa ggatcttacc gctgttgaga tccagttcga tgtaacccac    5760
tcgtgcaccc aactgatctt cagcatcttt tactttcacc agcgtttctg ggtgagcaaa    5820
aacaggaagg caaaatgccg caaaaaaggg aataagggcg acacggaaat gttgaatact    5880
catactcttc ctttttcaat attattgaag catttatcag ggttattgtc tcatgtccgc    5940
gcgtttcctg catcttttaa tcaaatccca agatgtgtat aaaccaccaa actgccaaaa    6000
aatgaaaact gtcgacaagc tctgtccgtt tgctggcaac tgcaagggtc tcaatcctat    6060
ttgtaattat tgaataataa aacaattata aatgtcaaat ttgttttta ttaacgatac     6120 aaaccaaacg caacaagaac atttgtagta ttatctataa ttgaaaacgc gtagttataa    6180
tcgctgaggt aatatttaaa atcatttca aatgattcac agttaatttg cgacaatata     6240
atttattttt cacataaact agacgccttg tcgtcttctt cttcgtattc cttctctttt    6300 tcattttct cttcataaaa attaacatag ttattatcgt atccatatat gtatctatcg     6360
tatagagtaa attttttgtt gtcataaata tatatgtctt ttttaatggg gtgtatagta    6420
ccgctgcgca tagttttttct gtaatttaca acagtgctat tttctggtag ttcttcggag    6480
tgtgttgctt taattattaa atttatataa tcaatgaatt tgggatcgtc ggttttgtac    6540
aatatgttgc cggcatagta cgcagcttct tctagttcaa ttacaccatt ttttagcagc    6600
accggattaa cataactttc caaaatgttg tacgaaccgt taaacaaaaa cagttcacct    6660
ccctttctca tactattgtc tgcgagcagt tgtttgttgt taaaaataac agccattgta    6720
atgagacgca caaactaata tcacaaactg gaaatgtcta tcaatatata gttgctctag    6780
ttattaatag taatcaatta cggggtcatt agttcatagc ccatatatgg agttccgcgt    6840
tacataactt acggtaaatg gcccgcctgg ctgaccgccc aacgacccc gcccattgac      6900 gtcaataatg acgtatgttc ccatagtaac gccaataggg actttccatt gacgtcaatg    6960
ggtggactat ttacggtaaa ctgcccactt ggcagtacat caagtgtatc atatgccaag    7020
tacgccccct attgacgtca atgacggtaa atggcccgcc tggcattatg cccagtacat    7080
```

-continued

```
gaccttatgg gactttccta cttggcagta catctacgta ttagtcatcg ctattaccat   7140
gcatggtcga ggtgagcccc acgttctgct tcactctccc catctccccc ccctccccac   7200
ccccaatttt gtatttattt atttttttaat tattttgtgc agcgatgggg gcgggggggg   7260 gggggggcg cgcgccaggc ggggcggggc ggggcgaggg gcggggcggg gcgaggcgga   7320
gaggtgcggc ggcagccaat cagagcggcg cgctccgaaa gtttcctttt atggcgaggc   7380
ggcggcggcg gcggccctat aaaaagcgaa gcgcgcggcg ggcgggagtc gctgcgacgc   7440
tgccttcgcc ccgtgccccg ctccgccgcc gcctcgcgcc gcccgccccg gctctgactg   7500
accgcgttac tcccacaggt gagcgggcgg gacggccctt ctccttcggg ctgtaattag   7560
cgcttggttt aatgacggct tgtttctttt ctgtggctgc gtgaaagcct tgaggggctc   7620
cgggagggcc ctttgtgcgg ggggagcggc tcggggctgt ccgcgggggg acggctgcct   7680
tcggggggga cggggcaggg cggggttcgg cttctggcgt gtgaccggcg gctctagagc   7740
ctctgctaac catgttcatg ccttcttctt tttcctacag ctcctgggca acgtgctggt   7800
tattgtgctg tctcatcatt ttggcaaaga attggatcgg accgaaat                7848
```

<210> SEQ ID NO 16
<211> LENGTH: 6481
<212> TYPE: DNA
<213> ORGANISM: Artificial Sequence
<220> FEATURE:
<223> OTHER INFORMATION: SEQ ID NO 16 (pTriEx-1-STX1B)

<400> SEQUENCE: 16

```
ggagtcgctg cgacgctgcc ttcgccccgt gccccgctcc gccgccgcct cgcgccgccc     60
gccccggctc tgactgaccg cgttactccc acaggtgagc gggcgggacg gcccttctcc    120
ttcgggctgt aattagcgct tggtttaatg acggcttgtt tcttttctgt ggctgcgtga    180
aagccttgag gggctccggg agggcccttt gtgcgggggg agcggctcgg ggctgtccgc    240 gggggggacgg ctgccttcgg gggggacggg gcagggcggg gttcggcttc tggcgtgtga    300
ccggcggctc tagagcctct gctaaccatg ttcatgcctt cttcttttc ctacagctcc     360 tgggcaacgt gctggttatt gtgctgtctc atcattttgg caaagaattg gatcggaccg    420
aaattaatac gactcactat aggggaattg tgagcggata acaattcccc ggagttaatc    480
cgggaccttt aattcaaccc aacacaatat attatagtta aataagaatt attatcaaat    540
catttgtata ttaattaaaa tactatactg taaattacat ttatttaca atcaaaggag     600 atataccatg aaggatcgga ctcaagagct gcggagtgcg aaagacagtg atgatgaaga    660
ggaggtggtc cacgtggatc gggaccactt catggatgag ttctttgaac aggtggaaga    720
gatccggggc tgcattgaga aactgtcgga ggatgtggag caggtgaaaa aacagcatag    780
cgccatcctg gccgcaccca acccagatga gaagaccaaa caggagctgg aggatctcac    840
tgcagacatc aagaagacgg ccaacaaggt tcggtccaaa ttgaaagcga tcgagcaaag    900
cattgaacag gaggaggggc tgaaccgttc ctccgcggac ctgcgcatcc gcaagaccca    960
gcactccaca ctgtcccgga agttcgtgga ggtaatgacc gaatataacg cgacccagtc   1020
caagtaccgg gaccgctgca aggaccggat ccagcggcaa ctggagatca ctggaaggac   1080
caccaccaac gaagaactgg aagacatgct ggagagcggg aagctggcca tcttcacaga   1140
tgacatcaaa atggactcac agatgacgaa gcaggcgctg aatgagattg agacgaggca   1200
caatgagatc atcaagctgg agaccagcat ccgcgagctg cacgatatgt ttgtggacat   1260
ggccatgctc gtagagagcc agggagagat gattgaccgc atcgagtaca acgtggaaca   1320
```

```
ttctgtggac tacgtggagc gagctgtgtc tgacaccaag aaagcagtga aatatcagag    1380
caaggcccgg aggaagaaaa tcatgatcat catttgctgt gtggtgctgg gggtggtctt    1440
ggcgtcgtcc attgggggga cgctgggctt gtagctcgag caccaccatc accatcacca    1500
tcactaagtg attaacctca ggtgcaggct gcctatcaga aggtggtggc tggtgtggcc    1560
aatgccctgg ctcacaaata ccactgagat cgatcttttt ccctctgcca aaaattatgg    1620
ggacatcatg aagccccttg agcatctgac ttctggctaa taaggaaat ttattttcat      1680 tgcaatagtg tgttggaatt ttttgtgtct ctcactcgga aggacatatg ggagggcaaa    1740
tcatttaaaa catcagaatg agtatttggt ttagagtttg caacatatg cccatatgta      1800 actagcataa cccttgggg cctctaaacg ggtcttgagg ggttttttgc tgaaagcatg       1860
cggaggaaat tctccttgaa gtttccctgg tgttcaaagt aaaggagttt gcaccagacg    1920
cacctctgtt cactggtccg gcgtattaaa acacgataca ttgttattag tacatttatt     1980
aagcgctaga ttctgtgcgt tgttgattta cagacaattg ttgtacgtat tttaataatt      2040
cattaaattt ataatcttta gggtggtatg ttagagcgaa aatcaaatga ttttcagcgt     2100
ctttatatct gaatttaaat attaaatcct caatagattt gtaaaatagg tttcgattag     2160
tttcaaacaa gggttgtttt tccgaaccga tggctggact atctaatgga ttttcgctca    2220
acgccacaaa acttgccaaa tcttgtagca gcaatctagc tttgtcgata ttcgtttgtg   2280
ttttgttttg taataaaggt tcgacgtcgt tcaaaatatt atgcgctttt gtatttcttt     2340
catcactgtc gttagtgtac aattgactcg acgtaaacac gttaaataga gcttggacat   2400
atttaacatc gggcgtgtta gctttattag gccgattatc gtcgtcgtcc caaccctcgt    2460
cgttagaagt tgcttccgaa gacgattttg ccatagccac acgacgccta ttaattgtgt   2520
cggctaacac gtccgcgatc aaatttgtag ttgagctttt tggaattatt tctgattgcg   2580 ggcgttttg ggcgggtttc aatctaactg tgcccgattt taattcagac aacacgttag    2640
aaagcgatgg tgcaggcggt ggtaacattt cagacggcaa atctactaat ggcggcggtg   2700
gtggagctga tgataaatct accatcggtg gaggcgcagg cggggctggc ggcggaggcg  2760
gaggcggagg tggtggcggt gatgcagacg gcggtttagg ctcaaatgtc tctttaggca   2820
acacagtcgg cacctcaact attgtactgg tttcgggcgc cgttttttggt ttgaccggtc   2880 tgagacgagt gcgattttttt tcgtttctaa tagcttccaa caattgttgt ctgtcgtcta   2940
aaggtgcagc gggttgaggt tccgtcggca ttggtggagc gggcggcaat tcagacatcg    3000
atggtggtgt tggtggtgga ggcgctgaa tgttaggcac gggagaaggt ggtggcggcg    3060
gtgccgccgg tataatttgt tctggtttag tttgttcgcg cacgattgtg ggcaccggcg    3120
caggcgccgc tggctgcaca acggaaggtc gtctgcttcg aggcagcgct ggggtggtg    3180 gcaattcaat attataattg gaatacaaat cgtaaaatc tgctataagc attgtaattt      3240
cgctatcgtt taccgtgccg atatttaaca accgctcaat gtaagcaatt gtattgtaaa    3300
gagattgtct caagctcgga acgctgcgct cggtcgttcg gctgcggcga gcggtatcag   3360
ctcactcaaa ggcggtaata cggttatcca cagaatcagg ggataacgca ggaaagaaca    3420
tgtgagcaaa aggccagcaa aaggccagga accgtaaaaa ggccgcgttg ctggcgtttt    3480
tccataggct ccgcccccct gacgagcatc acaaaaatcg acgctcaagt cagaggtggc    3540
gaaacccgac aggactataa agataccagg cgtttccccc tggaagctcc ctcgtgcgct    3600
ctcctgttcc gaccctgccg cttaccggat acctgtccgc ctttctccct tcgggaagcg    3660
```

```
tggcgctttc tcaatgctca cgctgtaggt atctcagttc ggtgtaggtc gttcgctcca    3720
agctgggctg tgtgcacgaa ccccccgttc agcccgaccg ctgcgcctta tccggtaact    3780
atcgtcttga gtccaacccg gtaagacacg acttatcgcc actggcagca gccactggta    3840
acaggattag cagagcgagg tatgtaggcg gtgctacaga gttcttgaag tggtggccta    3900
actacggcta cactagaagg acagtatttg gtatctgcgc tctgctgaag ccagttacct    3960
tcggaaaaag agttggtagc tcttgatccg gcaaacaaac caccgctggt agcggtggtt    4020 ttttgtttg caagcagcag attacgcgca gaaaaaagg atctcaagaa gatcctttgt    4080
taccaatgct taatcagtga ggcacctatc tcagcgatct gtctatttcg ttcatccata    4140
gttgcctgac tccccgtcgt gtagataact acgatacggg agggcttacc atctggcccc    4200
agtgctgcaa tgataccgcg agacccacgc tcaccggctc cagatttatc agcaataaac    4260
cagccagccg gaagggccga gcgcagaagt ggtcctgcaa ctttatccgc ctccatccag    4320
tctattaatt gttgccggga agctagagta agtagttcgc cagttaatag tttgcgcaac    4380
gttgttgcca ttgctacagg catcgtggtg tcacgctcgt cgtttggtat ggcttcattc    4440
agctccggtt cccaacgatc aaggcgagtt acatgatccc ccatgttgtg caaaaaagcg    4500
gttagctcct tcggtcctcc gatcgttgtc agaagtaagt tggccgcagt gttatcactc    4560
atggttatgg cagcactgca taattctctt actgtcatgc catccgtaag atgcttttct    4620
gtgactggtg agtactcaac caagtcattc tgagaatagt gtatgcggcg accgagttgc    4680
tcttgcccgg cgtcaatacg ggataatacc gcgccacata gcagaacttt aaaagtgctc    4740
atcattggaa aacgttcttc ggggcgaaaa ctctcaagga tcttaccgct gttgagatcc    4800
agttcgatgt aacccactcg tgcacccaac tgatcttcag catctttac tttcaccagc    4860 gtttctgggt gagcaaaaac aggaaggcaa aatgccgcaa aaaagggaat aagggcgaca    4920
cggaaatgtt gaatactcat actcttcctt tttcaatatt attgaagcat ttatcagggt    4980
tattgtctca tgtccgcgcg tttcctgcat cttttaatca atcccaaga tgtgtataaa    5040 ccaccaaact gccaaaaaat gaaaactgtc gacaagctct gtccgtttgc tggcaactgc    5100
aagggtctca atcctatttg taattattga ataataaaac aattataaat gtcaaatttg    5160 tttttatta acgatacaaa ccaaacgcaa caagaacatt tgtagtatta tctataattg    5220
aaaacgcgta gttataatcg ctgaggtaat atttaaaatc attttcaaat gattcacagt    5280
taatttgcga caatataatt ttattttcac ataaactaga cgccttgtcg tcttcttctt    5340
cgtattcctt ctcttttttca tttttctctt cataaaaatt aacatagtta ttatcgtatc    5400
catatatgta tctatcgtat agagtaaatt ttttgttgtc ataaatatat atgtcttttt    5460
taatggggtg tatagtaccg ctgcgcatag ttttctgta atttacaaca gtgctatttt    5520
ctggtagttc ttcggagtgt gttgctttaa ttattaaatt tatataatca atgaatttgg    5580
gatcgtcggt tttgtacaat atgttgccgg catagtacgc agcttcttct agttcaatta    5640
caccattttt tagcagcacc ggattaacat aactttccaa aatgttgtac gaaccgttaa    5700
acaaaaacag ttcacctccc ttttctatac tattgtctgc gagcagttgt tgttgttaa    5760 aaataacagc cattgtaatg agacgcacaa actaatatca caaactggaa atgtctatca    5820
atatatagtt gctctagtta ttaatagtaa tcaattacgg ggtcattagt tcatagccca    5880
tatatggagt tccgcgttac ataacttacg gtaaatggcc cgcctggctg accgcccaac    5940
gacccccgcc cattgacgtc aataatgacg tatgttccca tagtaacgcc aatagggact    6000
ttccattgac gtcaatgggt ggactattta cggtaaactg cccacttggc agtacatcaa    6060
```

```
gtgtatcata tgccaagtac gcccccta tt gacgtcaatg acggtaaatg gcccgcctgg      6120
cattatgccc agtacatgac cttatgggac tttcctactt ggcagtacat ctacgtatta      6180
gtcatcgcta ttaccatgca tggtcgaggt gagccccacg ttctgcttca ctctccccat      6240 ctccccccc tccccacccc caattttgta tttatttatt ttttaattat tttgtgcagc       6300 gatggggcg gggggggggg ggggcgcgc gccaggcggg gcgggcggg gcgaggggcg         6360 gggcggggcg aggcggagag gtgccggcgg agccaatcag agcggcgcgc tccgaaagtt      6420 tcctttt atg gcgaggcggc ggcggcggcg gccctataaa aagcgaagcg cgcggcgggc    6480
g                                                                      6481

<210> SEQ ID NO 17
<211> LENGTH: 6406
<212> TYPE: DNA
<213> ORGANISM: Artificial Sequence
<220> FEATURE:
<223> OTHER INFORMATION: SEQ ID NO 17 (pTriEx-1-STX1B(ic)-His)

<400> SEQUENCE: 17
ggagtcgctg cgacgctgcc ttcgcccgt gcccgctcc gccgccgcct cgcgccgccc        60
gccccggctc tgactgaccg cgttactccc acaggtgagc gggcgggacg gcccttctcc     120
ttcgggctgt aattagcgct tggtttaatg acgcttgtt tcttttctgt ggctgcgtga      180
aagccttgag gggctccggg agggccttt gtgcgggggg agcggctcgg ggctgtccgc     240
ggggggacgg ctgccttcgg gggggacggg gcagggcggg gttcggcttc tggcgtgtga   300
ccggcggctc tagagcctct gctaaccatg ttcatgcctt cttcttttc ctacagctcc    360 tgggcaacgt gctggttatt gtgctgtctc atcattttgg caaagaattg gatcggaccg   420
aaattaatac gactcactat aggggaattg tgagcggata acaattcccc ggagttaatc   480
cgggaccttt aattcaaccc aacacaatat attatagtta ataagaatt attatcaaat   540 catttgtata ttaattaaaa tactatactg taaattacat tttattttaca atcaaaggag   600 atataccatg aaggatcgga ctcaagagct gcggagtgcg aaagacagtg atgatgaaga   660
ggaggtggtc cacgtggatc gggaccactt catggatgag ttctttgaac aggtggaaga   720
gatccggggc tgcattgaga aactgtcgga ggatgtggag caggtgaaaa aacagcatag   780
cgccatcctg gccgcaccca cccagatga aagaccaaa caggagctgg aggatctcac    840
tgcagacatc aagaagacgg ccaacaaggt tcggtccaaa ttgaaagcga tcgagcaaag   900
cattgaacag gaggaggggc tgaaccgttc ctccgcggac ctgcgcatcc gcaagaccca   960
gcactccaca ctgtccccgga agttcgtgga ggtaatgacc gaatataacg cgacccagtc  1020
caagtaccgg gaccgctgca aggaccggat ccagcggcaa ctggagatca ctggaaggac   1080
caccaccaac gaagaactgg aagacatgct ggagagcggg aagctggcca tcttcacaga   1140
tgacatcaaa atggactcac agatgacgaa gcaggcgctg aatgagattg agacgaggca   1200
caatgagatc atcaagctgg agaccagcat ccgcgagctg cacgatatgt tgtggacat   1260 ggccatgctc gtagagagcc agggagagat gattgaccgc atcgagtaca acgtggaaca   1320
ttctgtggac tacgtggagc gagctgtgtc tgacaccaag aaagcagtga atatcagag    1380 caaggccgg aggaagaaac tcgagcacca ccatcaccat caccatcact aagtgattaa   1440
cctcaggtgc aggctgccta tcagaaggtg gtggctggtg tggccaatgc cctggctcac   1500
aaataccact gagatcgatc ttttcccctc tgccaaaaat tatgggaca tcatgaagcc   1560
```

```
ccttgagcat ctgacttctg gctaataaag gaaatttatt ttcattgcaa tagtgtgttg      1620
gaattttttg tgtctctcac tcggaaggac atatgggagg gcaaatcatt taaaacatca      1680
gaatgagtat ttggtttaga gtttggcaac atatgcccat atgtaactag cataacccct      1740
tggggcctct aaacgggtct tgaggggttt tttgctgaaa gcatgcggag gaaattctcc      1800
ttgaagtttc cctggtgttc aaagtaaagg agtttgcacc agacgcacct ctgttcactg      1860
gtccggcgta ttaaaacacg atacattgtt attagtacat ttattaagcg ctagattctg      1920
tgcgttgttg atttacagac aattgttgta cgtattttaa taattcatta aatttataat      1980 ctttaggggtg gtatgttaga gcgaaaatca aatgattttc agcgtcttta tatctgaatt      2040
taaatattaa atcctcaata gatttgtaaa ataggtttcg attagtttca aacaagggtt      2100 gttttttccga accgatggct ggactatcta atggattttc gctcaacgcc acaaaacttg      2160
ccaaatcttg tagcagcaat ctagctttgt cgatattcgt ttgtgttttg ttttgtaata      2220
aaggttcgac gtcgttcaaa atattatgcg cttttgtatt tctttcatca ctgtcgttag      2280
tgtacaattg actcgacgta aacacgttaa atagagcttg acatatttta acatcgggcg      2340
tgttagcttt attaggccga ttatcgtcgt cgtcccaacc ctcgtcgtta aagttgcttt      2400
ccgaagacga ttttgccata gccacacgac gcctattaat tgtgtcggct aacacgtccg      2460
cgatcaaatt tgtagttgag ctttttggaa ttatttctga ttgcgggcgt ttttgggcgg      2520
gtttcaatct aactgtgccc gattttaatt cagacaacac gttagaaagc gatggtgcag      2580
gcggtggtaa catttcagac ggcaaatcta ctaatggcgg cggtggtgga gctgatgata      2640
aatctaccat cggtggaggc gcaggcgggg ctggcggcgg aggcggaggc ggaggtggtg      2700
gcggtgatgc agacggcggt ttaggctcaa atgtctcttt aggcaacaca gtcggcacct      2760
caactattgt actggtttcg ggcgccgttt ttggtttgac cggtctgaga cgagtgcgat      2820
ttttttcgtt tctaatagct tccaacaatt gttgtctgtc gtctaaaggt gcagcgggtt      2880
gaggttccgt cggcattggt ggagcgggcg gcaattcaga catcgatggt ggtggtggtg      2940
gtggaggcgc tggaatgtta ggcacgggag aaggtggtgg cggcggtgcc gccggtataa      3000
tttgttctgg tttagtttgt tcgcgcacga ttgtgggcac cggcgcaggc gccgctggct      3060
gcacaacgga aggtcgtctg cttcgaggca gcgcttgggg tggtggcaat tcaatattat      3120
aattggaata caaatcgtaa aaatctgcta taagcattgt aatttcgcta tcgtttaccg      3180
tgccgatatt taacaaccgc tcaatgtaag caattgtatt gtaaagagat tgtctcaagc      3240
tcggaacgct gcgctcggtc gttcggctgc ggcgagcggt atcagctcac tcaaaggcgg      3300
taatacggtt atccacagaa tcaggggata acgcaggaaa gaacatgtga gcaaaaggcc      3360
agcaaaaggc caggaaccgt aaaaaggccg cgttgctggc gttttttccat aggctccgcc      3420 cccctgacga gcatcacaaa aatcgacgct caagtcagag gtggcgaaac ccgacaggac      3480
tataaagata ccaggcgttt ccccctggaa gctccctcgt gcgctctcct gttccgaccc      3540
tgccgcttac cggatacctg tccgcctttc tcccttcggg aagcgtggcg ctttctcaat      3600
gctcacgctg taggtatctc agttcggtgt aggtcgttcg ctccaagctg ggctgtgtgc      3660
acgaaccccc cgttcagccc gaccgctgcg ccttatccgg taactatcgt cttgagtcca      3720
acccggtaag acacgactta tcgccactgg cagcagccac tggtaacagg attagcagag      3780
cgaggtatgt aggcggtgct acagagttct tgaagtggtg gcctaactac ggctacacta      3840
gaaggacagt atttggtatc tgcgctctgc tgaagccagt taccttcgga aaaagagttg      3900
gtagctcttg atccggcaaa caaaccaccg ctggtagcgg tggtttttttt gtttgcaagc      3960
```

```
agcagattac gcgcagaaaa aaaggatctc aagaagatcc tttgttacca atgcttaatc    4020
agtgaggcac ctatctcagc gatctgtcta tttcgttcat ccatagttgc ctgactcccc    4080
gtcgtgtaga taactacgat acgggagggc ttaccatctg gccccagtgc tgcaatgata    4140
ccgcgagacc cacgctcacc ggctccagat ttatcagcaa taaaccagcc agccggaagg    4200
gccgagcgca gaagtggtcc tgcaacttta ccgcctcca tccagtctat taattgttgc     4260
cgggaagcta gagtaagtag ttcgccagtt aatagtttgc gcaacgttgt tgccattgct    4320
acaggcatcg tggtgtcacg ctcgtcgttt ggtatggctt cattcagctc cggttcccaa    4380
cgatcaaggc gagttacatg atcccccatg ttgtgcaaaa aagcggttag ctccttcggt    4440
cctccgatcg ttgtcagaag taagttggcc gcagtgttat cactcatggt tatggcagca    4500
ctgcataatt ctcttactgt catgccatcc gtaagatgct tttctgtgac tggtgagtac    4560
tcaaccaagt cattctgaga atagtgtatg cggcgaccga gttgctcttg cccggcgtca    4620
atacgggata taccgcgcc acatagcaga actttaaaag tgctcatcat tggaaaacgt     4680 tcttcgggc gaaaactctc aaggatctta ccgctgttga tccagttc gatgtaaccc       4740 actcgtgcac ccaactgatc ttcagcatct tttactttca ccagcgtttc tgggtgagca    4800
aaaacaggaa ggcaaaatgc cgcaaaaaag ggaataaggg cgacacggaa atgttgaata    4860
ctcatactct ccttttttca atattattga agcatttatc agggttattg tctcatgtcc    4920
gcgcgtttcc tgcatctttt aatcaaatcc caagatgtgt ataaaccacc aaactgccaa    4980
aaaatgaaaa ctgtcgacaa gctctgtccg tttgctggca actgcaaggg tctcaatcct    5040
atttgtaatt attgaataat aaaacaatta taatgtcaa atttgttttt tattaacgat     5100
acaaaccaaa cgcaacaaga acatttgtag tattatctat aattgaaaac gcgtagttat    5160
aatcgctgag gtaatattta aaatcatttt caaatgattc acagttaatt tgcgacaata    5220
taattttatt ttcacataaa ctagacgcct tgtcgtcttc ttcttcgtat tccttctctt    5280
tttcattttt ctcttcataa aaattaacat agttattatc gtatccatat atgtatctat    5340
cgtatagagt aaattttttg ttgtcataaa tatatatgtc tttttaatg gggtgtatag     5400 taccgctgcg catagttttt ctgtaattta caacagtgct attttctggt agttcttcgg    5460
agtgtgttgc tttaattatt aaatttatat aatcaatgaa tttgggatcg tcggttttgt    5520
acaatatgtt gccggcatag tacgcagctt cttctagttc aattcacca ttttttagca     5580 gcaccggatt aacataactt tccaaaatgt tgtacgaacc gttaaacaaa aacagttcac    5640
ctcccttttc tatactattg tctgcgagca gttgtttgtt gttaaaaata acagccattg    5700
taatgagacg cacaaactaa tatcacaaac tggaaatgtc tatcaatata tagttgctct    5760
agttattaat agtaatcaat tacggggtca ttagttcata gcccatatat ggagttccgc    5820
gttacataac ttacggtaaa tggcccgcct ggctgaccgc ccaacgaccc ccgcccattg    5880
acgtcaataa tgacgtatgt tcccatagta acgccaatag ggactttcca ttgacgtcaa    5940
tgggtggact atttacggta aactgcccac ttggcagtac atcaagtgta tcatatgcca    6000
agtacgcccc ctattgacgt caatgacggt aaatggcccg cctggcatta tgcccagtac    6060
atgaccttat gggactttcc tacttggcag tacatctacg tattagtcat cgctattacc    6120
atgcatggtc gaggtgagcc ccacgttctg cttcactctc cccatctccc cccctcccc     6180 acccccaatt ttgtatttat ttatttttta attattttgt gcagcgatgg gggcgggggg    6240
gggggggggg cgcgcgccag gcggggcggg gcggggcgag gggcggggcg gggcgaggcg    6300
```

```
gagaggtgcg gcggcagcca atcagagcgg cgcgctccga aagtttcctt ttatggcgag    6360
gcggcggcgg cggcggccct ataaaaagcg aagcgcgcgg cgggcg                   6406

<210> SEQ ID NO 18
<211> LENGTH: 5965
<212> TYPE: DNA
<213> ORGANISM: Artificial Sequence
<220> FEATURE:
<223> OTHER INFORMATION: SEQ ID NO 18 (pTriEx-1-VAMP2)

<400> SEQUENCE: 18
ggagtcgctg cgacgctgcc ttcgccccgt gccccgctcc gccgccgcct cgcgccgccc      60
gccccggctc tgactgaccg cgttactccc acaggtgagc gggcgggacg gcccttctcc     120
ttcgggctgt aattagcgct tggtttaatg acggcttgtt tcttttctgt ggctgcgtga     180
aagccttgag gggctccggg agggcccttt gtgcgggggg agcggctcgg ggctgtccgc     240 gggggacgg ctgccttcgg ggggacggg gcagggcggg gttcggcttc tggcgtgtga      300
ccggcggctc tagagcctct gctaaccatg ttcatgcctt cttcttttc ctacagctcc     360 tgggcaacgt gctggttatt gtgctgtctc atcattttgg caaagaattg gatcggaccg     420
aaattaatac gactcactat aggggaattg tgagcggata caattcccc ggagttaatc      480 cgggaccttt aattcaaccc aacacaatat attatagtta ataagaatt attatcaaat      540 catttgtata ttaattaaaa tactatactg taaattacat tttatttaca atcaaaggag     600
atataccatg tctgctaccg ctgccacggc ccccctgct gccccggctg ggagggtgg      660 tccccctgca cccctccaa acctcaccag taacaggaga ctgcagcaga cccaggccca     720
ggtggatgag gtggtggaca tcatgagggt gaacgtggac aaggtcctgg agcgagacca     780
gaagctgtcg gagctggacg accgtgcaga tgcactccag gcggggggcct cccagtttga     840 acaagcgca gccaagctca agcgcaaata ctggtggaaa acctcaaga tgatgatcat      900 cttgggagtg atttgcgcca tcatcctcat catcatcata gtttacttca gcacttaact     960
cgagcaccac catcaccatc accatcacta agtgattaac ctcaggtgca ggctgcctat    1020
cagaaggtgg tggctggtgt ggccaatgcc ctggctcaca ataccactg agatcgatct    1080 ttttccctct gccaaaaatt atggggacat catgaagccc cttgagcatc tgacttctgg    1140
ctaataaagg aaatttattt tcattgcaat agtgtgttgg aattttttgt gtctctcact    1200
cggaaggaca tatgggaggg caaatcattt aaaacatcag aatgagtatt tggtttagag    1260
tttggcaaca tatgcccata tgtaactagc ataaccccct ggggcctcta acgggtctt    1320 gagggggtttt ttgctgaaag catgcggagg aaattctcct tgaagtttcc ctggtgttca    1380
aagtaaagga gtttgcacca gacgcacctc tgttcactgg tccggcgtat taaaacacga    1440
tacattgtta ttagtacatt tattaagcgc tagattctgt gcgttgttga tttacagaca    1500
attgttgtac gtatttaat aattcattaa atttataatc tttagggtgg tatgttagag    1560
cgaaaatcaa atgattttca gcgtctttat atctgaattt aaatattaaa tcctcaatag    1620
atttgtaaaa taggtttcga ttagtttcaa acaagggttg tttttccgaa ccgatggctg    1680
gactatctaa tggattttcg ctcaacgcca caaaacttgc caaatcttgt agcagcaatc    1740
tagctttgtc gatattcgtt tgtgttttgt tttgtaataa aggttcgacg tcgttcaaaa    1800
tattatgcgc ttttgtattt cttttcatcac tgtcgttagt gtacaattga ctcgacgtaa    1860
acacgttaaa tagagcttgg acatatttaa catcgggcgt gttagcttta ttaggccgat    1920
tatcgtcgtc gtcccaaccc tcgtcgttag aagttgcttc cgaagacgat tttgccatag    1980
```

```
ccacacgacg cctattaatt gtgtcggcta acacgtccgc gatcaaattt gtagttgagc   2040 ttttttggaat tatttctgat tgcgggcgtt tttgggcggg tttcaatcta actgtgcccg   2100
attttaattc agacaacacg ttagaaagcg atggtgcagg cggtggtaac atttcagacg   2160
gcaaatctac taatggcggc ggtggtggag ctgatgataa atctaccatc ggtggaggcg   2220
caggcggggc tggcggcgga ggcggaggcg gaggtggtgg cggtgatgca gacggcggtt   2280
taggctcaaa tgtctcttta ggcaacacag tcggcacctc aactattgta ctggtttcgg   2340
gcgccgtttt tggtttgacc ggtctgagac gagtgcgatt ttttcgtttt ctaatagctt   2400
ccaacaattg ttgtctgtcg tctaaaggtg cagcgggttg aggttccgtc ggcattggtg   2460
gagcgggcgg caattcagac atcgatggtg gtggtggtgg tggaggcgct ggaatgttag   2520
gcacgggaga aggtggtggc ggcggtgccg ccggtataat ttgttctggt ttagtttgtt   2580
cgcgcacgat tgtgggcacc ggcgcaggcg ccgctggctg cacaacggaa ggtcgtctgc   2640
ttcgaggcag cgcttggggt ggtggcaatt caatattata attggaatac aaatcgtaaa   2700
aatctgctat aagcattgta atttcgctat cgtttaccgt gccgatattt aacaaccgct   2760
caatgtaagc aattgtattg taaagagatt gtctcaagct cggaacgctg cgctcggtcg   2820
ttcggctgcg gcgagcggta tcagctcact caaaggcggt aatacggtta ccacagaat   2880 caggggataa gcaggaaag aacatgtgag caaaaggcca gcaaaaggcc aggaaccgta   2940
aaaaggccgc gttgctggcg ttttttccata ggctccgccc ccctgacgag catcacaaaa   3000
atcgacgctc aagtcagagg tggcgaaacc cgacaggact ataaagatac caggcgtttc   3060
cccctggaag ctccctcgtg cgctctcctg ttccgaccct gccgcttacc ggatacctgt   3120
ccgcctttct cccttcggga agcgtggcgc tttctcaatg ctcacgctgt aggtatctca   3180
gttcggtgta ggtcgttcgc tccaagctgg gctgtgtgca cgaaccccc gttcagcccg   3240 accgctgcgc cttatccggt aactatcgtc ttgagtccaa cccggtaaga cacgacttat   3300
cgccactggc agcagccact ggtaacagga ttagcagagc gaggtatgta ggcggtgcta   3360
cagagttctt gaagtggtgg cctaactacg gctacactag aaggacagta tttggtatct   3420
gcgctctgct gaagccagtt accttcggaa aaagagttgg tagctcttga tccggcaaac   3480
aaaccaccgc tggtagcggt ggttttttg tttgcaagca gcagattacg cgcagaaaaa   3540
aaggatctca agaagatcct ttgttaccaa tgcttaatca gtgaggcacc tatctcagcg   3600
atctgtctat ttcgttcatc catagttgcc tgactccccg tcgtgtagat aactacgata   3660
cgggagggct taccatctgg ccccagtgct gcaatgatac cgcgagaccc acgctcaccg   3720
gctccagatt tatcagcaat aaaccagcca gccggaaggg ccgagcgcag aagtggtcct   3780
gcaactttat ccgcctccat ccagtctatt aattgttgcc gggaagctag agtaagtagt   3840
tcgccagtta atagtttgcg caacgttgtt gccattgcta caggcatcgt ggtgtcacgc   3900
tcgtcgtttg gtatggcttc attcagctcc ggttcccaac gatcaaggcg agttacatga   3960
tcccccatgt tgtgcaaaaa agcggttagc tccttcggtc ctccgatcgt tgtcagaagt   4020
aagttggccg cagtgttatc actcatggtt atggcagcac tgcataattc tcttactgtc   4080
atgccatccg taagatgctt ttctgtgact ggtgagtact caaccaagtc attctgagaa   4140
tagtgtatgc ggcgaccgag ttgctcttgc ccggcgtcaa tacgggataa taccgcgcca   4200
catagcagaa ctttaaaagt gctcatcatt ggaaaacgtt cttcggggcg aaaactctca   4260
aggatcttac cgctgttgag atccagttcg atgtaaccca ctcgtgcacc caactgatct   4320
```

```
tcagcatctt ttactttcac cagcgtttct gggtgagcaa aacaggaag gcaaaatgcc    4380 gcaaaaaagg gaataagggc gacacggaaa tgttgaatac tcatactctt cctttttcaa    4440
tattattgaa gcatttatca gggttattgt ctcatgtccg cgcgtttcct gcatctttta    4500
atcaaatccc aagatgtgta taaaccacca aactgccaaa aaatgaaaac tgtcgacaag    4560
ctctgtccgt ttgctggcaa ctgcaagggt ctcaatccta tttgtaatta ttgaataata    4620
aaacaattat aaatgtcaaa tttgtttttt attaacgata caaccaaac gcaacaagaa     4680 catttgtagt attatctata attgaaaacg cgtagttata atcgctgagg taatatttaa    4740
aatcattttc aaatgattca cagttaattt gcgacaatat aattttattt tcacataaac    4800
tagacgcctt gtcgtcttct tcttcgtatt ccttctcttt ttcatttttc tcttcataaa    4860
aattaacata gttattatcg tatccatata tgtatctatc gtatagagta aattttttgt    4920
tgtcataaat atatatgtct tttttaatgg ggtgtatagt accgctgcgc atagttttc     4980 tgtaatttac aacagtgcta tttttctggta gttcttcgga gtgtgttgct ttaattatta   5040
aatttatata atcaatgaat ttgggatcgt cggttttgta caatatgttg ccggcatagt    5100
acgcagcttc ttctagttca attacaccat tttttagcag caccggatta acataacttt    5160
ccaaaatgtt gtacgaaccg ttaaacaaaa acagttcacc tcccttttct atactattgt    5220
ctgcgagcag ttgtttgttg ttaaaaataa cagccattgt aatgagacgc acaaactaat    5280
atcacaaact ggaaatgtct atcaatatat agttgctcta gttattaata gtaatcaatt    5340
acggggtcat tagttcatag cccatatatg gagttccgcg ttacataact acggtaaat     5400 ggcccgcctg gctgaccgcc caacgacccc cgcccattga cgtcaataat gacgtatgtt    5460
cccatagtaa cgccaatagg gactttccat tgacgtcaat gggtggacta tttacggtaa    5520
actgcccact tggcagtaca tcaagtgtat catatgccaa gtacgccccc tattgacgtc    5580
aatgacggta aatggcccgc ctggcattat gcccagtaca tgaccttatg gactttcct     5640 acttggcagt acatctacgt attagtcatc gctattacca tgcatggtcg aggtgagccc    5700
cacgttctgc ttcactctcc ccatctcccc ccctcccca ccccaatttt tgtatttatt      5760
tattttttaa ttattttgtg cagcgatggg ggcggggggg ggggggggc gcgcgccagg     5820 cggggcgggg cggggcgagg ggcggggcgg ggcgaggcgg agaggtgcgg cggcagccaa    5880
tcagagcggc gcgctccgaa agtttccttt tatggcgagg cggcggcggc ggcggcccta    5940
taaaaagcga agcgcgcggc gggcg                                          5965
```

<210> SEQ ID NO 19
<211> LENGTH: 864
<212> TYPE: PRT
<213> ORGANISM: Homo sapiens

<400> SEQUENCE: 19

```
Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Thr Thr Glu Tyr
65                  70                  75                  80
```

```
Ala Glu Phe Leu His Cys Lys Gly Lys Lys Phe Thr Asp Phe Glu Glu
                85                  90                  95
Val Arg Leu Glu Ile Glu Ala Glu Thr Asp Arg Val Thr Gly Thr Asn
            100                 105                 110
Lys Gly Ile Ser Pro Val Pro Ile Asn Leu Arg Val Tyr Ser Pro His
        115                 120                 125
Val Leu Asn Leu Thr Leu Val Asp Leu Pro Gly Met Thr Lys Val Pro
    130                 135                 140
Val Gly Asp Gln Pro Pro Asp Ile Glu Phe Gln Ile Arg Asp Met Leu
145                 150                 155                 160
Met Gln Phe Val Thr Lys Glu Asn Cys Leu Ile Leu Ala Val Ser Pro
                165                 170                 175
Ala Asn Ser Asp Leu Ala Asn Ser Asp Ala Leu Lys Val Ala Lys Glu
            180                 185                 190
Val Asp Pro Gln Gly Gln Arg Thr Ile Gly Val Ile Thr Lys Leu Asp
        195                 200                 205
Leu Met Asp Glu Gly Thr Asp Ala Arg Asp Val Leu Glu Asn Lys Leu
    210                 215                 220
Leu Pro Leu Arg Arg Gly Tyr Ile Gly Val Val Asn Arg Ser Gln Lys
225                 230                 235                 240
Asp Ile Asp Gly Lys Lys Asp Ile Thr Ala Ala Leu Ala Ala Glu Arg
                245                 250                 255
Lys Phe Phe Leu Ser His Pro Ser Tyr Arg His Leu Ala Asp Arg Met
            260                 265                 270
Gly Thr Pro Tyr Leu Gln Lys Val Leu Asn Gln Gln Leu Thr Asn His
        275                 280                 285
Ile Arg Asp Thr Leu Pro Gly Leu Arg Asn Lys Leu Gln Ser Gln Leu
    290                 295                 300
Leu Ser Ile Glu Lys Glu Val Glu Glu Tyr Lys Asn Phe Arg Pro Asp
305                 310                 315                 320
Asp Pro Ala Arg Lys Thr Lys Ala Leu Leu Gln Met Val Gln Gln Phe
                325                 330                 335
Ala Val Asp Phe Glu Lys Arg Ile Glu Gly Ser Gly Asp Gln Ile Asp
            340                 345                 350
Thr Tyr Glu Leu Ser Gly Gly Ala Arg Ile Asn Arg Ile Phe His Glu
        355                 360                 365
Arg Phe Pro Phe Glu Leu Val Lys Met Glu Phe Asp Glu Lys Glu Leu
    370                 375                 380
Arg Arg Glu Ile Ser Tyr Ala Ile Lys Asn Ile His Gly Ile Arg Thr
385                 390                 395                 400
Gly Leu Phe Thr Pro Asp Met Ala Phe Glu Thr Ile Val Lys Lys Gln
                405                 410                 415
Val Lys Lys Ile Arg Glu Pro Cys Leu Lys Cys Val Asp Met Val Ile
            420                 425                 430
Ser Glu Leu Ile Ser Thr Val Arg Gln Cys Thr Lys Lys Leu Gln Gln
        435                 440                 445
Tyr Pro Arg Leu Arg Glu Glu Met Glu Arg Ile Val Thr Thr His Ile
    450                 455                 460
Arg Glu Arg Glu Gly Arg Thr Lys Glu Gln Val Met Leu Leu Ile Asp
465                 470                 475                 480
Ile Glu Leu Ala Tyr Met Asn Thr Asn His Glu Asp Phe Ile Gly Phe
                485                 490                 495
Ala Asn Ala Gln Gln Arg Ser Asn Gln Met Asn Lys Lys Lys Thr Ser
```

```
                    500                 505                 510
Gly Asn Gln Asp Glu Ile Leu Val Ile Arg Lys Gly Trp Leu Thr Ile
                515                 520                 525

Asn Asn Ile Gly Ile Met Lys Gly Gly Ser Lys Glu Tyr Trp Phe Val
            530                 535                 540

Leu Thr Ala Glu Asn Leu Ser Trp Tyr Lys Asp Glu Glu Lys Glu
545                 550                 555                 560

Lys Lys Tyr Met Leu Ser Val Asp Asn Leu Lys Leu Arg Asp Val Glu
                565                 570                 575

Lys Gly Phe Met Ser Ser Lys His Ile Phe Ala Leu Phe Asn Thr Glu
                580                 585                 590

Gln Arg Asn Val Tyr Lys Asp Tyr Arg Gln Leu Glu Leu Ala Cys Glu
                595                 600                 605

Thr Gln Glu Glu Val Asp Ser Trp Lys Ala Ser Phe Leu Arg Ala Gly
                610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
                645                 650                 655

Arg Gln Val Glu Thr Ile Arg Asn Leu Val Asp Ser Tyr Met Ala Ile
                660                 665                 670

Val Asn Lys Thr Val Arg Asp Leu Met Pro Lys Thr Ile Met His Leu
                675                 680                 685

Met Ile Asn Asn Thr Lys Glu Phe Ile Phe Ser Glu Leu Leu Ala Asn
                690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
                725                 730                 735

Glu Ala Leu Ser Ile Ile Gly Asp Ile Asn Thr Thr Thr Val Ser Thr
                740                 745                 750

Pro Met Pro Pro Pro Val Asp Asp Ser Trp Leu Gln Val Gln Ser Val
                755                 760                 765

Pro Ala Gly Arg Arg Ser Pro Thr Ser Ser Pro Thr Pro Gln Arg Arg
                770                 775                 780

Ala Pro Ala Val Pro Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
                805                 810                 815

Ser Arg Pro Gly Ala Ser Pro Asp Pro Phe Gly Pro Pro Pro Gln Val
                820                 825                 830

Pro Ser Arg Pro Asn Arg Ala Pro Pro Gly Val Pro Ser Arg Ser Gly
                835                 840                 845

Gln Ala Ser Pro Ser Arg Pro Glu Ser Pro Arg Pro Pro Phe Asp Leu
850                 855                 860

<210> SEQ ID NO 20
<211> LENGTH: 3260
<212> TYPE: DNA
<213> ORGANISM: Homo sapiens

<400> SEQUENCE: 20
gggcgggggc cccgcggcgc aggcagtctg ggcgcgcggc tgcagcggcg gagccggagt    60
cggagccggg agcgctagcg gcagccggat cgcagcctgc ggggcccgcc gcagccatgg   120
```

```
gcaaccgcgg catggaagat ctcatcccgc tggtcaaccg gctgcaagac gccttctctg    180
ccatcggcca gaacgcggac ctcgacctgc cgcagatcgc tgtggtgggc ggccagagcg    240
ccggcaagag ctcggtgctc gagaatttcg taggcaggga cttcttgcct cgaggatctg    300
gcattgtcac ccgacgtccc ctggtcttgc agctggtcaa tgcaaccaca gaatatgccg    360
agttcctgca ctgcaaggga agaaattca ccgacttcga ggaggtgcgc cttgagatcg    420
aggccgagac cgacgggtc accggcacca acaagggcat ctcgccggtg cctatcaacc    480
tccgcgtcta ctcgccgcac gtgctgaacc tgaccctggt ggacctgccc ggaatgacca    540
aggtcccggt gggggaccaa cctcccgaca tcgagttcca gatccgagac atgcttatgc    600
agtttgtcac caaggagaac tgcctcatcc tggccgtgtc ccccgccaac tctgacctgg    660
ccaattctga cgccctcaag gtcgccaagg aggtggaccc caggggccag cgcaccatcg    720
gggtcatcac caagctggac ctgatggacg agggcacaga tgcccgtgat gtgctggaga    780
acaagctgct cccccgcgc agaggctaca ttggagtggt gaaccggagc cagaaggaca    840
ttgatggcaa gaaggacatt accgccgcct ggctgctgaa cgaaagttc ttcctctccc    900 atccatctta tcgccacttg gctgaccgta tgggcacgcc ctacctgcag aaggtcctca    960
atcagcaact gacgaaccac atccgggaca cactgccggg gctgcggaac aagctgcaga   1020
gccagctact gtccattgag aaggaggtgg aggaatacaa gaacttccgc cctgatgacc   1080
cagctcgcaa gaccaaggcc ctgctgcaga tggtccagca gttcgccgta gactttgaga   1140
agcgcattga gggctcagga gatcagatcg acacctacga actgtcaggg ggagcccgca   1200
ttaaccgaat cttccacgag cgcttccctt tcgagctggt caagatggag tttgatgaga   1260
aggaactccg aagggagatc agctatgcta tcaagaatat ccatggcatt agaacgggc    1320 tgtttacccc agacatggcc tttgagacca ttgtgaaaaa gcaggtgaag aagatccgag   1380
aaccgtgtct caagtgtgtg gacatggtta tctcggagct aatcagcacc gttagacagt   1440
gcaccaagaa gctccagcag taccccgcggc tacggggagga gatggagcgc atcgtgacca   1500
cccacatccg ggagcgcgag ggccgcacta aggagcaggt catgcttctc atcgatatcg   1560
agctggctta catgaacacc aaccatgagg acttcatagg ctttgccaat gctcagcaga   1620
ggagcaacca tgatgaacaag aagaagactt cagggaacca ggatgagatt ctggtcatcc   1680
gcaagggctg gctgactatc aataatattg gcatcatgaa aggggggctcc aaggagtact   1740 ggttttgtgct gactgctgag aatctgtcct ggtacaagga tgatgaggag aaagagaaga   1800
aatacatgct gtctgtggac aacctcaagc tgcgggacgt ggagaagggc tttatgtcga   1860
gcaagcatat cttttgccctc tttaacacgg agcagaggaa tgtctacaag gattatcggc   1920
agctggagct agcctgtgag acacaggagg aagtgcacag ctggaaggcc tccttcctga   1980
gggctggcgt gtaccctgag cgtgttgggg acaaagagaa agccagcgag accgaggaga   2040
atggctccga cagcttcatg cattccatgg acccacagct ggaacggcaa gtggagacca   2100
tccggaatct tgtggactca tacatggcca ttgtcaacaa gaccgtgagg gacctcatgc   2160
ccaagaccat catgcacctc atgattaaca ataccaagga gttcatcttc tcggagctgc   2220
tggccaacct gtactcgtgt ggggaccaga acacgctgat ggaggagtcg gcggagcagg   2280
cacagcggcg cgacgagatg ctgcgcatgt accacgcact gaaggaggcg ctcagcatca   2340
tcggcgacat caacacgacc accgtcagca cgcccatgcc cccgcccgtg acgactcct    2400 ggctgcaggt gcagagcgta ccggccggac gcaggtcgcc cacgtccagc cccacgccgc   2460
```

```
-continued agcgccgagc ccccgccgtg cccccagccc ggcccgggtc gcggggccct gctcctgggc   2520
ctccgcctgc tgggtccgcc ctgggggggg cgcccccccgt gccctccagg ccggggggctt   2580 cccctgaccc tttcggccct ccccctcagg tgccctcgcg ccccaaccgc gccccgcccg   2640
gggtccccag ccgatcgggt caggcaagtc catcccgtcc tgagagcccc aggcccccct   2700
tcgacctcta aacagatccc tcctcttctc ggagacctcc ctttccaagc ctgcctggac   2760
ggctgttctg tgacttgaca gtggctcccc cagccccaaa gccagccccc ttcatctgtg   2820
acttaatctg ttgtagtggt gagctgatac attcaggtgt gaccgttggt gaaaacttgt   2880
gccccttctg tggtatgccc ttgccctgtt ctataaatat ctataaatac tcatatatat   2940
acacacctac acatggccaa ccgcctcgcc tctagcgctg ggaatcagtc actgtgctat   3000
ccttgtggag tcttgtggcc caactaccag agaacgctgt cccccgacat cccactccaa   3060
agtgtgccac ctccagtgag cctccttgtc atgcccggcc tgtggacagc cagcccccgc   3120
catccctccc accccctacc aagcatgggg gtgctgtgca ggcagccgtg tggcctgaca   3180
gtttctacca gtcctgctgt ccctcggctg agaataaaac ccatttctgg atgatgggga   3240
atgtcaaaaa aaaaaaaaaa                                               3260
```